(12) United States Patent (10) Patent No.: US 7,942,940 B2
Renninger et al. (45) Date of Patent: May 17, 2011

(54) JET FUEL COMPOSITIONS AND METHODS OF MAKING AND USING SAME

(75) Inventors: Neil Stephen Renninger, Oakland, CA (US); Jason A. Ryder, Oakland, CA (US); Karl J. Fisher, Petaluma, CA (US)

(73) Assignee: Amyris Biotechnologies, Inc., Emeryville, CA (US)

( * ) Notice: Subject to any disclaimer, the term of this patent is extended or adjusted under 35 U.S.C. 154(b) by 847 days.

(21) Appl. No.: 11/986,484

(22) Filed: Nov. 20, 2007

(65) Prior Publication Data

US 2010/0281845 A1 Nov. 11, 2010

Related U.S. Application Data

(60) Provisional application No. 60/860,853, filed on Nov. 21, 2006, provisional application No. 60/951,235, filed on Jul. 23, 2007.

(51) Int. Cl.
*C10L 1/10* (2006.01)
*F02B 47/00* (2006.01)

(52) U.S. Cl. .................. 44/300; 123/1 A; 585/1; 585/14

(58) Field of Classification Search .................... 44/300; 585/1, 14; 123/1
See application file for complete search history.

(56) References Cited

U.S. PATENT DOCUMENTS

| 1,903,255 | A | * | 3/1933 | Busch .............................. 585/14 |
| 2,712,497 | A | * | 7/1955 | Fox et al. ......................... 44/427 |
| 3,441,497 | A | * | 4/1969 | Boodman et al. .............. 208/15 |
| 5,186,722 | A | | 2/1993 | Cantrell et al. |
| 5,501,713 | A | | 3/1996 | Wilkins, Jr. |
| 5,559,085 | A | | 9/1996 | Duncan, Jr. |
| 2004/0063143 | A1 | * | 4/2004 | Cheng et al. ....................... 435/6 |

FOREIGN PATENT DOCUMENTS

WO WO 2007/005944 A2 1/2007

OTHER PUBLICATIONS

Knowles, "Asymmetric Hydrogenations—The Monsanto L-Dopa Process," Asymmetric Catalysis on Industrial Scale: Challenges, Approaches and Solutions, Wiley-VCH Verlag GmbH & Co. KGaA Weinheim, pp. 23-53 (2004).
Gollis et al., "Evaluation of Pure Hydrocarbons as Jet Fuels," Journal of Chemical and Engineering Data, 7(2):311-316 (1962).
Imada et al., "Flavin-Catalyzed Generation of Diimide: An Environmentally Friendly Method for the Aerobic Hydrogenation of Olefins," J. Am. Chem. Soc., 127:14544-14545 (2005).
Kutzko, "Effect of Hydrocarbon Fuels on the Operation of Vapor Phase Fuel Systems," U.S. Department of Commerce, NTIS Publication No. AD-431315 (Mar. 1964).
Noyori, "Homogeneous Asymmetric Hydrogenation," Asymmetric Catalysis in Organic Synthesis, John Wiley & Sons Inc., New York, Chapter 2, pp. 16-94 (1994).

(Continued)

*Primary Examiner* — Cephia D Toomer
(74) *Attorney, Agent, or Firm* — Jones Day

(57) ABSTRACT

Provided herein are, among other things, jet fuel compositions and methods of making and using the same. In some embodiments, the fuel compositions comprise at least a fuel component readily and efficiently produced, at least in part, from a microorganism. In certain embodiments, the fuel compositions provided herein comprise a high concentration of at least a bioengineered fuel component. In further embodiments, the fuel compositions provided herein comprise a $C_{10}$ bicyclic isoprenoid such as carane, pinane, sabinane or a combination thereof.

27 Claims, 10 Drawing Sheets

OTHER PUBLICATIONS

Vineyard et al., "Asymmetric Hydrogenation. Rhodium Chiral Bisphosphine Catalyst," J. Am. Chem. Soc., 99(18):5946-5952 (1977).

U.S. Appl. No. 11/986,485, filed Nov. 20, 2007, Renninger et al.

PCT ISA/US International Search Report, dated Nov. 10, 2008, for International Application No. PCT/US2007/24266, filed Nov. 20, 2007.

* cited by examiner

| Property | Units | | Jet A | ASTM Test Method | Jet A (Base Fuel) | AMJ-400 (vol.% in Jet A) | | |
|---|---|---|---|---|---|---|---|---|
| | | | | | | 20 | 50 | 100 |
| COMPOSITION | | | | | | | | |
| Appearance | | | C & B | D4176-2 | C & B | C & B | C & B | C & B |
| Acidity | total mg KOH/g | max. | 0.10 | D3242 | 0.005 | 0.004 | 0.005 | 0.005 |
| Aromatics | vol.% | max. | 25 | D1319 | 16.9 | 15.9 | 9.4 | 0.5 |
| Sulfur | total mass % | max. | 0.30 | D4294 | 0.0685 | 0.0545 | 0.0344 | <0.0150 |
| Sulfur, mercaptan | mass % | max. | 0.003 | D3227 | 0.0019 | 0.0014 | 0.0009 | <0.0001 |
| VOLATILITY | | | | | | | | |
| 1. Physical Distillation | | | | | | | | |
| Distillation temperature | | | | | | | | |
| Initial boiling point, temperature | °C | | 205 | D86 | 153 | 159 | 161 | 164 |
| 10% recovered, temperature | °C | max. | report | D86 | 176 | 171 | 167 | 165 |
| 50% recovered, temperature | °C | max. | report | D86 | 209 | 196 | 179 | 165 |
| 90% recovered, temperature | °C | max. | 300 | D86 | 252 | 247 | 237 | 165 |
| Final boiling point, temperature | °C | max. | | D86 | 284 | 281 | 273 | 193 |
| Distillation recovery | vol.% | min. | | D86 | 97.6 | 98.1 | 98.4 | 99.3 |
| Distillation residue | vol.% | max. | 1.5 | D86 | 1.4 | 1.2 | 1.0 | 0.5 |
| Distillation loss | vol.% | max. | 1.5 | D86 | 1.0 | 0.7 | 0.6 | 0.2 |
| Flash Point | °C | min. | 38 | D86 | 43 | 43 | 44 | 43 |
| Density at 15°C | kg/m³ | range | 775 – 840 | D4052 | 811.0 | 820.4 | 834.9 | 860.3 |
| FLUIDITY | | | | | | | | |
| Freezing point | °C | max. | -40 | D2386 | -47 | -51 | -56.5 | <-70 |
| Viscosity at -20°C | mm²/s | max. | 8.0 | D445 | 5.162 | 4.688 | 4.997 | 5.573 |
| COMBUSTION | | | | | | | | |
| Net heat of combustion | MJ/kg | min. | 42.8 | D3338 | 43.4192 | 43.0534 | 42.9881 | 42.8011 |
| Smoke Point | mm | min. | 18 | D1322 | 21 | 23 | 25 | 28.5 |
| Naphthalenes, vol. | vol.% | max. | 3 | D1840 | 2.46 | 1.92 | 1.23 | 0.01 |
| CORROSION | | | | | | | | |
| Copper strip, 2 h at 100°C | | | No. 1 | D130 | 1A | 1B | 1A | 1A |
| THERMAL STABILITY | | | | | | | | |
| JFTOT | | | | | | | | |
| Temperature | °C | | | D3241 | 260 | 260 | 260 | 260 |
| Tube deposits less than | | | <3 | D3241 | <1 | <1 | <1 | <1 |
| Filter pressure drop/test time (150 min) | mm Hg/min | max. | 25 | D3241 | <1 | <1 | <1 | <1 |
| Spent fuel | mL | | | D3241 | 495 | 445 | 470 | 490 |
| | No Peacock or Abnormal Color Deposits | | | | | | | |
| CONTAMINANTS | | | | | | | | |
| Existent gum | mg/100mL | max. | 7 | D381 | 1 | 1 | 3 | 4 |
| Water reaction: | | | | | | | | |
| Interface rating | | max. | 1b | D1094 | 1b/2 | 1b/2 | 1b/2 | 1b/3 |
| Change in volume | mL | | | D1094 | 0 | 0 | 0 | 0 |
| Microseparometer (MSEP-A) | | | | | | | | |
| Without electrical conductivity additive | Rating | min. | 85 | D3948 | 99 | 99 | 99 | 98 |
| With electrical conductivity additive | Rating | min. | 70 | | | | | |
| ADDITIVES | | | | | | | | |
| Electrical conductivity | pS/m | | | D2624 | 4 | 4 | 4 | 2 |

SEQUENCE LISTING

<160> NUMBER OF SEQ ID NOS: 90

<210> SEQ ID NO 1
<211> LENGTH: 4247
<212> TYPE: DNA
<213> ORGANISM: Artificial Sequence
<220> FEATURE:
<223> OTHER INFORMATION: MevT66 operon

<400> SEQUENCE: 1

| | | | | | |
|---|---|---|---|---|---|
| gaattcaaag | gaggaaaata | aaatgaagaa | ctgtgtgatt | gtttctgcgg | tccgcacggc | 60 |
| gatcggcagc | tttaacggct | ctttagcgag | cacctctgca | atcgatctgg | gtgcgacggt | 120 |
| cattaaggcc | gccattgaac | gcgccaaaat | cgacagccag | cacgttgatg | aggtgatcat | 180 |
| gggcaatgtg | ttacaagccg | gcctgggtca | aaacccagcg | cgtcaagcac | tgttaaaatc | 240 |
| tggtctggcc | gagaccgtgt | gtggcttcac | cgtcaataag | gtttgcggct | ctggcctgaa | 300 |
| gagcgtggcc | ctggcagcac | aagcgattca | agccggtcag | gcacaaagca | tcgttgcggg | 360 |
| tggcatggaa | aacatgtctc | tggcgccgta | cttattagat | gccaaagccc | gcagcggtta | 420 |
| tcgcctgggc | gatggtcagg | tgtacgacgt | catcttacgc | gatggcttaa | tgtgcgcgac | 480 |
| ccacggttac | cacatgggta | ttacggccga | aaacgtggcg | aaagaatacg | gcattacgcg | 540 |
| cgagatgcag | gatgaattag | cactgcactc | tcagcgcaaa | gcagcagccg | cgatcgagtc | 600 |
| tggtgcgttt | acggcggaaa | tcgtgccagt | taacgtggtc | acgcgcaaga | agacgttcgt | 660 |
| tttcagccag | gacgagttcc | cgaaggcaaa | cagcaccgcg | gaggccttag | gtgccttacg | 720 |
| cccagccttt | gacaaagcgg | gcacggtcac | cgcnggtaat | gcgagcggca | tcaatgatgg | 780 |
| tgcagcggca | ctggtcatca | tggaagagag | cgccgcatta | gcagcgggtc | tgaccccatt | 840 |
| agcgcgcatt | aaatcttatg | ccagcggcgg | cgtcccacca | gccctgatgg | gcatgggtcc | 900 |
| ggtcccagcc | acgcaaaaag | ccctgcaatt | agcgggcctg | caactggccg | acattgatct | 960 |
| gatcgaggcg | aacgaggcgt | ttgcagcgca | gttcctggcg | gtgggtaaga | atctgggctt | 1020 |
| cgacagcgag | aaagtcaatg | tgaacggtgg | cgcgattgcg | ttaggccatc | cgattggtgc | 1080 |
| aagcggcgca | cgcatcttag | tgacgttact | gcacgccatg | caggcacgcg | acaagacctt | 1140 |
| aggcctggcg | accttatgta | ttggtggcgg | tcaaggtatc | gccatggtga | tcgaacgcct | 1200 |
| gaactgaaga | tctaggagga | aagcaaaatg | aaactgagca | ccaagctgtg | ctggtgtggc | 1260 |
| atcaagggtc | gcctgcgccc | acaaaagcag | caacagctgc | acaacacgaa | cctgcaaatg | 1320 |
| accgagctga | aaagcagaa | gacggccgag | caaaagaccc | gcccgcagaa | cgttggcatc | 1380 |
| aagggcatcc | agatttatat | cccgacgcag | tgtgtcaacc | aatctgagct | ggagaaattc | 1440 |
| gatggcgtca | gccagggtaa | gtacaccatc | ggcctgggcc | agaccaacat | gagcttcgtg | 1500 |
| aacgaccgtg | aggacatcta | ttctatgagc | ctgacggtgc | tgtctaagct | gatcaagagc | 1560 |
| tacaacatcg | acacgaataa | gatcggtcgt | ctggaggtgg | gtacggagac | gctgattgac | 1620 |
| aagagcaaaa | gcgtgaagtc | tgtcttaatg | cagctgttcg | gcgagaacac | ggatgtcgag | 1680 |
| ggtatcgaca | ccctgaacgc | gtgttacggc | ggcaccaacg | cactgttcaa | tagcctgaac | 1740 |
| tggattgaga | gcaacgcctg | ggatggccgc | gatgcgatcg | tcgtgtgcgg | cgatatcgcc | 1800 |
| atctatgaca | agggtgcggc | acgtccgacc | ggcggtgcag | gcaccgttgc | gatgtggatt | 1860 |
| ggcccggacg | caccaattgt | cttcgattct | gtccgcgcgt | cttacatgga | gcacgcctac | 1920 |
| gactttaca | agccggactt | cacgagcgaa | taccgtacg | tggacggcca | cttctctctg | 1980 |

```
acctgctatg tgaaggcgct ggaccaggtt tataagtctt atagcaaaaa ggcgatttct    2040
aagggcctgg tcagcgaccc ggcaggcagc gacgccctga acgtgctgaa gtatttcgac    2100
tacaacgtgt tccatgtccc gacctgcaaa ttagtgacca aatcttatgg ccgcctgtta    2160
tataatgatt tccgtgccaa cccgcagctg ttcccggagg ttgacgccga gctggcgacg    2220
cgtgattacg acgagagcct gaccgacaag aacatcgaga agaccttcgt caacgtcgcg    2280
aagccgttcc acaaagagcg tgtggcccaa gcctgatcg tcccgaccaa cacgggcaac    2340
atgtataccg cgtctgtcta cgcggcattc gcgagcctgc tgaattacgt cggttctgac    2400
gacctgcagg gcaagcgcgt tggcctgttc agctacggta gcggcttagc ggccagcctg    2460
tatagctgca aaattgtcgg cgacgtccag cacatcatca aggagctgga catcaccaac    2520
aagctggcga agcgcatcac cgagacgccg aaagattacg aggcagcgat cgagttacgc    2580
gagaatgcgc atctgaagaa gaacttcaag ccgcaaggta gcatcgagca cctgcagagc    2640
ggcgtctact acctgacgaa cattgacgac aagttccgcc gttcttatga cgtcaaaaag    2700
taactagtag gaggaaaaca tcatggtgct gacgaacaaa accgtcatta gcggcagcaa    2760
ggtgaagtct ctgagcagcg cccaaaagct ctagcagcggc ccgtctagca gcagcgagga    2820
ggacgacagc cgtgacattg agtctctgga caagaagatc cgcccgctgg aggagttaga    2880
ggccctgctg agcagcggca acaccaagca gctgaagaac aaggaagttg cagcgctggt    2940
gatccacggt aagctgccac tgtatgcgct ggaaaagaaa ctgggcgata cgacgcgtgc    3000
ggtcgcggtg cgtcgcaaag ccttaagcat cttagcggag gccccggtgt tagccagcga    3060
ccgcctgccg tacaagaact acgactacga ccgcgtgttt ggcgcgtgct gcgagaatgt    3120
cattggctac atgccgttac cggttggtgt gatcggcccg ctggtcattg atggcacgag    3180
ctatcacatt ccaatggcga ccacggaagg ttgcttagtc gccagcgcca tgcgtggctg    3240
taaggcgatt aacgccggcg gtggcgcgac gaccgtgtta accaaggatg gtatgacgcg    3300
cggtccggtc gtccgcttcc caacgctgaa gcgcagcggc gcgtgtaaga tttggctgga    3360
ttctgaggag ggccaaaacg cgatcaagaa agccttcaac tctacgagcc gtttcgcgcg    3420
tttacagcat atccagacct gcctggccgg cgacctgctg ttcatgcgct ccgcaccac    3480 cacgggcgat gcgatgggca tgaacatgat cagcaagggc gtcgaatata gcctgaaaca    3540
aatggtggaa gaatatggct gggaggacat ggaggttgtc tctgtgagcg gcaactattg    3600
caccgacaag aagccggcag ccattaactg gattgagggt cgcggcaaaa gcgtcgtggc    3660
agaagcgacc atcccaggcg acgtggtccg taaggttctg aagagcgacg tcagcgccct    3720
ggttgagtta aatatcgcga aaaacctggt cggcagcgcg atggcgggca gcgtgggtgg    3780
ctttaacgca catgcagcga atctggttac ggcggttttc ttagccttag gtcaggaccc    3840
agcccaaaat gtcgagagca gcaactgcat taccttaatg aaagaggttg acggtgacct    3900
gcgcatcagc gtttctatgc cgtctatcga ggtcggcacg atcggcggcg caccgttttt    3960
agaaccgcaa ggtgcgatgc tggatctgct gggcgtgcgc ggcccacatg caacggcccc    4020
aggcaccaat gcccgccaac tggcccgtat cgtggcctgc gcggttctgg cgggtgagct    4080
gagcctgtgc gccgcattag ccgcgggcca tttagttcaa tctcacatga cccacaaccg    4140
caagccggca gaaccaacca agccaaataa cctggacgca accgacatta accgtctgaa    4200
ggatggcagc gtcacgtgca ttaaaagctg agcatgctac taagctt              4247
```

<210> SEQ ID NO 2
<211> LENGTH: 1117
<212> TYPE: DNA

<213> ORGANISM: Artificial Sequence
<220> FEATURE:
<223> OTHER INFORMATION: geranyl diphosphate synthase of Arabidopsis thaliana, codon-optimized for expression in Escherichia coli with flanking NotI and SacI restriction sites

<400> SEQUENCE: 2

```
gcggccgcgg aaaaggaggc cggccggcat gctgctgtct aataaactgc gtgaaatggt      60
tctggctgaa gtacctaaac tggcctccgc agcagaatat tcttcaagc gtggcgttca     120
gggcaaacag ttccgtagca ccatcctgct gctgatggct accgccctgg acgtgcgtgt     180
cccggaagcc ctgatcggcg aatccaccga catcgtgacc tctgaactgc gtgttcgtca     240
gcgtggtatc gcggaaatca ccgaaatgat ccacgttgcg tctctgctgc acgacgatgt     300
gctggacgat gcagacaccc gtcgtggtgt tggttccctg aacgtggtga tgggtaacaa     360
aatgagcgtg ctggcaggcg actttctgct gtctcgcgcc tgtggtgctc tggctgcgct     420
gaagaacacc gaggtagtgg cactgctggc gactgccgta gagcacctgg ttaccggcga     480
aacgatggaa attacttctt ccaccgaaca gcgttactcc atggactact acatgcagaa     540
gacttactat aaaaccgcgt ccctgattag caactcttgt aaagcagtag cagtactgac     600
tggccaaact gcagaagtag cggtgctggc tttcgagtac ggtcgtaacc tgggtctggc     660
tttccagctg atcgatgaca tcctggactt tactggtacc agcgcaagcc tgggtaaagg     720
ttccctgtct gacattcgtc acggcgttat caccgctccg attctgttcg cgatggaaga    780
attcccgcag ctgcgtgaag ttgttgacca ggttgaaaaa gacccgcgta acgtcgatat    840
cgcactggaa tacctgggca atccaaagg tatccaacgc gcgcgtgaac tggctatgga    900
gcacgccaac ctggcagcag cagcaattgg ctctctgccg gaaaccgaca acgaagatgt    960
taaacgcagc cgtcgtgcac tgatcgacct gactcatcgt gtaatcaccc gcaacaaata   1020
agattgagtg atgttcctga gcatccacca gaacattccg cactttatct gtcgtattct   1080
gctggtgcaa ttcgtaagcc gctgataata ggagctc                             1117
```

<210> SEQ ID NO 3
<211> LENGTH: 5050
<212> TYPE: DNA
<213> ORGANISM: Artificial Sequence
<220> FEATURE:
<223> OTHER INFORMATION: ERG20-PGAL-tHMGR insert of pAM489

<400> SEQUENCE: 3

```
gtttaaacta ctattagctg aattgccact gctatcgttg ttagtggcgt tagtgcttgc      60
attcaaagac atggagggcg ttattacgcc ggagctcctc gacagcagat ctgatgactg     120
gtcaatatat ttttgcattg aggctctgtt tggaattata ttttgagatg acccatctaa     180
tgtactggta tcaccagatt tcatgtcgtt ttttaaagcg gctgcttgag tcttagcaat     240
agcgtcacca tctggtgaat cctttgaagg aaccactgac gaaggtttgg acagtgacga     300
agaggatctt tcctgctttg aattagtcgc gctgggagca gatgacgagt ggtggagct     360
gggggcagga ttgctggccg tcgtgggtcc tgaatgggtc cttggctggt ccatctctat     420
tctgaaaacg gaagaggagt agggaatatt actggctgaa ataagtcttg aatgaacgt     480
atacgcgtat atttctacca atctctcaac actgagtaat ggtagttata agaaagagac     540
cgagttaggg acagttagag gcggtggaga tattccttat ggcatgtctg gcgatgataa     600
aactttttcaa acggcagccc cgatctaaaa gagctgacac ccgggagtta tgacaattac     660
aacaacagaa ttctttctat atatgcacga acttgtaata tggaagaaat tatgacgtac     720
```

```
aaactataaa gtaaatattt tacgtaacac atggtgctgt tgtgcttctt tttcaagaga      780
ataccaatga cgtatgacta agtttaggat ttaatgcagg tgacggaccc atctttcaaa      840
cgatttatat cagtggcgtc caaattgtta ggttttgttg gttcagcagg tttcctgttg      900
tgggtcatat gactttgaac caaatggccg gctgctaggg cagcacataa ggataattca      960
cctgccaaga cggcacaggc aactattctt gctaattgac gtgcgttggt accaggagcg     1020
gtagcatgtg ggcctcttac acctaataag tccaacatgg caccttgtgg ttctagaaca     1080
gtaccaccac cgatggtacc tacttcgatg gatggcatgg atacggaaat tctcaaatca     1140
ccgtccactt ctttcatcaa tgttatacag ttggaacttt cgacattttg tgcaggatct     1200
tgtcctaatg ccaagaaaac agctgtcact aaattagctg catgtgcgtt aaatccacca     1260
acagacccag ccattgcaga tccaaccaaa ttcttagcaa tgttcaactc aaccaatgcg     1320
gaaacatcac tttttaacac ttttctgaca acatcaccag gaatagtagc ttctgcgacg     1380
acactcttac cacgaccttc gatccagttg atggcagctg gttttttgtc ggtacagtag     1440
ttaccagaaa cggagacaac ctccatatct tcccagccat actcttctac catttgcttt     1500
aatgagtatt cgacacccct agaaatcata ttcataccca ttgcgtcacc agtagttgtt     1560
ctaaatctca tgaagagtaa atctcctgct agacaagttt gaatatgttg cagacgtgca     1620
aatcttgatg tagagttaaa agctttttta attgcgtttt gtccctcttc tgagtctaac     1680
catatcttac aggcaccaga tcttttcaaa gttgggaaac ggactactgg gcctcttgtc     1740
ataccatcct tagttaaaac agttgttgca ccaccgccag cattgattgc cttacagcca     1800
cgcatggcag aagctaccaa acaaccctct gtagttgcca ttggtatatg ataagatgta     1860
ccatcgataa ccaagggggcc tataacacca acgggcaaag gcatgtaacc tataacattt     1920
tcacaacaag cgccaaatac gcggtcgtag tcataatttt tatatggtaa acgatcagat     1980
gctaatacag gagcttctgc caaaattgaa agagccttcc tacgtaccgc aaccgctctc     2040
gtagtatcac ctaatttttt ctccaaagcg tacaaaggta acttaccgtg aataaccaag     2100
gcagcgacct ctttgttctt caattgtttt gtatttccac tacttaataa tgcttctaat     2160
tcttctaaag gacgtatttt cttatccaag cttttcaatat cgcgggaatc atcttcctca     2220
ctagatgatg aaggtcctga tgagctcgat tgcgcagatg ataaactttt gactttcgat     2280
ccagaaatga ctgttttatt ggttaaaact ggtgtagaag cctttttgtac aggagcagta     2340 aaagacttct tggtgacttc agtcttcacc aattggtctg cagccattat agttttttct     2400
ccttgacgtt aaagtataga ggtatattaa caattttttg ttgatacttt tatgacattt     2460
gaataagaag taatacaaac cgaaaatgtt gaaagtatta gttaaagtgg ttatgcagct     2520
tttgcattta tatatctgtt aatagatcaa aaatcatcgc ttcgctgatt aattacccca     2580
gaaataaggc taaaaaacta atcgcattat tatcctatgg ttgttaattt gattcgttga     2640
tttgaaggtt tgtggggcca ggttactgcc aattttttcct cttcataacc ataaaagcta     2700
gtattgtaga atctttattg ttcggagcag tgcggcgcga ggcacatctg cgtttcagga     2760
acgcgaccgt tgaagaccag gacgcacgga ggagagtctt ccgtcggagg gctgtcgccc     2820
gctcggcggc ttctaatccg tacttcaata tagcaatgag cagttaagcg tattactgaa     2880
agttccaaag agaaggtttt tttaggctaa gataatgggg ctctttacat ttccacaaca     2940
tataagtaag attagatatg gatatgtata tggtggtatt gccatgtaat atgattatta     3000
aacttctttg cgtccatcca aaaaaaaagt aagaattttt gaaaattcaa tataaatggc     3060
ttcagaaaaa gaaattagga gagagagatt cttgaacgtt ttccctaaat tagtagagga     3120
```

```
attgaacgca tcgcttttgg cttacggtat gcctaaggaa gcatgtgact ggtatgccca    3180
ctcattgaac tacaacactc caggcggtaa gctaaataga ggtttgtccg ttgtggacac    3240
gtatgctatt ctctccaaca agaccgttga acaattgggg caagaagaat acgaaaaggt    3300
tgccattcta ggttggtgca ttgagttgtt gcaggcttac ttcttggtcg ccatgatat     3360 gatggacaag tccattacca gaagaggcca accatgttgg tacaaggttc ctgaagttgg    3420
ggaaattgcc atcaatgacg cattcatgtt agaggctgct atctacaagc ttttgaaatc    3480
tcacttcaga aacgaaaaat actacataga tatcaccgaa ttgttccatg aggtcacctt    3540
ccaaaccgaa ttgggccaat tgatggactt aatcactgca cctgaagaca agtcgactt     3600 gagtaagttc tccctaaaga agcactcctt catagttact ttcaagactg cttactattc    3660
tttctacttg cctgtcgcat tggccatgta cgttgccggt atcacggatg aaaaggattt    3720
gaaacaagcc agagatgtct tgattccatt gggtgaatac ttccaaattc aagatgacta    3780
cttagactgc ttcggtaccc cagaacagat cggtaagatc ggtacagata tccaagataa    3840
caaatgttct tgggtaatca acaaggcatt ggaacttgct tccgcagaac aaagaaagac    3900
tttagacgaa aattacggta agaaggactc agtcgcagaa gccaaatgca aaagatttt     3960 caatgacttg aaaattgaac agctatacca cgaatatgaa gagtctattg ccaaggattt    4020
gaaggccaaa atttctcagg tcgatgagtc tcgtggcttc aaagctgatg tcttaactgc    4080
gttcttgaac aaagttttaca agagaagcaa atagaactaa cgctaatcga taaaacatta    4140
gatttcaaac tagataagga ccatgtataa gaactatata cttccaatat aatatagtat    4200
aagctttaag atagtatctc tcgatctacc gttccacgtg actagtccaa ggatttttt     4260 taacccggga tatatgtgta cttgcagtt atgacgccag atggcagtag tggaagatat     4320
tctttattga aaaatagctt gtcaccttac gtacaatctt gatccggagc ttttctttt     4380 ttgccgatta agaattcggt cgaaaaaaga aaggagagg gccaagaggg agggcattgg     4440
tgactattga gcacgtgagt atacgtgatt aagcacacaa aggcagcttg gagtatgtct    4500
gttattaatt tcacaggtag ttctggtcca ttggtgaaag tttgcggctt gcagagcaca    4560
gaggccgcag aatgtgctct agattccgat gctgacttgc tgggtattat atgtgtgccc    4620
aatagaaaga gaacaattga cccggttatt gcaaggaaaa tttcaagtct tgtaaaagca    4680
tataaaaata gttcaggcac tccgaaatac ttggttggcg tgtttcgtaa tcaacctaag    4740
gaggatgttt tggctctggt caatgattac ggcattgata tcgtccaact gcatggagat    4800
gagtcgtggc aagaatacca agagttcctc ggtttgccag ttattaaaag actcgtatt     4860 ccaaaagact gcaacatact actcagtgca gcttcacaga aacctcattc gtttattccc    4920
ttgtttgatt cagaagcagg tggacaggt gaacttttgg attggaactc gatttctgac     4980
tgggttggaa ggcaagagag ccccgaaagc ttacatttta tgttagctgg tggactgacg    5040
ccgtttaaac                                                           5050
```

```
<210> SEQ ID NO 4
<211> LENGTH: 5488
<212> TYPE: DNA
<213> ORGANISM: Artificial Sequence
<220> FEATURE:
<223> OTHER INFORMATION: ERG13-PGAL-tHMGR insert of pAM491

<400> SEQUENCE: 4
gtttaaactt gctaaattcg agtgaaacac aggaagacca gaaatcctc  atttcatcca      60 tattaacaat aatttcaaat gtttatttgc attatttgaa actagggaag acaagcaacg     120
```

```
aaacgttttt gaaaattttg agtattttca ataaatttgt agaggactca gatattgaaa    180
aaaagctaca gcaattaata cttgataaga agagtattga aagggcaac  ggttcatcat    240 ctcatggatc tgcacatgaa caaacaccag agtcaaacga cgttgaaatt gaggctactg    300
cgccaattga tgacaataca gacgatgata acaaaccgaa gttatctgat gtagaaaagg    360
attaaagatg ctaagagata gtgatgatat ttcataaata atgtaattct atatatgtta    420 attaccttt ttgcgaggca tatttatggt gaaggataag tttgaccat  caaagaaggt     480 taatgtggct gtggtttcag ggtccatacc cgggagttat gacaattaca caacagaat     540 tctttctata tatgcacgaa cttgtaatat ggaagaaatt atgacgtaca aactataaag    600
taaatatttt acgtaacaca tggtgctgtt gtgcttcttt ttcaagagaa taccaatgac    660
gtatgactaa gtttaggatt taatgcaggt gacggaccca tctttcaaac gatttatatc    720
agtggcgtcc aaattgttag gttttgttgg ttcagcaggt ttcctgttgt gggtcatatg    780
actttgaacc aaatggccgg ctgctagggc agcacataag gataattcac ctgccaagac    840
ggcacaggca actattcttg ctaattgacg tgcgttggta ccaggagcgg tagcatgtgg    900
gcctcttaca cctaataagt ccaacatggc accttgtggt tctagaacag taccaccacc    960
gatggtacct acttcgatgg atggcatgga tacggaaatt ctcaaatcac cgtccacttc   1020
tttcatcaat gttatacagt tggaactttc gacattttgt gcaggatctt gtcctaatgc   1080
caagaaaaca gctgtcacta aattagctgc atgtgcgtta aatccaccaa cagacccagc   1140
cattgcagat ccaaccaaat tcttagcaat gttcaactca accatgcgg  aaacatcact    1200 ttttaacact tttctgacaa catcaccagg aatagtagct tctgcgacga cactcttacc   1260
acgaccttcg atccagttga tggcagctgg ttttttgtcg gtacagtagt taccagaaac   1320
ggagacaacc tccatatctt cccagccata ctcttctacc atttgcttta atgagtattc   1380 gacacccta  gaaatcatat tcatacccat tgcgtcacca gtagttgttc taaatctcat    1440
gaagagtaaa tctcctgcta gacaagtttg aatatgttgc agacgtgcaa atcttgatgt   1500
agagttaaaa gctttttaa  ttgcgttttg tccctcttct gagtctaacc atatcttaca    1560
ggcaccagat ctttttcaaag ttgggaaacg gactactggg cctcttgtca taccatcctt  1620
agttaaaaca gttgttgcac caccgccagc attgattgcc ttacagccac gcatggcaga   1680
agctaccaaa caaccctctg tagttgccat tggtatatga taagatgtac catcgataac   1740 caagggcct  ataacaccaa cgggcaaagg catgtaacct ataacatttt cacaacaagc    1800
gccaaatacg cggtcgtagt cataattttt atatggtaaa cgatcagatg ctaatacagg   1860
agcttctgcc aaaattgaaa gagccttcct acgtaccgca accgctctcg tagtatcacc   1920 taatttttc  tccaaagcgt acaaaggtaa cttaccgtga ataaccaagg cagcgacctc    1980
tttgttcttc aattgttttg tatttccact acttaataat gcttctaatt cttctaaagg   2040
acgtattttc ttatccaagc tttcaatatc gcgggaatca tcttcctcac tagatgatga   2100
aggtcctgat gagctcgatt gcgcagatga taaacttttg actttcgatc cagaaatgac   2160
tgttttattg gttaaaactg gtgtagaagc cttttgtaca ggagcagtaa aagacttctt   2220
ggtgacttca gtcttcacca attggtctgc agccattata gttttttctc cttgacgtta   2280
aagtatagag gtatattaac aattttttgt tgatactttt atgacatttg aataagaagt   2340
aatacaaacc gaaaatgttg aaagtattag ttaaagtggt tatgcagctt ttgcatttat   2400
atatctgtta atagatcaaa aatcatcgct tcgctgatta attccccag  aaataaggct    2460 aaaaaactaa tcgcattatt atcctatggt tgttaatttg attcgttgat ttgaaggttt   2520
```

```
gtggggccag gttactgcca attttttcctc ttcataacca taaaagctag tattgtagaa    2580
tctttattgt tcggagcagt gcggcgcgag gcacatctgc gtttcaggaa cgcgaccggt    2640
gaagaccagg acgcacggag gagagtcttc cgtcggaggg ctgtcgcccg ctcggcggct    2700
tctaatccgt acttcaatat agcaatgagc agttaagcgt attactgaaa gttccaaaga    2760
gaaggttttt ttaggctaag ataatggggc tctttacatt tccacaacat ataagtaaga    2820
ttagatatgg atatgtatat ggtggtattg ccatgtaata tgattattaa acttctttgc    2880
gtccatccaa aaaaaagta agaatttttg aaaattcaat ataaatgaaa ctctcaacta    2940
aactttgttg gtgtggtatt aaaggaagac ttaggccgca aaagcaacaa caattacaca    3000
atacaaactt gcaaatgact gaactaaaaa acaaaagac cgctgaacaa aaaaccagac    3060
ctcaaaatgt cggtattaaa ggtatccaaa tttacatccc aactcaatgt gtcaaccaat    3120
ctgagctaga gaaatttgat ggcgtttctc aaggtaaata cacaattggt ctgggccaaa    3180
ccaacatgtc ttttgtcaat gacagagaag atatctactc gatgtcccta actgttttgt    3240
ctaagttgat caagagttac aacatcgaca ccaacaaaat tggtagatta gaagtcggta    3300
ctgaaactct gattgacaag tccaagtctg tcaagtctgt cttgatgcaa ttgtttggtg    3360
aaaacactga cgtcgaaggt attgacacgc ttaatgcctg ttacggtggt accaacgcgt    3420
tgttcaactc tttgaactgg attgaatcta acgcatggga tggtagagac gccattgtag    3480
tttgcggtga tattgccatc tacgataagg gtgccgcaag accaaccggt ggtgccggta    3540
ctgttgctat gtggatcggt cctgatgctc caattgtatt tgactctgta agagcttctt    3600
acatggaaca cgcctacgat ttttacaagc cagatttcac cagcgaatat ccttacgtcg    3660
atggtcattt ttcattaact tgttacgtca aggctcttga tcaagtttac aagagttatt    3720
ccaagaaggc tatttctaaa gggttggtta gcgatcccgc tggttcggat gctttgaacg    3780
ttttgaaata tttcgactac aacgtttttcc atgttccaac ctgtaaattg gtcacaaaat    3840
catacggtag attactatat aacgatttca gagccaatcc tcaattgttc ccagaagttg    3900
acgccgaatt agctactcgc gattatgacg aatctttaac cgataagaac attgaaaaaa    3960
cttttgttaa tgttgctaag ccattccaca agagagagt tgcccaatct ttgattgttc    4020
caacaaacac aggtaacatg tacaccgcat ctgtttatgc cgcctttgca tctctattaa    4080
actatgttgg atctgacgac ttacaaggca agcgtgttgg tttattttct tacgttccg    4140 gtttagctgc atctctatat tcttgcaaaa ttgttggtga cgtccaacat attatcaagg    4200
aattagatat tactaacaaa ttagccaaga gaatcaccga aactccaaag gattacgaag    4260
ctgccatcga attgagagaa aatgcccatt tgaagaagaa cttcaaacct caaggttcca    4320
ttgagcattt gcaaagtggt gtttactact tgaccaacat cgatgacaaa tttagaagat    4380
cttacgatgt taaaaaataa tcttcccccca tcgattgcat cttgctgaac ccccttcata    4440
aatgctttat tttttggca gcctgctttt tttagctctc atttaataga gtagttttttt    4500 aatctatata ctaggaaaac tctttatttta ataacaatga tatatatata cccgggaagc    4560
ttttcaattc atctttttttt ttttttgttct ttttttttgat tccggtttct ttgaaattttt    4620 tttgattcgg taatctccga gcagaaggaa gaacgaagga aggagcacag acttagattg    4680
gtatatatac gcatatgtgg tgttgaagaa acatgaaatt gcccagtatt cttaacccaa    4740
ctgcacagaa caaaaacctg caggaaacga agataaatca tgtcgaaagc tacatataag    4800
gaacgtgctg ctactcatcc tagtcctgtt gctgccaagc tatttaatat catgcacgaa    4860
aagcaaacaa acttgtgtgc ttcattggat gttcgtacca ccaaggaatt actggagtta    4920
```

```
gttgaagcat taggtcccaa aatttgttta ctaaaaacac atgtggatat cttgactgat    4980
ttttccatgg agggcacagt taagccgcta aaggcattat ccgccaagta caatttttta    5040
ctcttcgaag acagaaaatt tgctgacatt ggtaatacag tcaaattgca gtactctgcg    5100
ggtgtataca gaatagcaga atgggcagac attacgaatg cacacggtgt ggtgggccca    5160
ggtattgtta gcggtttgaa gcaggcggcg gaagaagtaa caaggaacc tagaggcctt     5220 ttgatgttag cagaattgtc atgcaagggc tccctagcta ctggagaata tactaagggt    5280
actgttgaca ttgcgaagag cgacaaagat tttgttatcg gctttattgc tcaaagagac    5340
atgggtggaa gagatgaagg ttacgattgg ttgattatga cacccggtgt gggtttagat    5400
gacaagggag acgcattggg tcaacagtat agaaccgtgg atgatgtggt ctctacagga    5460
tctgacatta ttattgttgg gtttaaac                                       5488

<210> SEQ ID NO 5
<211> LENGTH: 4933
<212> TYPE: DNA
<213> ORGANISM: Artificial Sequence
<220> FEATURE:
<223> OTHER INFORMATION: IDI1-PGAL-tHMGR insert of pAM493

<400> SEQUENCE: 5
gtttaaacta ctcagtatat taagtttcga attgaagggc gaactcttat tcgaagtcgg      60
agtcaccaca acacttccgc ccatactctc cgaatcctcg tttcctaaag taagtttact     120
tccacttgta ggcctattat taatgatatc tgaataatcc tctattaggg ttggatcatt     180
cagtagcgcg tgcgattgaa aggagtccat gcccgacgtc gacgtgatta gcgaaggcgc     240
gtaaccattg tcatgtctag cagctataga actaacctcc ttgacaccac ttgcggaagt     300
ctcatcaaca tgctcttcct tattactcat tctcttacca agcagagaat gttatctaaa     360
aactacgtgt atttcacctc tttctcgact tgaacacgtc caactcctta agtactacca     420
cagccaggaa agaatggatc cagttctaca cgatagcaaa gcagaaaaca caaccagcgt     480 accectgtag aagcttcttt gtttacagca cttgatccat gtagccatac tcgaaatttc     540
aactcatctg aaacttttcc tgaaggttga aaaagaatgc cataagggtc acccgaagct     600
tattcacgcc cgggagttat gacaattaca acaacagaat tctttctata tatgcacgaa     660
cttgtaatat ggaagaaatt atgacgtaca aactataaag taaatatttt acgtaacaca     720
tggtgctgtt gtgcttcttt ttcaagagaa taccaatgac gtatgactaa gtttaggatt     780
taatgcaggt gacggaccca tctttcaaac gatttatatc agtggcgtcc aaattgttag     840
gttttgttgg ttcagcaggt ttcctgttgt gggtcatatg actttgaacc aaatggccgg     900
ctgctagggc agcacataag gataattcac ctgccaagac ggcacaggca actattcttg     960
ctaattgacg tgcgttggta ccaggagcgg tagcatgtgg gcctcttaca cctaataagt    1020
ccaacatggc accttgtggt tctagaacag taccaccacc gatggtacct acttcgatgg    1080
atggcatgga tacggaaatt ctcaaatcac cgtccacttc tttcatcaat gttatacagt    1140
tggaactttc gacattttgt gcaggatctt gtcctaatgc caagaaaaca gctgtcacta    1200
aattagctgc atgtgcgtta aatccaccaa cagacccagc cattgcagat ccaaccaaat    1260
tcttagcaat gttcaactca accaatgcgg aaacatcact ttttaacact tttctgacaa    1320
catcaccagg aatagtagct tctgcgacga cactcttacc acgaccttcg atccagttga    1380
tggcagctgg tttttgtcg gtacagtagt taccagaaac ggagcaacc tccatatctt      1440 cccagccata ctcttctacc atttgcttta atgagtattc gacacccta gaaatcatat      1500
```

```
tcatacccat tgcgtcacca gtagttgttc taaatctcat gaagagtaaa tctcctgcta    1560
gacaagtttg aatatgttgc agacgtgcaa atcttgatgt agagttaaaa gcttttttaa    1620
ttgcgttttg tccctcttct gagtctaacc atatcttaca ggcaccagat cttttcaaag    1680
ttgggaaacg gactactggg cctcttgtca taccatcctt agttaaaaca gttgttgcac    1740
caccgccagc attgattgcc ttacagccac gcatggcaga agctaccaaa caaccctctg    1800
tagttgccat tggtatatga taagatgtac catcgataac caaggggcct ataacaccaa    1860
cgggcaaagg catgtaacct ataacatttt cacaacaagc gccaaatacg cggtcgtagt    1920 cataatttt tatatggtaaa cgatcagatg ctaatacagg agcttctgcc aaaattgaaa     1980
gagccttcct acgtaccgca accgctctcg tagtatcacc taatttttc tccaaagcgt     2040 acaaaggtaa cttaccgtga ataaccaagg cagcgacctc tttgttcttc aattgttttg    2100
tatttccact acttaataat gcttctaatt cttctaaagg acgtattttc ttatccaagc    2160
tttcaatatc gcgggaatca tcttcctcac tagatgatga aggtcctgat gagctcgatt    2220
gcgcagatga taaacttttg actttcgatc cagaaatgac tgttttattg gttaaaactg    2280
gtgtagaagc cttttgtaca ggagcagtaa aagacttctt ggtgacttca gttttcacca    2340
attggtctgc agccattata gttttttctc cttgacgtta aagtatagag gtatattaac    2400 aatttttgt tgatactttt atgacatttg aataagaagt aatacaaacc gaaaatgttg     2460
aaagtattag ttaaagtggt tatgcagctt ttgcatttat atatctgtta atagatcaaa    2520
aatcatcgct tcgctgatta attacccag aaataaggct aaaaaactaa tcgcattatt     2580
atcctatggt tgttaatttg attcgttgat ttgaaggttt gtggggccag gttactgcca    2640 attttcctc ttcataacca taaaagctag tattgtagaa tctttattgt tcggagcagt     2700
gcggcgcgag gcacatctgc gtttcaggaa cgcgaccggt gaagaccagg acgcacggag    2760
gagagtcttc cgtcggaggg ctgtcgcccg ctcggcggct tctaatccgt acttcaatat    2820
agcaatgagc agttaagcgt attactgaaa gttccaaaga gaaggttttt ttaggctaag    2880 ataatgggc tctttacatt tccacaacat ataagtaaga ttagatatgg atatgtatat     2940
ggtggtattg ccatgtaata tgattattaa acttctttgc gtccatccaa aaaaaaagta    3000 agaattttg aaaattcaat ataaatgact gccgacaaca atagtatgcc ccatggtgca     3060
gtatctagtt acgccaaatt agtgcaaaac caaacacctg aagacatttt ggaagagttt    3120
cctgaaatta ttccattaca acaaagacct aatacccgat ctagtgagac gtcaaatgac    3180
gaaagcggag aaacatgttt ttctggtcat gatgaggagc aaattaagtt aatgaatgaa    3240
aattgtattg ttttggattg ggacgataat gctattggtg ccggtaccaa gaaagtttgt    3300
catttaatgg aaaatattga aaggggttta ctacatcgtg cattctccgt ctttattttc    3360
aatgaacaag gtgaattact tttacaacaa agagccactg aaaaaataac tttccctgat    3420 cttttggacta acacatgctg ctctcatcca ctatgtattg atgacgaatt aggtttgaag    3480
ggtaagctag acgataagat taagggcgct attactgcgg cggtgagaaa actagatcat    3540
gaattaggta ttccagaaga tgaaactaag acaaggggta agtttcactt tttaaacaga    3600
atccattaca tggcaccaag caatgaacca tggggtgaac atgaaattga ttacatccta    3660
ttttataaga tcaacgctaa agaaaacttg actgtcaacc caaacgtcaa tgaagttaga    3720
gacttcaaat gggtttcacc aaatgatttg aaaactatgt ttgctgaccc aagttacaag    3780 tttacgccctt ggtttaagat tatttgcgag aattacttat tcaactggtg ggagcaatta    3840
gatgaccttt ctgaagtgga aaatgacagg caaattcata gaatgctata acaacgcgtc    3900
```

-continued

| | | |
|---|---|---|
| aataatatag gctacataaa aatcataata actttgttat catagcaaaa tgtgatataa | 3960 |
| aacgtttcat ttcacctgaa aaatagtaaa aataggcgac aaaaatcctt agtaatatgt | 4020 |
| aaactttatt ttctttattt acccgggagt cagtctgact cttgcgagag atgaggatgt | 4080 |
| aataatacta atctcgaaga tgccatctaa tacatataga catacatata tatatatata | 4140 |
| cattctatat attcttaccc agattctttg aggtaagacg gttgggtttt atcttttgca | 4200 |
| gttggtacta ttaagaacaa tcgaatcata agcattgctt acaaagaata cacatacgaa | 4260 |
| atattaacga taatgtcaat tacgaagact gaactggacg gtatattgcc attggtggcc | 4320 |
| agaggtaaag ttagagacat atatgaggta gacgctggta cgttgctgtt tgttgctacg | 4380 |
| gatcgtatct ctgcatatga cgttattatg gaaaacagca ttcctgaaaa ggggatccta | 4440 |
| ttgaccaaac tgtcagagtt ctggttcaag ttcctgtcca acgatgttcg taatcatttg | 4500 |
| gtcgacatcg ccccaggtaa gactattttc gattatctac ctgcaaaatt gagcgaacca | 4560 |
| aagtacaaaa cgcaactaga agaccgctct ctattggttc acaaacataa actaattcca | 4620 |
| ttggaagtaa ttgtcagagg ctacatcacc ggatctgctt ggaaagagta cgtaaaaaca | 4680 |
| ggtactgtgc atggtttgaa acaacctcaa ggacttaaag aatctcaaga gttcccagaa | 4740 |
| ccaatcttca ccccatcgac caaggctgaa caaggtgaac atgacgaaaa catctctcct | 4800 |
| gcccaggccg ctgagctggt gggtgaagat ttgtcacgta gagtggcaga actggctgta | 4860 |
| aaactgtact ccaagtgcaa agattatgct aaggagaagg gcatcatcat cgcagacact | 4920 |
| aaattgttta aac | 4933 |

<210> SEQ ID NO 6
<211> LENGTH: 6408
<212> TYPE: DNA
<213> ORGANISM: Artificial Sequence
<220> FEATURE:
<223> OTHER INFORMATION: ERG10-PGAL-ERG12 insert of pAM495

<400> SEQUENCE: 6

| | | |
|---|---|---|
| gtttaaacta ttgtgagggt cagttatttc atccagatat aacccgagag gaaacttctt | 60 |
| agcgtctgtt ttcgtaccat aaggcagttc atgaggtata ttttcgttat tgaagcccag | 120 |
| ctcgtgaatg cttaatgctg ctgaactggt gtccatgtcg cctaggtacg caatctccac | 180 |
| aggctgcaaa ggttttgtct caagagcaat gttattgtgc accccgtaat tggtcaacaa | 240 |
| gtttaatctg tgcttgtcca ccagctctgt cgtaaccttc agttcatcga ctatctgaag | 300 |
| aaatttacta ggaatagtgc catggtacag caaccgagaa tggcaatttc tactcgggtt | 360 |
| cagcaacgct gcataaacgc tgttggtgcc gtagacatat tcgaagatag gattatcatt | 420 |
| cataagtttc agagcaatgt ccttattctg gaacttggat ttatggctct tttggtttaa | 480 |
| tttcgcctga ttcttgatct cctttagctt ctcgacgtgg gccttttttct tgccatatgg | 540 |
| atccgctgca cggtcctgtt ccctagcatg tacgtgagcg tatttccttt taaaccacga | 600 |
| cgctttgtct tcattcaacg tttcccattg ttttttttcta ctattgcttt gctgtgggaa | 660 |
| aaacttatcg aaagatgacg acttttttctt aattctcgtt ttaagagctt ggtgagcgct | 720 |
| aggagtcact gccaggtatc gtttgaacac ggcattagtc agggaagtca taacacagtc | 780 |
| cttttcccgca attttctttt tctattactc ttggcctcct ctagtacact ctatatttt | 840 |
| ttatgcctcg gtaatgattt tcattttttt tttttccacc tagcggatga ctcttttttt | 900 |
| ttcttagcga ttggcattat cacataatga attatacatt atataaagta atgtgatttc | 960 |
| ttcgaagaat atactaaagt ttagcttgcc tcgtccccgc cgggtcaccc ggccagcgac | 1020 |

```
atggaggccc agaataccct ccttgacagt cttgacgtgc gcagctcagg ggcatgatgt    1080
gactgtcgcc cgtacattta gcccatacat ccccatgtat aatcatttgc atccatacat    1140
tttgatggcc gcacggcgcg aagcaaaaat tacggctcct cgctgcagac ctgcgagcag    1200
ggaaacgctc ccctcacaga cgcgttgaat tgtccccacg ccgcgcccct gtagagaaat    1260
ataaaaggtt aggatttgcc actgaggttc ttctttcata tacttccttt taaaatcttg    1320
ctaggataca gttctcacat cacatccgaa cataaacaac catggcagaa ccagcccaaa    1380
aaaagcaaaa acaaactgtt caggagcgca aggcgtttat ctcccgtatc actaatgaaa    1440
ctaaaattca aatcgctatt tcgctgaatg gtggttatat tcaaataaaa gattcgattc    1500
ttcctgcaaa gaaggatgac gatgtagctt cccaagctac tcagtcacag gtcatcgata    1560
ttcacacagg tgttggcttt ttggatcata tgatccatgc gttggcaaaa cactctggtt    1620
ggtctcttat tgttgaatgt attggtgacc tgcacattga cgatcaccat actaccgaag    1680
attgcggtat cgcattaggg caagcgttca agaagcaat gggtgctgtc cgtggtgtaa    1740
aaagattcgg tactgggttc gcaccattgg atgaggcgct atcacgtgcc gtagtcgatt    1800
tatctagtag accatttgct gtaatcgacc ttggattgaa gagagagatg attggtgatt    1860
tatccactga aatgattcca cactttttgg aaagtttcgc ggaggcggcc agaattactt    1920
tgcatgttga ttgtctgaga ggtttcaacg atcaccacag aagtgagagt gcgttcaagg    1980
ctttggctgt tgccataaga gaagctattt ctagcaatgg caccaatgac gttccctcaa    2040
ccaaggtgt tttgatgtga agtactgaca ataaaaagat tcttgttttc aagaacttgt    2100
catttgtata gttttttat attgtagttg ttctattta atcaaatgtt agcgtgattt    2160
atatttttt tcgcctcgac atcatctgcc cagatgcgaa gttaagtgcg cagaaagtaa    2220
tatcatgcgt caatcgtatg tgaatgctgg tcgctatact gctgtcgatt cgatactaac    2280
gccgccatcc acccgggatg gtctgcttaa atttcattct gtcttcgaaa gctgaattga    2340
tactacgaaa aattttttt tgtttctctt tctatcttta ttacataaaa cttcatacac    2400
agttaagatt aaaaacaact aataaataat gcctatcgca aattagctta tgaagtccat    2460
ggtaaattcg tgtttcctgg caataataga tcgtcaattt gttgctttgt ggtagtttta    2520
ttttcaaata attggaatac tagggatttg attttaagat cttattcaa attttttgcg    2580
cttaacaaac agcagccagt cccacccaag tctgtttcaa atgtctcgta actaaaatca    2640
tcttgcaatt tcttttttgaa actgtcaatt tgctcttgag taatgtctct tcgtaacaaa    2700
gtcaaagagc aaccgccgcc accagcaccg gtaagttttg tggagccaat tctcaaatca    2760
tcgctcagat ttttaataag ttctaatcca ggatgagaaa caccgattga gacaagcagt    2820
ccatgattta ttcttatcaa ttccaatagt tgttcataca gttcattatt agtttctaca    2880
gcctcgtcat cggtgccttt acatttactt aacttagtca tgatctctaa gccttgtagg    2940
gcacattcac cctatggcatc tagaattggc ttcataactt caggaaattt ctcggtgacc    3000
aacacacgaa cgcgagcaac aagatctttt gtagaccttg gaattctagt ataggttagg    3060
atcattggaa tggctgggaa atcatctaag aacttaaaat tgtttgtgtt tattgttcca    3120
ttatgtgagt ctttttcaaa tagcagggca ttaccataag tggccacagc gttatctatt    3180
cctgaagggg taccgtgaat acacttttca cctatgaagg cccattgatt cactatatgc    3240
ttatcgtttt ctgacagctt ttccaagtca ttagatccta ttaaccccc caagtaggcc    3300
atagctaagg ccagtgatac agaaatagag gcgcttgagc ccaacccagc accgatgggt    3360
aaagtagact ttaaagaaaa cttaatattc ttggcatggg ggcataggca aacaaacata    3420
```

```
tacaggaaac aaaacgctgc atggtagtgg aaggattcgg atagttgagc taacaacgga   3480
tccaaaagac taacgagttc ctgagacaag ccatcggtgg cttgttgagc cttggccaat   3540
ttttgggagt ttacttgatc ctcggtgatg gcattgaaat cattgatgga ccacttatga   3600
ttaaagctaa tgtccgggaa gtccaattca atagtatctg gtgcagatga ctcgcttatt   3660
agcaggtagg ttctcaacgc agacacacta gcagcgacgg caggcttgtt gtacacagca   3720
gagtgttcac caaaaataat aacctttccc ggtgcagaag ttaagaacgg taatgacatt   3780 atagttttt ctccttgacg ttaaagtata gaggtatatt aacaattttt tgttgatact   3840
tttatgacat ttgaataaga agtaatacaa accgaaaatg ttgaaagtat tagttaaagt   3900
ggttatgcag cttttgcatt tatatatctg ttaatagatc aaaaatcatc gcttcgctga   3960
ttaattaccc cagaaataag gctaaaaaac taatcgcatt attatcctat ggttgttaat   4020
ttgattcgtt gatttgaagg tttgtggggc caggttactg ccaatttttc ctcttcataa   4080
ccataaaagc tagtattgta gaatctttat tgttcggagc agtgcggcgc gaggcacatc   4140
tgcgtttcag gaacgcgacc ggtgaagacc aggacgcacg gaggagagtc ttccgtcgga   4200
gggctgtcgc ccgctcggcg gcttctaatc cgtacttcaa tatagcaatg agcagttaag   4260
cgtattactg aaagttccaa agagaaggtt ttttaggct aagataatgg ggctctttac    4320
atttccacaa catataagta agattagata tggatatgta tatggtggta ttgccatgta   4380
atatgattat taaacttctt tgcgtccatc caaaaaaaaa gtaagaattt ttgaaaattc   4440
aatataaatg tctcagaacg tttacattgt atcgactgcc agaaccccaa ttggttcatt   4500
ccagggttct ctatcctcca agacagcagt ggaattgggt gctgttgctt taaaaggcgc   4560
cttggctaag gttccagaat tggatgcatc caaggatttt gacgaaatta tttttggtaa   4620
cgttctttct gccaatttgg gccaagctcc ggccagacaa gttgctttgg ctgccggttt   4680
gagtaatcat atcgttgcaa gcacagttaa caaggtctgt gcatccgcta tgaaggcaat   4740 catttttgggt gctcaatcca tcaaatgtgg taatgctgat gttgtcgtag ctggtggttg   4800
tgaatctatg actaacgcac catactacat gccagcagcc cgtgcgggtg ccaaatttgg   4860
ccaaactgtt cttgttgatg gtgtcgaaag agatgggttg aacgatgcgt acgatggtct   4920
agccatgggt gtacacgcag aaaagtgtgc ccgtgattgg gatattacta gagaacaaca   4980
agacaatttt gccatcgaat cctaccaaaa atctcaaaaa tctcaaaagg aaggtaaatt   5040
cgacaatgaa attgtacctg ttaccattaa gggatttaga ggtaagcctg atactcaagt   5100
cacgaaggac gaggaacctg ctagattaca cgttgaaaaa ttgagatctg caaggactgt   5160
tttccaaaaa gaaaacggta ctgttactgc cgctaacgct tctccaatca acgatggtgc   5220
tgcagccgtc atcttggttt ccgaaaaagt tttgaaggaa aagaatttga agcctttggc   5280
tattatcaaa ggttggggtg aggccgctca tcaaccagct gattttacat gggctccatc   5340
tcttgcagtt ccaaaggctt tgaaacatgc tggcatcgaa gacatcaatt ctgttgatta   5400
ctttgaattc aatgaagcct tttcggttgt cggtttggtg aacactaaga ttttgaagct   5460
agacccatct aaggttaatg tatatggtgg tgctgttgct ctaggtcacc cattgggttg   5520
ttctggtgct agagtggttg ttacactgct atccatctta cagcaagaag gaggtaagat   5580
cggtgttgcc gccattttgta atggtggtgg tggtgcttcc tctattgtca ttgaaaagat   5640
atgattacgt tctgcgattt tctcatgatc ttttttcataa aatacataaa tatataaatg   5700
gctttatgta taacaggcat aatttaaagt tttatttgcg attcatcgtt tttcaggtac   5760
tcaaacgctg aggtgtgcct tttgacttac ttttcccggg agaggctagc agaattaccc   5820
```

```
tccacgttga ttgtctgcga ggcaagaatg atcatcaccg tagtgagagt gcgttcaagg    5880
ctcttgcggt tgccataaga gaagccacct cgcccaatgg taccaacgat gttccctcca    5940
ccaaaggtgt tcttatgtag tgacaccgat tatttaaagc tgcagcatac gatatatata    6000
catgtgtata tatgtatacc tatgaatgtc agtaagtatg tatacgaaca gtatgatact    6060
gaagatgaca aggtaatgca tcattctata cgtgtcattc tgaacgaggc gcgctttcct    6120
tttttctttt tgcttttttct tttttttttct cttgaactcg agaaaaaaaa tataaaagag    6180
atggaggaac gggaaaaagt tagttgtggt gataggtggc aagtggtatt ccgtaagaac    6240
aacaagaaaa gcatttcata ttatggctga actgagcgaa caagtgcaaa atttaagcat    6300
caacgacaac aacgagaatg gttatgttcc tcctcactta agaggaaaac caagaagtgc    6360
cagaaataac agtagcaact acaataacaa caacggcggc gtttaaac              6408

<210> SEQ ID NO 7
<211> LENGTH: 6087
<212> TYPE: DNA
<213> ORGANISM: Artificial Sequence
<220> FEATURE:
<223> OTHER INFORMATION: ERG8-PGAL-ERG19 insert of pAM497

<400> SEQUENCE: 7
gtttaaactt ttccaatagg tggttagcaa tcgtcttact ttctaacttt tcttaccttt     60
tacatttcag caatatatat atatatattt caaggatata ccattctaat gtctgcccct    120
aagaagatcg tcgttttgcc aggtgaccac gttggtcaag aaatcacagc cgaagccatt    180
aaggttctta aagctatttc tgatgttcgt tccaatgtca agttcgattt cgaaaatcat    240
ttaattggtg gtgctgctat cgatgctaca ggtgttccac ttccagatga ggcgctggaa    300
gcctccaaga aggctgatgc cgttttgtta ggtgctgtgg gtggtcctaa atgggggtacc    360 ggtagtgtta gacctgaaca aggtttacta aaaatccgta aagaacttca attgtacgcc    420
aacttaagac catgtaactt tgcatccgac tctcttttag acttatctcc aatcaagcca    480
caatttgcta aaggtactga cttcgttgtt gtcagagaat tagtgggagg tatttacttt    540
ggtaagagaa aggaagacgt ttagcttgcc tcgtccccgc cgggtcaccc ggccagcgac    600
atggaggccc agaataccct ccttgacagt cttgacgtgc gcagctcagg ggcatgatgt    660
gactgtcgcc cgtacattta gcccatacat ccccatgtat aatcatttgc atccatacat    720
tttgatggcc gcacggcgcg aagcaaaaat tacggctcct cgctgcagac ctgcgagcag    780
ggaaacgctc ccctcacaga cgcgttgaat tgtcccacg ccgcgcccct gtagagaaat    840
ataaaaggtt aggatttgcc actgaggttc ttctttcata tacttccttt taaaatcttg    900
ctaggataca gttctcacat cacatccgaa cataaacaac catggcagaa ccagcccaaa    960
aaaagcaaaa acaaactgtt caggagcgca aggcgtttat ctcccgtatc actaatgaaa   1020
ctaaaattca aatcgctatt tcgctgaatg gtggttatat tcaaataaaa gattcgattc   1080
ttcctgcaaa gaaggatgac gatgtagctt cccaagctac tcagtcacag gtcatcgata   1140
ttcacacagg tgttggcttt ttggatcata tgatccatgc gttggcaaaa cactctggtt   1200
ggtctcttat tgttgaatgt attggtgacc tgcacattga cgatcaccat actaccgaag   1260
attgcggtat cgcattaggg caagcgttca agaagcaat gggtgctgtc cgtggtgtaa   1320
aaagattcgg tactgggttc gcaccattgg atgaggcgct atcacgtgcc gtagtcgatt   1380
tatctagtag accatttgct gtaatcgacc ttgattgaa gagagagatg attggtgatt   1440
tatccactga aatgattcca cacttttgg aaagtttcgc ggaggcggcc agaattactt   1500
```

```
tgcatgttga ttgtctgaga ggtttcaacg atcaccacag aagtgagagt gcgttcaagg   1560
ctttggctgt tgccataaga gaagctattt ctagcaatgg caccaatgac gttccctcaa   1620
ccaaaggtgt tttgatgtga agtactgaca ataaaaagat tcttgttttc aagaacttgt   1680
catttgtata gttttttttat attgtagttg ttctatttta atcaaatgtt agcgtgattt   1740
atattttttt tcgcctcgac atcatctgcc cagatgcgaa gttaagtgcg cagaaagtaa   1800
tatcatgcgt caatcgtatg tgaatgctgg tcgctatact gctgtcgatt cgatactaac   1860
gccgccatcc acccgggttt ctcattcaag tggtaactgc tgttaaaatt aagatattta   1920
taaattgaag cttggtcgtt ccgaccaata ccgtagggaa acgtaaatta gctattgtaa   1980
aaaaaggaaa agaaaagaaa agaaaaatgt tacatatcga attgatctta ttcctttggt   2040
agaccagtct ttgcgtcaat caaagattcg tttgtttctt gtgggcctga accgacttga   2100
gttaaaatca ctctggcaac atccttttgc aactcaagat ccaattcacg tgcagtaaag   2160
ttagatgatt caaattgatg gttgaaagcc tcaagctgct cagtagtaaa tttcttgtcc   2220
catccaggaa cagagccaaa caatttatag ataaatgcaa agagtttcga ctcattttca   2280
gctaagtagt acaacacagc atttggacct gcatcaaacg tgtatgcaac gattgtttct   2340
ccgtaaaact gattaatggt gtggcaccaa ctgatgatac gcttggaagt gtcattcatg   2400
tagaatattg gagggaaaga gtccaaacat gtggcatgga aagagttgga atccatcatt   2460
gtttcctttg caaggtggc gaaatctttt tcaacaatgg ctttacgcat gacttcaaat   2520
ctctttggta cgacatgttc aattctttct ttaaatagtt cggaggttgc cacggtcaat   2580 tgcatacccct gagtggaact cacatccttt ttaatatcgc tgacaactag gacacaagct   2640
ttcatctgag gccagtcaga gctgtctgcg atttgtactg ccatggaatc atgaccatct   2700
tcagcttttc ccatttccca ggccacgtat ccgccaaaca acgatctaca agctgaacca   2760 gaccccttc ttgctattct agatatttct gaagttgact gtggtaattg gtataactta   2820
gcaattgcag agaccaatgc agcaaagcca gcagcggagg aagctaaacc agctgctgta   2880
ggaaagttat tttcggagac aatgtggagt ttccattgag ataatgtggg caatgaggcg   2940
tccttcgatt ccatttcctt tcttaattgg cgtaggtcgc gcagacaatt ttgagttctt   3000
tcattgtcga tgctgtgtgg ttctccattt aaccacaaag tgtcgcgttc aaactcaggt   3060
gcagtagccg cagaggtcaa cgttctgagg tcatcttgcg ataaagtcac tgatatggac   3120
gaattggtgg gcagattcaa cttcgtgtcc ctttctccccc aatacttaag ggttgcgatg   3180
ttgacgggtg cggtaacgga tgctgtgtaa acggtcatta tagttttttc tccttgacgt   3240
taaagtatag aggtatatta acaatttttt gttgatactt ttatgacatt tgaataagaa   3300
gtaatacaaa ccgaaaatgt tgaaagtatt agttaaagtg gttatgcagc ttttgcattt   3360
atatatctgt taatagatca aaaatcatcg cttcgctgat taattacccc agaaataagg   3420
ctaaaaaact aatcgcatta ttatcctatg gttgttaatt tgattcgttg atttgaaggt   3480
ttgtggggcc aggttactgc caattttttcc tcttcataac cataaaagct agtattgtag   3540
aatctttatt gttcggagca gtgcggcgcg aggcacatct gcgtttcagg aacgcgaccg   3600
gtgaagacca ggacgcacgg aggagagtct tccgtcggag ggctgtcgcc cgctcggcgg   3660
cttctaatcc gtacttcaat atagcaatga gcagttaagc gtattactga aagttccaaa   3720
gagaaggttt ttttaggcta agataatggg gctctttaca tttccacaac atataagtaa   3780
gattagatat ggatatgtat atggtggtat tgccatgtaa tatgattatt aaacttcttt   3840
gcgtccatcc aaaaaaaaag taagaatttt tgaaaattca atataaatgt cagagttgag   3900
```

```
agccttcagt gccccaggga aagcgttact agctggtgga tatttagttt tagatccgaa    3960
atatgaagca tttgtagtcg gattatcggc aagaatgcat gctgtagccc atccttacgg    4020
ttcattgcaa gagtctgata agtttgaagt gcgtgtgaaa agtaaacaat ttaaagatgg    4080
ggagtggctg taccatataa gtcctaaaac tggcttcatt cctgtttcga taggcggatc    4140
taagaacccct ttcattgaaa aagttatcgc taacgtattt agctacttta agcctaacat    4200
ggacgactac tgcaatagaa acttgttcgt tattgatatt ttctctgatg atgcctacca    4260
ttctcaggag gacagcgtta ccgaacatcg tggcaacaga agattgagtt ttcattcgca    4320
cagaattgaa gaagttccca aaacagggct gggctcctcg gcaggtttag tcacagtttt    4380
aactacagct ttggcctcct tttttgtatc ggacctggaa aataatgtag acaaatatag    4440
agaagttatt cataatttat cacaagttgc tcattgtcaa gctcagggta aaattggaag    4500
cgggtttgat gtagcggcgg cagcatatgg atctatcaga tatagaagat tcccacccgc    4560
attaatctct aatttgccag atattggaag tgctacttac ggcagtaaac tggcgcattt    4620
ggttaatgaa gaagactgga ataacgat taaaagtaac catttacctt cgggattaac    4680
tttatggatg ggcgatatta agaatggttc agaaacagta aaactggtcc agaaggtaaa    4740
aaattggtat gattcgcata tgccggaaag cttgaaaata tatacagaac tcgatcatgc    4800
aaattctaga tttatggatg gactatctaa actagatcgc ttacacgaga ctcatgacga    4860
ttacagcgat cagatatttg agtctcttga gaggaatgac tgtacctgtc aaaagtatcc    4920
tgagatcaca gaagttagag atgcagttgc cacaattaga cgttccttta gaaaaataac    4980
taaagaatct ggtgccgata tcgaacctcc cgtacaaact agcttattgg atgattgcca    5040
gaccttaaaa ggagttctta cttgcttaat acctggtgct ggtggttatg acgccattgc    5100
agtgattgct aagcaagatg ttgatcttag ggctcaaacc gctgatgaca aaagattttc    5160
taaggttcaa tggctggatg taactcaggc tgactgggt gttaggaaag aaaaagatcc    5220
ggaaacttat cttgataaat aacttaaggt agataatagt ggtccatgtg acatctttat    5280
aaatgtgaag tttgaagtga ccgcgcttaa catctaacca ttcatcttcc gatagtactt    5340
gaaattgttc ctttcggcgg catgataaaa ttcttttaat gggtacaagc tacccgggcc    5400
cgggaaagat tctcttttt tatgatattt gtacataaac tttataaatg aaattcataa    5460
tagaaacgac acgaaattac aaaatggaat atgttcatag ggtagacgaa actatatacg    5520
caatctacat acatttatca agaaggagaa aaaggaggat gtaaaggaat acaggtaagc    5580
aaattgatac taatggctca acgtgataag gaaaaagaat tgcactttaa cattaatatt    5640
gacaaggagg agggcaccac acaaaaagtt aggtgtaaca gaaaatcatg aaactatgat    5700
tcctaattta tatattggag gattttctct aaaaaaaaaa aaatacaaca aataaaaaac    5760
actcaatgac ctgaccattt gatggagttt aagtcaatac cttcttgaac catttcccat    5820
aatggtgaaa gttccctcaa gaattttact ctgtcagaaa cggccttaac gacgtagtcg    5880
acctcctctt cagtactaaa tctaccaata ccaaatctga tggaagaatg ggctaatgca    5940
tcatccttac ccagcgcatg taaaacataa gaaggttcta gggaagcaga tgtacaggct    6000
gaacccgagg ataatgcgat atcccttagt gccatcaata aagattctcc ttccacgtag    6060
gcgaaagaaa cgttaacacg tttaaac                                        6087

<210> SEQ ID NO 8
<211> LENGTH: 1782
<212> TYPE: DNA
<213> ORGANISM: Artificial Sequence
<220> FEATURE:
```

<223> OTHER INFORMATION: alpha-pinene synthase of Pinus taeda,
      codon-optimized for expression in Escherichia coli with flanking
      XmaI and XbaI restriction sites

<400> SEQUENCE: 8

```
ggaattcccg ggcgagctct ttacacttta tgcttccggc tcgtataatg tgtggaattg      60
tgagcggata acaattgaat tcaaaggagg aaaataaaat ggatgatgat tctattgcat     120
ctctgagcac gtcctatgaa gctcctagct accgcaagcg tgcggataaa ctgattggcg     180
aagtgaaaaa tatctttgat ctgatgtctg tggaggatgg tgttttcact agcccgctga     240
gcgacctgca ccatcgcctg tggatggttg actctgttga acgcctgggc atcgaccgtc     300
actttaagga cgagatcaac agcgctctgg atcatgtgta ctcttactgg accgaaaagg     360
gtatcggccg tggccgtgaa tctggtgtaa ccgatctgaa cagcaccgca ctgggcctgc     420
gtaccctgcg cctgcacggt tataccgtat ctagccatgt cctggatcac ttcaagaacg     480
aaaaaggtca gttcacttgt tccgcgatcc agaccgaagg cgaaattcgt gacgttctga     540
acctgttccg tgcgtccctg atcgcgtttc cgggtgaaaa gatcatggaa gcggccgaaa     600
tcttctccac catgtacctg aaagacgctc tgcagaaaat tccgccgtcc ggtctgagcc     660
aggaaattga atatctgctg gagttcggct ggcacaccaa cctgccgcgt atggaaaccc     720
gcatgtatat cgacgtcttt ggcgaagaca ccaccttcga accccgtac ctgatccgtg     780
aaaaactgct ggaactggcg aaactggaat ttaacatctt tcattccctg gtgaaacgtg     840
aactgcagtc cctgtcccgc tggtggaagg actacggttt ccctgaaatc accttctctc     900
gtcaccgtca cgtagaatac tacccctgg ctgcctgtat cgctaatgac ccgaaacaca     960
gcgcttttcg tctgggcttc ggtaaaatct ctcacatgat taccatcctg gatgacattt    1020
atgacacctt cggcaccatg gaagagctga actgctgac cgcagctttc aaacgttggg    1080
acccgagctc cattgagtgt ctgccagact atatgaaggg tgtttatatg gcagtttacg    1140
ataacattaa cgagatggcg cgtgaagcgc agaagatcca gggttgggac acggtttcct    1200
atgcgcgcaa gtcttgggaa gcttttatcg gcgcgtacat tcaggagct aaatggattt    1260
cttccggcta cctgccgacc ttcgacgaat acctggagaa cggtaaagtc tccttcggct    1320
cccgtatcac taccctggaa ccgatgctga ctctgggttt tcgctgccg cctcgtattc    1380
tgcaggaaat cgacttcccg tctaaattca acgacctgat ctgtgcaatc ctgcgtctga    1440
aaggcgatac tcagtgctat aaagcggacc gtgcacgcgg tgaagaagcc tctgcggttt    1500
cctgttatat gaaagaccat ccgggtatta ccgaagaaga tgccgtaaac caggtgaacg    1560
cgatggtgga taatctgacc aaagaactga actgggaact gctgcgtccg gattccggcg    1620
tcccgatcag ctataaaaag gtggcgttcg atatttgccg cgttttccac tacgttacca    1680
aatatcgcga tggtttctcc gtggcatcta tcgaaatcaa aaacctggtg actcgtaccg    1740
tcgtggaaac ggtgccgctg tgatagtaat ctagaggaat tt                       1782
```

<210> SEQ ID NO 9
<211> LENGTH: 2121
<212> TYPE: DNA
<213> ORGANISM: Artificial Sequence
<220> FEATURE:
<223> OTHER INFORMATION: KanMX-PMET3 region from pAM328
<220> FEATURE:
<221> NAME/KEY: misc_feature
<222> LOCATION: 13, 2109
<223> OTHER INFORMATION: n = A,T,C or G

<400> SEQUENCE: 9

```
gaattcgccc ttntggatgg cggcgttagt atcgaatcga cagcagtata gcgaccagca      60
ttcacatacg attgacgcat gatattactt tctgcgcact taacttcgca tctgggcaga     120
tgatgtcgag gcgaaaaaaa atataaatca cgctaacatt tgattaaaat agaacaacta     180
caatataaaa aaactataca aatgacaagt tcttgaaaac aagaatcttt ttattgtcag     240
tactgattag aaaaactcat cgagcatcaa atgaaactgc aatttattca tatcaggatt     300
atcaatacca tatttttgaa aaagccgttt ctgtaatgaa ggagaaaact caccgaggca     360
gttccatagg atggcaagat cctggtatcg gtctgcgatt ccgactcgtc aacatcaat      420
acaacctatt aatttcccct cgtcaaaaat aaggttatca agtgagaaat caccatgagt     480
gacgactgaa tccggtgaga atggcaaaag cttatgcatt tctttccaga cttgttcaac     540
aggccagcca ttacgctcgt catcaaaatc actcgcatca accaaaccgt tattcattcg     600
tgattgcgcc tgagcgagac gaaatacgcg atcgctgtta aaaggacaat acaaacagg      660
aatcgaatgc aaccggcgca ggaacactgc cagcgcatca acaatatttt cacctgaatc     720
aggatattct tctaatacct ggaatgctgt tttgccgggg atcgcagtgg tgagtaacca     780
tgcatcatca ggagtacgga taaaatgctt gatggtcgga agaggcataa attccgtcag     840
ccagtttagt ctgaccatct catctgtaac atcattggca acgctacctt tgccatgttt     900
cagaaacaac tctggcgcat cgggcttccc atacaatcga tagattgtcg cacctgattg     960
cccgacatta tcgcgagccc atttataccc atataaatca gcatccatgt tggaatttaa    1020
tcgcggcctc gaaacgtgag tcttttcctt acccatggtt gtttatgttc ggatgtgatg    1080
tgagaactgt atcctagcaa gatttttaaaa ggaagtatat gaaagaagaa cctcagtggc    1140
aaatcctaac cttttatatt tctctacagg ggcgcggcgt ggggacaatt caacgcgtct    1200
gtgagggag cgtttccctg ctcgcaggtc tgcagcgagg agccgtaatt tttgcttcgc    1260
gccgtgcggc catcaaaatg tatggatgca aatgattata catggggatg tatgggctaa    1320
atgtacgggc gacagtcaca tcatgcccct gagctgcgca cgtcaagact gtcaaggagg    1380
gtattctggg cctccatgtc gctggccggg tgacccggcg gggacgaggc aagctaaaca    1440
gatctgatct tgaaactgag taagatgctc agaatacccg tcaagataag agtataatgt    1500
agagtaatat accaagtatt cagcatattc tcctcttctt ttgtataaat cacggaaggg    1560
atgatttata agaaaaatga atactattac acttcattta ccaccctctg atctagattt    1620
tccaacgata tgtacgtagt ggtataaggt gaggggtcc acagatataa catcgtttaa    1680
tttagtacta acagagactt ttgtcacaac tacatataag tgtacaaata tagtacagat    1740
atgacacact tgtagcgcca acgcgcatcc tacggattgc tgacagaaaa aaaggtcacg    1800
tgaccagaaa agtcacgtgt aattttgtaa ctcaccgcat tctagcggtc cctgtcgtgc    1860
acactgcact caacaccata aaccttagca acctccaaag gaaatcaccg tataacaaag    1920
ccacagtttt acaacttagt ctcttatgaa gttacttacc aatgagaaat agaggctctt    1980
tctcgagaaa tatgaatatg gatatatata tatatatata tatatatata tatatatgta    2040
aacttggttc ttttttagct tgtgatctct agcttgggtc tctctctgtc gtaacagttg    2100
tgatatcgna agggcgaatt c                                              2121
```

<210> SEQ ID NO 10
<211> LENGTH: 7348
<212> TYPE: DNA
<213> ORGANISM: Artificial Sequence
<220> FEATURE:
<223> OTHER INFORMATION: pAM178

<400> SEQUENCE: 10

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatcga ctacgtcgta aggccgtttc tgacagagta aaattcttga gggaactttc     240
accattatgg gaaatgcttc aagaaggtat tgacttaaac tccatcaaat ggtcaggtca     300
ttgagtgttt tttatttgtt gtattttttt tttttagag aaaatcctcc aatatcaaat     360
taggaatcgt agtttcatga ttttctgtta cacctaactt tttgtgtggt gccctcctcc     420
ttgtcaatat taatgttaaa gtgcaattct tttttcttat cacgttgagc cattagtatc     480
aatttgctta cctgtattcc tttactatcc tccttttct ccttcttgat aaatgtatgt     540
agattgcgta tatagtttcg tctaccctat gaacatattc cattttgtaa tttcgtgtcg     600
tttctattat gaatttcatt tataaagttt atgtacaaat atcataaaaa aagagaatct     660
ttttaagcaa ggattttctt aacttcttcg gcgacagcat caccgacttc ggtggtactg     720
ttggaaccac ctaaatcacc agttctgata cctgcatcca aaaccttttt aactgcatct     780
tcaatggcct taccttcttc aggcaagttc aatgacaatt tcaacatcat tgcagcagac     840
aagatagtgg cgatagggtc aaccttattc ttttggcaaat ctggagcaga accgtggcat     900
ggttcgtaca aaccaaatgc ggtgttcttg tctggcaaag aggccaagga cgcagatggc     960
aacaaaccca aggaacctgg ataacggag gcttcatcgg agatgatatc accaaacatg    1020
ttgctggtga ttataatacc atttaggtgg gttgggttct taactaggat catggcggca    1080
gaatcaatca attgatgttg aaccttcaat gtagggaatt cgttcttgat ggtttcctcc    1140
acagttttc tccataatct tgaagaggcc aaaagattag ctttatccaa ggaccaaata    1200
ggcaatggtg gctcatgttg tagggccatg aaagcggcca ttcttgtgat tctttgcact    1260
tctggaacgg tgtattgttc actatcccaa gcgacaccat caccatcgtc ttcctttctc    1320
ttaccaaagt aaataccctcc cactaattct ctgacaacaa cgaagtcagt acctttagca    1380
aattgtggct tgattggaga taagtctaaa agagagtcgg atgcaaagtt acatggtctt    1440
aagttggcgt acaattgaag ttctttacgg attttttagta aaccttgttc aggtctaaca    1500
ctaccggtac cccatttagg accagccaca gcacctaaca aaacggcatc aaccttcttg    1560
gaggcttcca gcgcctcatc tggaagtgga acacctgtag catcgatagc agcaccacca    1620
attaaatgat tttcgaaatc gaacttgaca ttggaacgaa catcagaaat agctttaaga    1680
accttaatgg cttcggctgt gatttcttga ccaacgtggt cacctggcaa acgacgatc    1740
ttcttagggg cagacattac aatggtatat ccttgaaata tatataaaaa aaggcgcctt    1800
agaccgctcg gccaaacaac caattacttg ttgagaaata gagtataatt atcctataaa    1860
tataacgttt ttgaacacac atgaacaagg aagtacagga caattgattt tgaagagaat    1920
gtggattttg atgtaattgt tgggattcca tttttaataa ggcaataata ttaggtatgt    1980
ggatatacta gaagttctcc tcgaccgtcg atatgcggtg tgaaataccg cacagatgcg    2040
taaggagaaa ataccgcatc aggaaattgt aaacgttaat attttgttaa aattcgcgtt    2100
aaattttgt aaatcagct catttttaa ccaataggcc gaaatcggca aaatccctta    2160
taaatcaaaa gaatagaccg agatagggtt gagtgttgtt ccagtttgga acaagagtcc    2220
actattaaag aacgtggact ccaacgtcaa agggcgaaaa accgtctatc agggcgatgg    2280
cccactacgt gaaccatcac cctaatcaag ttttttgggg tcgaggtgcc gtaaagcact    2340
```

```
aaatcggaac cctaaaggga gcccccgatt tagagcttga cggggaaagc cggcgaacgt    2400
ggcgagaaag gaagggaaga aagcgaaagg agcgggcgct agggcgctgg caagtgtagc    2460
ggtcacgctg cgcgtaacca ccacacccgc cgcgcttaat gcgccgctac agggcgcgtc    2520
gcgccattcg ccattcaggc tgcgcaactg ttgggaaggg cgatcggtgc gggcctcttc    2580
gctattacgc cagctgaatt ggagcgacct catgctatac ctgagaaagc aacctgacct    2640
acaggaaaga gttactcaag aataagaatt ttcgttttaa aacctaagag tcactttaaa    2700
atttgtatac acttattttt tttataactt atttaataat aaaaatcata aatcataaga    2760
aattcgctta tttagaagtg tcaacaacgt atctaccaac gatttgaccc ttttccatct    2820
tttcgtaaat ttctggcaag gtagacaagc cgacaacctt gattggagac ttgaccaaac    2880
ctctggcgaa gaattgttaa ttaagagctc agatcttatc gtcgtcatcc ttgtaatcca    2940
tcgatactag tgcggccgcc ctttagtgag ggttgaattc gaattttcaa aaattcttac    3000
tttttttttg gatggacgca aagaagttta ataatcatat tacatggcat taccaccata    3060
tacatatcca tatacatatc catatctaat cttacttata tgttgtggaa atgtaaagag    3120
ccccattatc ttagcctaaa aaaaccttct ctttggaact ttcagtaata cgcttaactg    3180
ctcattgcta tattgaagta cggattagaa gccgccgagc gggtgacagc cctccgaagg    3240
aagactctcc tccgtgcgtc ctcgtcttca ccggtcgcgt tcctgaaacg cagatgtgcc    3300
tcgcgccgca ctgctccgaa caataaagat tctacaatac tagcttttat ggttatgaag    3360
aggaaaaatt ggcagtaacc tggccccaca aaccttcaaa tgaacgaatc aaattaacaa    3420
ccataggatg ataatgcgat tagtttttta gccttatttc tggggtaatt aatcagcgaa    3480
gcgatgattt ttgatctatt aacagatata taaatgcaaa aactgcataa ccactttaac    3540
taatactttc aacattttcg gtttgtatta cttcttattc aaatgtaata aaagtatcaa    3600
caaaaaattg ttaatatacc tctatacttt aacgtcaagg agaaaaaacc ccggatccgt    3660
aatacgactc actatagggc ccgggcgtcg acatggaaca aagttgatt tccgaagaag    3720 acctcgagta agcttggtac cgcggctagc taagatccgc tctaaccgaa aaggaaggag    3780
ttagacaacc tgaagtctag gtccctattt atttttttat agttatgtta gtattaagaa    3840
cgttatttat atttcaaatt tttctttttt ttctgtacag acgcgtgtac gcatgtaaca    3900
ttatactgaa aaccttgctt gagaaggttt tgggacgctc aagatccag ctgcattaat    3960 gaatcggcca acgcgcgggg agaggcggtt tgcgtattgg gcgctcttcc gcttcctcgc    4020
tcactgactc gctgcgctcg tcgttcggc tgcggcgagc ggtatcagct cactcaaagg    4080
cggtaatacg gttatccaca gaatcagggg ataacgcagg aaagaacatg tgagcaaaag    4140
gccagcaaaa ggccaggaac cgtaaaaagg ccgcgttgct ggcgtttttc cataggctcc    4200
gcccccctga cgagcatcac aaaaatcgac gctcaagtca gaggtggcga aacccgacag    4260
gactataaag ataccaggcg tttccccctg gaagctccct cgtgcgctct cctgttccga    4320
ccctgccgct taccggatac ctgtccgcct ttctcccttc gggaagcgtg cgctttctc    4380 atagctcacg ctgtaggtat ctcagttcgg tgtaggtcgt tcgctccaag ctgggctgtg    4440
tgcacgaacc ccccgttcag cccgaccgct gcgccttatc cggtaactat cgtcttgagt    4500
ccaacccggt aagacacgac ttatcgccac tggcagcagc cactggtaac aggattagca    4560
gagcgaggta tgtaggcggt gctacagagt tcttgaagtg gtggcctaac tacggctaca    4620
ctagaaggac agtatttggt atctgcgctc tgctgaagcc agttaccttc ggaaaaagag    4680
ttggtagctc ttgatccggc aaacaaacca ccgctggtag cggtggtttt tttgtttgca    4740
```

| | |
|---|---|
| agcagcagat tacgcgcaga aaaaaaggat ctcaagaaga tcctttgatc ttttctacgg | 4800 |
| ggtctgacgc tcagtggaac gaaaactcac gttaagggat tttggtcatg agattatcaa | 4860 |
| aaaggatctt cacctagatc cttttaaatt aaaaatgaag ttttaaatca atctaaagta | 4920 |
| tatatgagta aacttggtct gacagttacc aatgcttaat cagtgaggca cctatctcag | 4980 |
| cgatctgtct atttcgttca tccatagttg cctgactccc cgtcgtgtag ataactacga | 5040 |
| tacgggaggg cttaccatct ggccccagtg ctgcaatgat accgcgagac ccacgctcac | 5100 |
| cggctccaga tttatcagca ataaaccagc cagccggaag ggccgagcgc agaagtggtc | 5160 |
| ctgcaacttt atccgcctcc atccagtcta ttaattgttg ccgggaagct agagtaagta | 5220 |
| gttcgccagt taatagtttg cgcaacgttg ttgccattgc tacaggcatc gtggtgtcac | 5280 |
| gctcgtcgtt tggtatggct tcattcagct ccggttccca acgatcaagg cgagttacat | 5340 |
| gatcccccat gttgtgcaaa aaagcggtta gctccttcgg tcctccgatc gttgtcagaa | 5400 |
| gtaagttggc cgcagtgtta tcactcatgg ttatggcagc actgcataat tctcttactg | 5460 |
| tcatgccatc cgtaagatgc ttttctgtga ctggtgagta ctcaaccaag tcattctgag | 5520 |
| aatagtgtat gcggcgaccg agttgctctt gcccggcgtc aatacgggat aataccgcgc | 5580 |
| cacatagcag aactttaaaa gtgctcatca ttggaaaacg ttcttcgggg cgaaaactct | 5640 |
| caaggatctt accgctgttg agatccagtt cgatgtaacc cactcgtgca cccaactgat | 5700 |
| cttcagcatc ttttactttc accagcgttt ctgggtgagc aaaaacagga aggcaaaatg | 5760 |
| ccgcaaaaaa gggaataagg gcgacacgga aatgttgaat actcatactc ttccttttc | 5820 |
| aatattattg aagcatttat cagggttatt gtctcatgag cggatacata tttgaatgta | 5880 |
| tttagaaaaa taaacaaata ggggttccgc gcacatttcc ccgaaaagtg ccacctgaac | 5940 |
| gaagcatctg tgcttcattt tgtagaacaa aaatgcaacg cgagagcgct aattttcaa | 6000 |
| acaaagaatc tgagctgcat ttttacagaa cagaaatgca acgcgaaagc gctattttac | 6060 |
| caacgaagaa tctgtgcttc attttgtaa acaaaaatg caacgcgaga gcgctaattt | 6120 |
| ttcaaacaaa gaatctgagc tgcatttta cagaacagaa atgcaacgcg agagcgctat | 6180 |
| tttaccaaca aagaatctat acttcttttt tgttctacaa aaatgcatcc cgagagcgct | 6240 |
| attttctaa caaagcatct tagattactt tttttctcct tgtgcgctc tataatgcag | 6300 |
| tctcttgata acttttgca ctgtaggtcc gttaaggtta gaagaaggct actttggtgt | 6360 |
| ctatttctc ttccataaaa aaagcctgac tccacttccc gcgtttactg attactagcg | 6420 |
| aagctgcggg tgcattttt caagataaag gcatccccga ttatattcta taccgatgtg | 6480 |
| gattgcgcat actttgtgaa cagaaagtga tagcgttgat gattcttcat tggtcagaaa | 6540 |
| attatgaacg gtttcttcta ttttgtctct atatactacg tataggaaat gtttacattt | 6600 |
| tcgtattgtt ttcgattcac tctatgaata gttcttacta caattttttt gtctaaagag | 6660 |
| taatactaga gataaacata aaaaatgtag aggtcgagtt tagatgcaag ttcaaggagc | 6720 |
| gaaaggtgga tgggtaggtt atataggat atagcacaga gatatatagc aaagagatac | 6780 |
| ttttgagcaa tgtttgtgga agcggtattc gcaatatttt agtagctcgt acagtccgg | 6840 |
| tgcgttttg gtttttgaa agtgcgtctt cagagcgctt ttggttttca aaagcgctct | 6900 |
| gaagttccta cttttctag agaataggaa cttcggaata ggaacttcaa agcgtttccg | 6960 |
| aaaacgagcg cttccgaaaa tgcaacgcga gctgcgcaca tacagctcac tgttcacgtc | 7020 |
| gcacctatat ctgcgtgttg cctgtatata tatacatg agaagaacgg catagtgcgt | 7080 |
| gtttatgctt aaatgcgtac ttatatgcgt ctatttatgt aggatgaaag gtagtctagt | 7140 |

-continued

```
acctcctgtg atattatccc attccatgcg gggtatcgta tgcttccttc agcactaccc    7200
tttagctgtt ctatatgctg ccactcctca attggattag tctcatcctt caatgctatc    7260
atttcctttg atattggatc atactaagaa accattatta tcatgacatt aacctataaa    7320
aataggcgta tcacgaggcc ctttcgtc                                        7348
```

<210> SEQ ID NO 11
<211> LENGTH: 49
<212> TYPE: DNA
<213> ORGANISM: Artificial Sequence
<220> FEATURE:
<223> OTHER INFORMATION: Primer 4-49 mvaA SpeI

<400> SEQUENCE: 11

```
gctactagta ggaggaaaac atcatgcaaa gtttagataa gaatttccg                49
```

<210> SEQ ID NO 12
<211> LENGTH: 39
<212> TYPE: DNA
<213> ORGANISM: Artificial Sequence
<220> FEATURE:
<223> OTHER INFORMATION: Primer 4-49 mvaAR XbaI

<400> SEQUENCE: 12

```
gcttctagac tattgttgtc taatttcttg taaaatgcg                            39
```

<210> SEQ ID NO 13
<211> LENGTH: 55
<212> TYPE: DNA
<213> ORGANISM: Artificial Sequence
<220> FEATURE:
<223> OTHER INFORMATION: Primer HMGS 5 prime Sa mvaS-S

<400> SEQUENCE: 13

```
gaactgaaga tctaggagga aagcaaaatg acaataggta tcgacaaaat aaact          55
```

<210> SEQ ID NO 14
<211> LENGTH: 52
<212> TYPE: DNA
<213> ORGANISM: Artificial Sequence
<220> FEATURE:
<223> OTHER INFORMATION: Primer HMGS 3 prime Sa mvaS-AS

<400> SEQUENCE: 14

```
ttgcatgatg ttttcctcct actagttact ctggtctgtg atattcgcga ac             52
```

<210> SEQ ID NO 15
<211> LENGTH: 45
<212> TYPE: DNA
<213> ORGANISM: Artificial Sequence
<220> FEATURE:
<223> OTHER INFORMATION: Primer 67-1A-C

<400> SEQUENCE: 15

```
acactcgagg aggaataaat gagttttgat attgccaaat acccg                     45
```

<210> SEQ ID NO 16
<211> LENGTH: 37
<212> TYPE: DNA
<213> ORGANISM: Artificial Sequence
<220> FEATURE:
<223> OTHER INFORMATION: Primer 67-1B-C

<400> SEQUENCE: 16

```
tgatggtacc ttatgccagc caggccttga ttttggc                              37
```

```
<210> SEQ ID NO 17
<211> LENGTH: 45
<212> TYPE: DNA
<213> ORGANISM: Artificial Sequence
<220> FEATURE:
<223> OTHER INFORMATION: Primer 67-1C-C

<400> SEQUENCE: 17
actaggtacc aggaggaata aatgaagcaa ctcaccattc tgggc            45

<210> SEQ ID NO 18
<211> LENGTH: 37
<212> TYPE: DNA
<213> ORGANISM: Artificial Sequence
<220> FEATURE:
<223> OTHER INFORMATION: Primer 67-1D-C

<400> SEQUENCE: 18
aattgatggg ccctcagctt gcgagacgca tcacctc                     37

<210> SEQ ID NO 19
<211> LENGTH: 45
<212> TYPE: DNA
<213> ORGANISM: Artificial Sequence
<220> FEATURE:
<223> OTHER INFORMATION: Primer 67-1E-C

<400> SEQUENCE: 19
cataaagggc ccaggaggaa taaatggcaa ccactcattt ggatg            45

<210> SEQ ID NO 20
<211> LENGTH: 40
<212> TYPE: DNA
<213> ORGANISM: Artificial Sequence
<220> FEATURE:
<223> OTHER INFORMATION: Primer 67-1F-C

<400> SEQUENCE: 20
tattgttcat atgttatgta ttctcctgat ggatggttcg                  40

<210> SEQ ID NO 21
<211> LENGTH: 45
<212> TYPE: DNA
<213> ORGANISM: Artificial Sequence
<220> FEATURE:
<223> OTHER INFORMATION: Primer 67-1G-C

<400> SEQUENCE: 21
aactaacaca tatgaggagg aataaatgcg gacacagtgg ccctc            45

<210> SEQ ID NO 22
<211> LENGTH: 38
<212> TYPE: DNA
<213> ORGANISM: Artificial Sequence
<220> FEATURE:
<223> OTHER INFORMATION: Primer 67-1H-C

<400> SEQUENCE: 22
tgttagttac gcgtttaaag catggctctg tgcaatgg                    38

<210> SEQ ID NO 23
<211> LENGTH: 45
<212> TYPE: DNA
<213> ORGANISM: Artificial Sequence
<220> FEATURE:
<223> OTHER INFORMATION: Primer 67-2A-C
```

```
<400> SEQUENCE: 23
acgggatcca ggaggaataa atgcgaattg dacacggttt tgacg            45

<210> SEQ ID NO 24
<211> LENGTH: 41
<212> TYPE: DNA
<213> ORGANISM: Artificial Sequence
<220> FEATURE:
<223> OTHER INFORMATION: Primer 67-2B-C

<400> SEQUENCE: 24
tttagttggg ccctcatttt gttgccttaa tgagtagcgc c               41

<210> SEQ ID NO 25
<211> LENGTH: 49
<212> TYPE: DNA
<213> ORGANISM: Artificial Sequence
<220> FEATURE:
<223> OTHER INFORMATION: Primer 67-2C-C

<400> SEQUENCE: 25
tactaagggc ccaggaggaa ataatgcata accaggctcc aattcaacg       49

<210> SEQ ID NO 26
<211> LENGTH: 40
<212> TYPE: DNA
<213> ORGANISM: Artificial Sequence
<220> FEATURE:
<223> OTHER INFORMATION: Primer 67-2D-C

<400> SEQUENCE: 26
tccgggtacc ttattttca acctgctgaa cgtcaattcg                  40

<210> SEQ ID NO 27
<211> LENGTH: 43
<212> TYPE: DNA
<213> ORGANISM: Artificial Sequence
<220> FEATURE:
<223> OTHER INFORMATION: Primer 67-2E-C

<400> SEQUENCE: 27
aacaggtacc aggaggaaat aatgcagatc ctgttggcca acc             43

<210> SEQ ID NO 28
<211> LENGTH: 45
<212> TYPE: DNA
<213> ORGANISM: Artificial Sequence
<220> FEATURE:
<223> OTHER INFORMATION: Primer 67-2F-C

<400> SEQUENCE: 28
tggatgaagt cgacttaatc gacttcacga atatcgacac gcagc           45

<210> SEQ ID NO 29
<211> LENGTH: 50
<212> TYPE: DNA
<213> ORGANISM: Artificial Sequence
<220> FEATURE:
<223> OTHER INFORMATION: Primer 67-2G-C

<400> SEQUENCE: 29
catcaagtcg acaggaggaa ataatgcaaa cggaacacgt cattttattg      50

<210> SEQ ID NO 30
<211> LENGTH: 40
<212> TYPE: DNA
```

```
<213> ORGANISM: Artificial Sequence
<220> FEATURE:
<223> OTHER INFORMATION: Primer 67-2H-C

<400> SEQUENCE: 30
taatgcaagc ttatttaagc tgggtaaatg cagataatcg                            40

<210> SEQ ID NO 31
<211> LENGTH: 44
<212> TYPE: DNA
<213> ORGANISM: Artificial Sequence
<220> FEATURE:
<223> OTHER INFORMATION: Primer 67-2I-C

<400> SEQUENCE: 31
cagtaaagct taggaggaaa taatggactt ccgcagcaa ctcg                        44

<210> SEQ ID NO 32
<211> LENGTH: 41
<212> TYPE: DNA
<213> ORGANISM: Artificial Sequence
<220> FEATURE:
<223> OTHER INFORMATION: Primer 67-2J-C

<400> SEQUENCE: 32
tagttccatg gttatttatt acgctggatg atgtagtccg c                          41

<210> SEQ ID NO 33
<211> LENGTH: 35
<212> TYPE: DNA
<213> ORGANISM: Artificial Sequence
<220> FEATURE:
<223> OTHER INFORMATION: Primer 9-156A

<400> SEQUENCE: 33
acatagacgt cgggaaagcg aggatctagg taggg                                 35

<210> SEQ ID NO 34
<211> LENGTH: 37
<212> TYPE: DNA
<213> ORGANISM: Artificial Sequence
<220> FEATURE:
<223> OTHER INFORMATION: Primer 9-156B

<400> SEQUENCE: 34
ttcccgctcg aggtggcgga ccatataggc agatcag                               37

<210> SEQ ID NO 35
<211> LENGTH: 30
<212> TYPE: DNA
<213> ORGANISM: Artificial Sequence
<220> FEATURE:
<223> OTHER INFORMATION: Primer 61-67-CPK001-G

<400> SEQUENCE: 35
gtttaaacta ctattagctg aattgccact                                       30

<210> SEQ ID NO 36
<211> LENGTH: 46
<212> TYPE: DNA
<213> ORGANISM: Artificial Sequence
<220> FEATURE:
<223> OTHER INFORMATION: Primer 61-67-CPK002-G

<400> SEQUENCE: 36
actgcaaagt acacatatat cccgggtgtc agctcttta gatcgg                      46
```

```
<210> SEQ ID NO 37
<211> LENGTH: 46
<212> TYPE: DNA
<213> ORGANISM: Artificial Sequence
<220> FEATURE:
<223> OTHER INFORMATION: Primer 61-67-CPK003-G

<400> SEQUENCE: 37
ccgatctaaa agagctgaca cccgggatat atgtgtactt tgcagt          46

<210> SEQ ID NO 38
<211> LENGTH: 30
<212> TYPE: DNA
<213> ORGANISM: Artificial Sequence
<220> FEATURE:
<223> OTHER INFORMATION: Primer 61-67-CPK004-G

<400> SEQUENCE: 38
gtttaaacgg cgtcagtcca ccagctaaca                            30

<210> SEQ ID NO 39
<211> LENGTH: 30
<212> TYPE: DNA
<213> ORGANISM: Artificial Sequence
<220> FEATURE:
<223> OTHER INFORMATION: Primer 61-67-CPK005-G

<400> SEQUENCE: 39
gtttaaactt gctaaattcg agtgaaacac                            30

<210> SEQ ID NO 40
<211> LENGTH: 46
<212> TYPE: DNA
<213> ORGANISM: Artificial Sequence
<220> FEATURE:
<223> OTHER INFORMATION: Primer 61-67-CPK006-G

<400> SEQUENCE: 40
aaagatgaat tgaaaagctt cccgggtatg gaccctgaaa ccacag          46

<210> SEQ ID NO 41
<211> LENGTH: 46
<212> TYPE: DNA
<213> ORGANISM: Artificial Sequence
<220> FEATURE:
<223> OTHER INFORMATION: Primer 61-67-CPK007-G

<400> SEQUENCE: 41
ctgtggtttc agggtccata cccgggaagc ttttcaattc atcttt          46

<210> SEQ ID NO 42
<211> LENGTH: 30
<212> TYPE: DNA
<213> ORGANISM: Artificial Sequence
<220> FEATURE:
<223> OTHER INFORMATION: Primer 61-67-CPK008-G

<400> SEQUENCE: 42
gtttaaaccc aacaataata atgtcagatc                            30

<210> SEQ ID NO 43
<211> LENGTH: 30
<212> TYPE: DNA
<213> ORGANISM: Artificial Sequence
<220> FEATURE:
<223> OTHER INFORMATION: Primer 61-67-CPK009-G
```

```
<400> SEQUENCE: 43
gtttaaacta ctcagtatat taagtttcga                                      30

<210> SEQ ID NO 44
<211> LENGTH: 70
<212> TYPE: DNA
<213> ORGANISM: Artificial Sequence
<220> FEATURE:
<223> OTHER INFORMATION: Primer 61-67-CPK010-G

<400> SEQUENCE: 44
atctctcgca agagtcagac tgactcccgg gcgtgaataa gcttcgggtg acccttatgg     60
cattcttttt                                                            70

<210> SEQ ID NO 45
<211> LENGTH: 70
<212> TYPE: DNA
<213> ORGANISM: Artificial Sequence
<220> FEATURE:
<223> OTHER INFORMATION: Primer 61-67-CPK011-G

<400> SEQUENCE: 45
aaaaagaatg ccataagggt cacccgaagc ttattcacgc ccgggagtca gtctgactct     60
tgcgagagat                                                            70

<210> SEQ ID NO 46
<211> LENGTH: 30
<212> TYPE: DNA
<213> ORGANISM: Artificial Sequence
<220> FEATURE:
<223> OTHER INFORMATION: Primer 61-67-CPK012-G

<400> SEQUENCE: 46
gtttaaacaa tttagtgtct gcgatgatga                                      30

<210> SEQ ID NO 47
<211> LENGTH: 30
<212> TYPE: DNA
<213> ORGANISM: Artificial Sequence
<220> FEATURE:
<223> OTHER INFORMATION: Primer 61-67-CPK013-G

<400> SEQUENCE: 47
gtttaaacta ttgtgagggt cagttatttc                                      30

<210> SEQ ID NO 48
<211> LENGTH: 44
<212> TYPE: DNA
<213> ORGANISM: Artificial Sequence
<220> FEATURE:
<223> OTHER INFORMATION: Primer 61-67-CPK014alt-G

<400> SEQUENCE: 48
gcggggacga ggcaagctaa actttagtat attcttcgaa gaaa                      44

<210> SEQ ID NO 49
<211> LENGTH: 44
<212> TYPE: DNA
<213> ORGANISM: Artificial Sequence
<220> FEATURE:
<223> OTHER INFORMATION: Primer 61-67-CPK015alt-G

<400> SEQUENCE: 49
tttcttcgaa gaatatacta agtttagct tgcctcgtcc ccgc                       44
```

<210> SEQ ID NO 50
<211> LENGTH: 60
<212> TYPE: DNA
<213> ORGANISM: Artificial Sequence
<220> FEATURE:
<223> OTHER INFORMATION: Primer 61-67-CPK016-G

<400> SEQUENCE: 50
caatcaacgt ggagggtaat tctgctagcc tctcccgggt ggatggcggc gttagtatcg    60

<210> SEQ ID NO 51
<211> LENGTH: 60
<212> TYPE: DNA
<213> ORGANISM: Artificial Sequence
<220> FEATURE:
<223> OTHER INFORMATION: Primer 61-67-CPK017-G

<400> SEQUENCE: 51
cgatactaac gccgccatcc acccgggaga ggctagcaga attaccctcc acgttgattg    60

<210> SEQ ID NO 52
<211> LENGTH: 30
<212> TYPE: DNA
<213> ORGANISM: Artificial Sequence
<220> FEATURE:
<223> OTHER INFORMATION: Primer 61-67-CPK018-G

<400> SEQUENCE: 52
gtttaaacgc cgccgttgtt gttattgtag    30

<210> SEQ ID NO 53
<211> LENGTH: 30
<212> TYPE: DNA
<213> ORGANISM: Artificial Sequence
<220> FEATURE:
<223> OTHER INFORMATION: Primer 61-67-CPK019-G

<400> SEQUENCE: 53
gtttaaactt ttccaatagg tggttagcaa    30

<210> SEQ ID NO 54
<211> LENGTH: 55
<212> TYPE: DNA
<213> ORGANISM: Artificial Sequence
<220> FEATURE:
<223> OTHER INFORMATION: Primer 61-67-CPK020-G

<400> SEQUENCE: 54
gggtgacccg gcggggacga ggcaagctaa acgtcttcct ttctcttacc aaagt    55

<210> SEQ ID NO 55
<211> LENGTH: 55
<212> TYPE: DNA
<213> ORGANISM: Artificial Sequence
<220> FEATURE:
<223> OTHER INFORMATION: Primer 61-67-CPK021-G

<400> SEQUENCE: 55
actttggtaa gagaaaggaa gacgtttagc ttgcctcgtc cccgccgggt caccc    55

<210> SEQ ID NO 56
<211> LENGTH: 62
<212> TYPE: DNA
<213> ORGANISM: Artificial Sequence
<220> FEATURE:
<223> OTHER INFORMATION: Primer 61-67-CPK022-G -continued

<400> SEQUENCE: 56
aatatcataa aaaaagagaa tctttcccgg gtggatggcg gcgttagtat cgaatcgaca   60
gc   62

<210> SEQ ID NO 57
<211> LENGTH: 62
<212> TYPE: DNA
<213> ORGANISM: Artificial Sequence
<220> FEATURE:
<223> OTHER INFORMATION: Primer 61-67-CPK023-G

<400> SEQUENCE: 57
gctgtcgatt cgatactaac gccgccatcc acccgggaaa gattctcttt ttttatgata   60
tt   62

<210> SEQ ID NO 58
<211> LENGTH: 45
<212> TYPE: DNA
<213> ORGANISM: Artificial Sequence
<220> FEATURE:
<223> OTHER INFORMATION: Primer 61-67-CPK024-G

<400> SEQUENCE: 58
gtttaaacgt gttaacgttt ctttcgccta cgtggaagga gaatc   45

<210> SEQ ID NO 59
<211> LENGTH: 35
<212> TYPE: DNA
<213> ORGANISM: Artificial Sequence
<220> FEATURE:
<223> OTHER INFORMATION: Primer 61-67-CPK025-G

<400> SEQUENCE: 59 tcccccccggg ttaaaaaaaa tccttggact agtca   35

<210> SEQ ID NO 60
<211> LENGTH: 35
<212> TYPE: DNA
<213> ORGANISM: Artificial Sequence
<220> FEATURE:
<223> OTHER INFORMATION: Primer 61-67-CPK031-G

<400> SEQUENCE: 60 tcccccccggg agttatgaca attacaacaa cagaa   35

<210> SEQ ID NO 61
<211> LENGTH: 30
<212> TYPE: DNA
<213> ORGANISM: Artificial Sequence
<220> FEATURE:
<223> OTHER INFORMATION: Primer 61-67-CPK032-G

<400> SEQUENCE: 61 tcccccccggg tatatatata tcattgttat   30

<210> SEQ ID NO 62
<211> LENGTH: 30
<212> TYPE: DNA
<213> ORGANISM: Artificial Sequence
<220> FEATURE:
<223> OTHER INFORMATION: Primer 61-67-CPK035-G

<400> SEQUENCE: 62 tcccccccggg aaaagtaagt caaaaggcac   30

<210> SEQ ID NO 63
<211> LENGTH: 30
<212> TYPE: DNA
<213> ORGANISM: Artificial Sequence
<220> FEATURE:
<223> OTHER INFORMATION: Primer 61-67-CPK040-G

<400> SEQUENCE: 63 tcccccggg atggtctgct taaatttcat                              30

<210> SEQ ID NO 64
<211> LENGTH: 45
<212> TYPE: DNA
<213> ORGANISM: Artificial Sequence
<220> FEATURE:
<223> OTHER INFORMATION: Primer 61-67-CPK041-G

<400> SEQUENCE: 64 tcccccggg tagcttgtac ccattaaaag aattttatca tgccg             45

<210> SEQ ID NO 65
<211> LENGTH: 30
<212> TYPE: DNA
<213> ORGANISM: Artificial Sequence
<220> FEATURE:
<223> OTHER INFORMATION: Primer 61-67-CPK046-G

<400> SEQUENCE: 65 tcccccggg tttctcattc aagtggtaac                              30

<210> SEQ ID NO 66
<211> LENGTH: 30
<212> TYPE: DNA
<213> ORGANISM: Artificial Sequence
<220> FEATURE:
<223> OTHER INFORMATION: Primer 61-67-CPK047-G

<400> SEQUENCE: 66 tcccccggg taaataaaga aaataaagtt                              30

<210> SEQ ID NO 67
<211> LENGTH: 47
<212> TYPE: DNA
<213> ORGANISM: Artificial Sequence
<220> FEATURE:
<223> OTHER INFORMATION: Primer 61-67-CPK050-G

<400> SEQUENCE: 67
aatttttgaa aattcaatat aaatggcttc agaaaaagaa attagga          47

<210> SEQ ID NO 68
<211> LENGTH: 47
<212> TYPE: DNA
<213> ORGANISM: Artificial Sequence
<220> FEATURE:
<223> OTHER INFORMATION: Primer 61-67-CPK051-G

<400> SEQUENCE: 68
tcctaatttc tttttctgaa gccatttata ttgaattttc aaaaatt          47

<210> SEQ ID NO 69
<211> LENGTH: 51
<212> TYPE: DNA
<213> ORGANISM: Artificial Sequence
<220> FEATURE:
<223> OTHER INFORMATION: Primer 61-67-CPK052-G -continued

<400> SEQUENCE: 69
agttttcacc aattggtctg cagccattat agttttttct ccttgacgtt a        51

<210> SEQ ID NO 70
<211> LENGTH: 51
<212> TYPE: DNA
<213> ORGANISM: Artificial Sequence
<220> FEATURE:
<223> OTHER INFORMATION: Primer 61-67-CPK053-G

<400> SEQUENCE: 70
taacgtcaag gagaaaaaac tataatggct gcagaccaat tggtgaaaac t        51

<210> SEQ ID NO 71
<211> LENGTH: 47
<212> TYPE: DNA
<213> ORGANISM: Artificial Sequence
<220> FEATURE:
<223> OTHER INFORMATION: Primer 61-67-CPK054-G

<400> SEQUENCE: 71 aattttttgaa aattcaatat aaatgaaact ctcaactaaa ctttgtt            47

<210> SEQ ID NO 72
<211> LENGTH: 47
<212> TYPE: DNA
<213> ORGANISM: Artificial Sequence
<220> FEATURE:
<223> OTHER INFORMATION: Primer 61-67-CPK055-G

<400> SEQUENCE: 72
aacaaagttt agttgagagt ttcatttata ttgaattttc aaaaatt            47

<210> SEQ ID NO 73
<211> LENGTH: 47
<212> TYPE: DNA
<213> ORGANISM: Artificial Sequence
<220> FEATURE:
<223> OTHER INFORMATION: Primer 61-67-CPK056-G

<400> SEQUENCE: 73 aattttttgaa aattcaatat aaatgtctca gaacgtttac attgtat           47

<210> SEQ ID NO 74
<211> LENGTH: 47
<212> TYPE: DNA
<213> ORGANISM: Artificial Sequence
<220> FEATURE:
<223> OTHER INFORMATION: Primer 61-67-CPK057-G

<400> SEQUENCE: 74
atacaatgta aacgttctga gacatttata ttgaattttc aaaaatt            47

<210> SEQ ID NO 75
<211> LENGTH: 51
<212> TYPE: DNA
<213> ORGANISM: Artificial Sequence
<220> FEATURE:
<223> OTHER INFORMATION: Primer 61-67-CPK058-G

<400> SEQUENCE: 75
tgcagaagtt aagaacggta atgacattat agttttttct ccttgacgtt a        51

<210> SEQ ID NO 76
<211> LENGTH: 51
<212> TYPE: DNA

```
-continued

<213> ORGANISM: Artificial Sequence
<220> FEATURE:
<223> OTHER INFORMATION: Primer 61-67-CPK059-G

<400> SEQUENCE: 76
taacgtcaag gagaaaaaac tataatgtca ttaccgttct taacttctgc a        51

<210> SEQ ID NO 77
<211> LENGTH: 47
<212> TYPE: DNA
<213> ORGANISM: Artificial Sequence
<220> FEATURE:
<223> OTHER INFORMATION: Primer 61-67-CPK060-G

<400> SEQUENCE: 77
aatttttgaa aattcaatat aaatgtcaga gttgagagcc ttcagtg              47

<210> SEQ ID NO 78
<211> LENGTH: 47
<212> TYPE: DNA
<213> ORGANISM: Artificial Sequence
<220> FEATURE:
<223> OTHER INFORMATION: Primer 61-67-CPK061-G

<400> SEQUENCE: 78
cactgaaggc tctcaactct gacatttata ttgaattttc aaaaatt              47

<210> SEQ ID NO 79
<211> LENGTH: 51
<212> TYPE: DNA
<213> ORGANISM: Artificial Sequence
<220> FEATURE:
<223> OTHER INFORMATION: Primer 61-67-CPK062-G

<400> SEQUENCE: 79
ggtaacggat gctgtgtaaa cggtcattat agttttttct ccttgacgtt a        51

<210> SEQ ID NO 80
<211> LENGTH: 51
<212> TYPE: DNA
<213> ORGANISM: Artificial Sequence
<220> FEATURE:
<223> OTHER INFORMATION: Primer 61-67-CPK063-G

<400> SEQUENCE: 80
taacgtcaag gagaaaaaac tataatgacc gtttacacag catccgttac c        51

<210> SEQ ID NO 81
<211> LENGTH: 47
<212> TYPE: DNA
<213> ORGANISM: Artificial Sequence
<220> FEATURE:
<223> OTHER INFORMATION: Primer 61-67-CPK064-G

<400> SEQUENCE: 81
aatttttgaa aattcaatat aaatgactgc cgacaacaat agtatgc              47

<210> SEQ ID NO 82
<211> LENGTH: 47
<212> TYPE: DNA
<213> ORGANISM: Artificial Sequence
<220> FEATURE:
<223> OTHER INFORMATION: Primer 61-67-CPK065-G

<400> SEQUENCE: 82
gcatactatt gttgtcggca gtcatttata ttgaattttc aaaaatt              47
```

```
<210> SEQ ID NO 83
<211> LENGTH: 70
<212> TYPE: DNA
<213> ORGANISM: Artificial Sequence
<220> FEATURE:
<223> OTHER INFORMATION: Primer 61-67-CPK066-G

<400> SEQUENCE: 83
ggtaagacgg ttgggtttta tcttttgcag ttggtactat taagaacaat cacaggaaac      60
agctatgacc                                                            70

<210> SEQ ID NO 84
<211> LENGTH: 70
<212> TYPE: DNA
<213> ORGANISM: Artificial Sequence
<220> FEATURE:
<223> OTHER INFORMATION: Primer 61-67-CPK067-G

<400> SEQUENCE: 84
ttgcgttttg tactttggtt cgctcaattt tgcaggtaga taatcgaaaa gttgtaaaac      60
gacggccagt                                                            70

<210> SEQ ID NO 85
<211> LENGTH: 66
<212> TYPE: DNA
<213> ORGANISM: Artificial Sequence
<220> FEATURE:
<223> OTHER INFORMATION: Primer 50-56-pw100-G

<400> SEQUENCE: 85
gagtgaacct gctgcctggc gtgctctgac tcagtacatt tcatagtgga tggcggcgtt      60
agtatc                                                                66

<210> SEQ ID NO 86
<211> LENGTH: 65
<212> TYPE: DNA
<213> ORGANISM: Artificial Sequence
<220> FEATURE:
<223> OTHER INFORMATION: Primer 50-56-pw101-G

<400> SEQUENCE: 86
cgtgtatacg ttttccgctt ctgctcttcg tcttttctct tcttccgata tcacaactgt      60
tacga                                                                 65

<210> SEQ ID NO 87
<211> LENGTH: 21
<212> TYPE: DNA
<213> ORGANISM: Artificial Sequence
<220> FEATURE:
<223> OTHER INFORMATION: Primer PW-91-079-CPK373-G

<400> SEQUENCE: 87
tcgactacgt cgtaaggccg t                                               21

<210> SEQ ID NO 88
<211> LENGTH: 42
<212> TYPE: DNA
<213> ORGANISM: Artificial Sequence
<220> FEATURE:
<223> OTHER INFORMATION: Primer PW-91-079-CPK374-G

<400> SEQUENCE: 88
gcatctgtgc ggtatttcac tatatatatt tcaaggatat ac                        42
```

```
<210> SEQ ID NO 89
<211> LENGTH: 25
<212> TYPE: DNA
<213> ORGANISM: Artificial Sequence
<220> FEATURE:
<223> OTHER INFORMATION: Primer PW-91-079-CPK376-G

<400> SEQUENCE: 89
tatggtgcac tctcagtaca atctg                                             25

<210> SEQ ID NO 90
<211> LENGTH: 42
<212> TYPE: DNA
<213> ORGANISM: Artificial Sequence
<220> FEATURE:
<223> OTHER INFORMATION: Primer PW-91-079-CPK375-G

<400> SEQUENCE: 90
gtatatcctt gaaatatata tagtgaaata ccgcacagat gc                          42
```

JET FUEL COMPOSITIONS AND METHODS OF MAKING AND USING SAME

PRIOR RELATED APPLICATIONS

This application claims the benefit under 35 U.S.C. §119 (e) of U.S. Provisional Patent Application Nos. 60/860,853, filed Nov. 21, 2006, and 60/951,235, filed Jul. 23, 2007, all of which are incorporated herein by reference in their entireties.

FIELD OF THE INVENTION

Provided herein are, among other things, jet fuel compositions and methods of making and using the same. In some embodiments, the fuel compositions comprise at least a fuel component readily and efficiently produced, at least in part, from a microorganism. In certain embodiments, the fuel compositions provided herein comprise a bioengineered fuel component. In further embodiments, the fuel compositions provided herein comprise carane, pinane, sabinane or a combination thereof.

BACKGROUND OF THE INVENTION

Biofuel is generally a fuel derived from biomass, i.e., recently living organisms or their metabolic byproducts, such as manure from animals. Biofuel is desirable because it is a renewable energy source, unlike other natural resources such as petroleum, coal and nuclear fuels. A biofuel that is suitable for use as jet fuel has yet to be introduced. Therefore, there is a need for biofuels for jet engines. The present invention provides such biofuels.

SUMMARY OF THE INVENTION

Provided herein are, among other things, fuel compositions comprising $C_{10}$ bicyclic isoprenoids and methods of making and using the same. These compounds can display a good balance of physical properties for making excellent jet or missile fuels. In certain embodiments, $C_{10}$ bicyclic isoprenoids are readily and efficiently produced, at least in part, from a microorganism.

In one aspect, provided herein are fuel compositions comprising (a) a $C_{10}$ bicyclic isoprenoid in an amount that is at least 2% by volume, based on the total volume of the fuel composition; and (b) a petroleum-based fuel in an amount that is at least 5% by volume, based on the total volume of the fuel composition. In some embodiments, the fuel composition has a flash point equal to or greater than 38° C. In further embodiments, the fuel composition has a density at 15° C. from about 750 kg/m³ to about 850 kg/m³.

In another aspect, provided herein are fuel compositions comprising (a) a $C_{10}$ bicyclic isoprenoid in an amount that is at least 10% by volume, based on the total volume of the fuel composition; and (b) kerosene in an amount that is at least 40% by volume, based on the total volume of the fuel composition. In some embodiments, the fuel composition has a density at 15° C. from about 750 kg/m³ to about 840 kg/m³. In further embodiments, the fuel composition has a flash point equal to or greater than 38° C. In still further embodiments, the fuel composition has a freezing point lower than −40° C.

In another aspect, provided herein are methods of making fuel compositions comprising the steps of (a) contacting a $C_{10}$ isoprenoid starting material with hydrogen in the presence of a catalyst to form a $C_{10}$ bicyclic isoprenoid; and (b) mixing the $C_{10}$ bicyclic isoprenoid with a fuel component to make the

2 fuel composition. In certain embodiments, the $C_{10}$ isoprenoid starting material is carene, α-pinene, β-pinene, sabinene or a combination thereof.

In another aspect, provided herein are methods of making fuel compositions from a simple sugar comprising the steps of (a) contacting a cell capable of making a $C_{10}$ isoprenoid starting material with the simple sugar under conditions suitable for making the $C_{10}$ isoprenoid starting material; (b) converting the $C_{10}$ isoprenoid starting material to a $C_{10}$ bicyclic isoprenoid; and (c) mixing the $C_{10}$ bicyclic isoprenoid with a fuel component to make the fuel composition. In certain embodiments, the $C_{10}$ isoprenoid starting material is carene, α-pinene, β-pinene, sabinene or a combination thereof.

In another aspect, provided herein are vehicles comprising an internal combustion engine; a fuel tank connected to the internal combustion engine; and a fuel composition disclosed herein in the fuel tank, wherein the fuel composition is used to power the internal combustion engine. In some embodiments, the internal combustion engine is a jet engine.

In another aspect, provided herein are methods of powering an engine comprising the step of combusting one or more of the fuel compositions disclosed herein. In certain embodiments, the engine is a jet engine.

In some embodiments, the $C_{10}$ bicyclic isoprenoid in the fuel compositions disclosed herein is or comprises carane, pinane, sabinane or a combination thereof.

In certain embodiments, the petroleum-based fuel in the fuel compositions disclosed herein is kerosene, Jet A, Jet A-1, Jet B, or a combination thereof. In other embodiments, the fuel compositions disclosed herein meet the ASTM D 1655 specification for Jet A, Jet A-1 or Jet B.

DESCRIPTION OF THE DRAWINGS

FIG. 8 shows the ASTM D 1655 test data for certain embodiments of the fuel compositions disclosed herein.

DEFINITIONS

Figure 1:
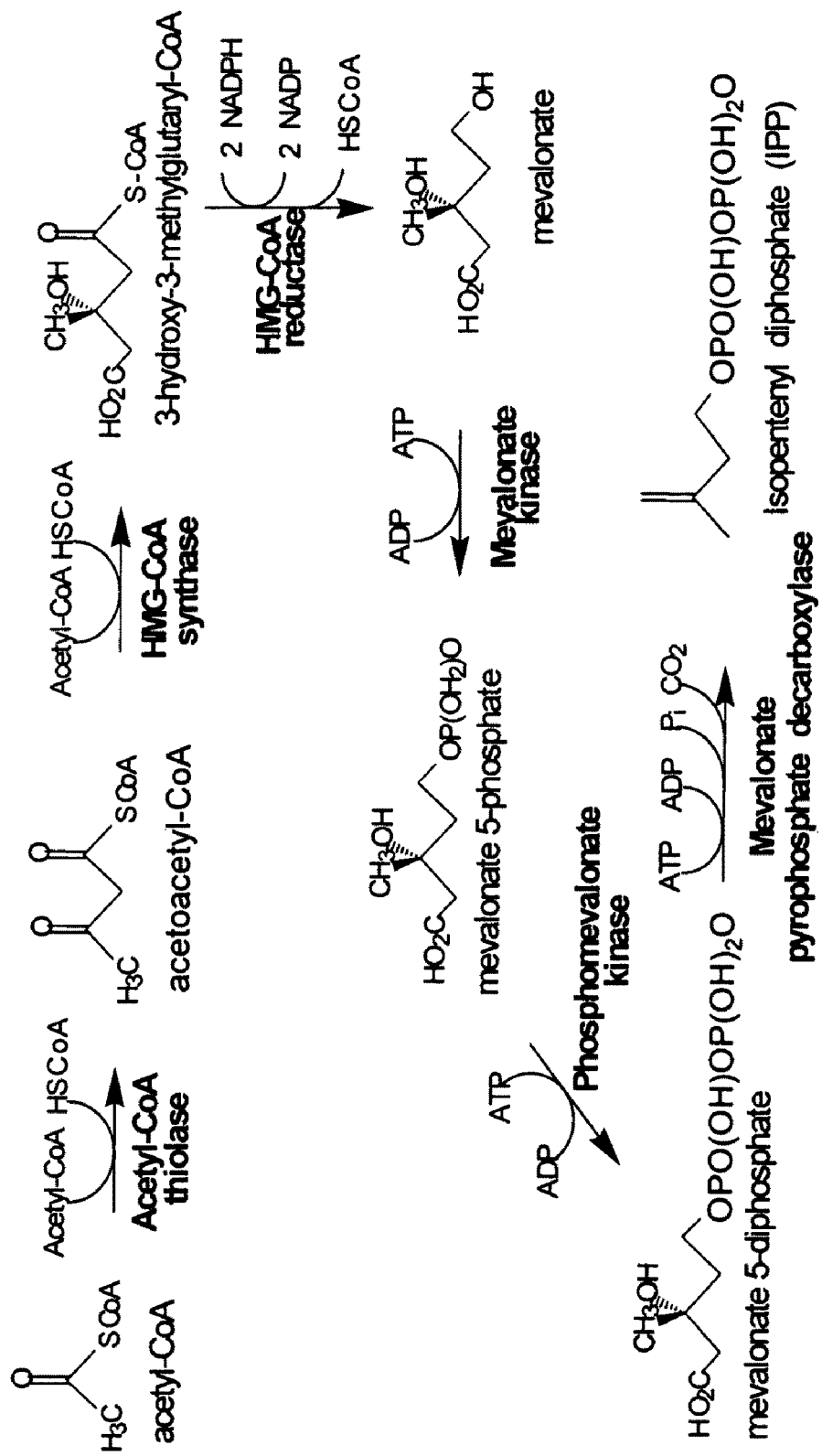
FIG. 1 is a schematic representation of the mevalonate ("MEV") pathway for the production of isopentenyl diphosphate ("IPP").

The ASTM D 1655 specifications, published by ASTM International, set certain minimum acceptance requirements for Jet A, Jet A-1, and Jet B.

"Bioengineered compound" refers to a compound made by a host cell, including any archae, bacterial, or eukaryotic cells or microorganism.

"Biofuel" refers to any fuel that is derived from a biomass, i.e., recently living organisms or their metabolic byproducts, such as manure from cows. It is a renewable energy source, unlike other natural resources such as petroleum, coal and nuclear fuels.

"Carane" refers to the following compound

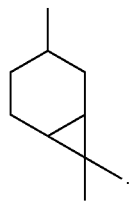

"$C_{10}$ bicyclic isoprenoid" refers to a fully saturated isoprenoid compound consisting of 10 carbon atoms and that includes two cyclic moieties. In certain embodiments, the $C_{10}$ bicyclic isoprenoid is selected from the group consisting of carane (i.e., 3,7,7-trimethyl-bicyclo[4.1.0]heptane; CAS No. 554-59-6), pinane (i.e., 2,6,6-trimethyl-bicyclo[3.1.1]heptane; CAS No. 473-55-2), and sabinane (i.e., 4-methyl-1-(1-methylethyl)bicyclo[3.1.0]hexane; CAS No. 471-12-5) and combinations thereof.

"$C_{10}$ isoprenoid starting material" refers to geranyl pyrophosphate ("GPP") or a compound that is capable of being derived from GPP.

"Density" refers to a measure of mass per volume at a particular temperature. The generally accepted method for measuring the density of a fuel is ASTM Standard D 4052, which is incorporated herein by reference.

"Doctor Test" is for the detection of mercaptans in petroleum-based fuels such as jet fuel and kerosene. This test may also provide information on hydrogen sulfide and elemental sulfur that may be present in the fuels. The generally accepted method for measuring the freezing point of a fuel is ASTM Standard D 4952, which is incorporated herein by reference.

"Flash point" refers to the lowest temperature at which the vapors above a flammable liquid will ignite in the air on the application of an ignition source. Generally, every flammable liquid has a vapor pressure, which is a function of the temperature of the liquid. As the temperature increases, the vapor pressure of the liquid increases. As the vapor pressure increases, the concentration of the evaporated liquid in the air increases. At the flash point temperature, just enough amount of the liquid has vaporized to bring the vapor-air space over the liquid above the lower flammability limit. For example, the flash point of gasoline is about −43° C. which is why gasoline is so highly flammable. For safety reasons, it is desirable to have much higher flash points for fuel that is contemplated for use in jet engines. The generally accepted methods for measuring the flash point of a fuel are ASTM Standard D 56, ASTM Standard D 93, ASTM Standard D 3828-98, all of which are incorporated herein by reference.

"Freezing point" refers to the temperature at which the last wax crystal melts, when warming a fuel that has been previously been cooled until waxy crystals form. The generally accepted method for measuring the freezing point of a fuel is ASTM Standard D 2386, which is incorporated herein by reference.

"Fuel" refers to one or more hydrocarbons, one or more alcohols, one or more fatty esters or a mixture thereof. Preferably, liquid hydrocarbons are used. Fuel can be used to power internal combustion engines such as reciprocating engines (e.g., gasoline engines and diesel engines), Wankel engines, jet engines, some rocket engines, missile engines and gas turbine engines. In some embodiments, fuel typically comprises a mixture of hydrocarbons such as alkanes, cycloalkanes and aromatic hydrocarbons. In other embodiments, the fuel comprises a $C_{10}$ bicyclic isoprenoid. In still other embodiments, fuel comprises carane, pinane, and sabinane either individually or as mixtures thereof.

"Fuel additive" refers to amino fuel component such as chemical components added to fuels to alter the properties of the fuel, e.g., to improve engine performance, fuel handling, fuel stability, or for contaminant control. Types of additives include, but are not limited to, antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides and combinations thereof. The term "conventional additives" refers to fuel additives known to skilled artisan, such as those described above, and does not include a $C_{10}$ bicyclic isoprenoid.

"Fuel component" refers to any compound or a mixture of compounds that are used to formulate a fuel composition. There are "major fuel components" and "minor fuel components." A major fuel component is present in a fuel composition by at least 50% by volume; and a minor fuel component is present in a fuel composition by less than 50%. Fuel additives are minor fuel components. A $C_{10}$ bicyclic isoprenoid can be a major component or a minor component, or in a mixture with other fuel components.

"Fuel composition" refers to a fuel that comprises at least two fuel components.

"Isoprenoid" and "isoprenoid compound" are used interchangeably herein and refer to a compound derivable from isopentenyl diphosphate ("IPP").

"Jet fuel" refers to a fuel suitable for use in a jet engine.

"Kerosene" refers to a specific fractional distillate of petroleum (also known as "crude oil"), generally between about 150° C. and about 275° C. at atmospheric pressure. Crude oils are composed primarily of hydrocarbons of the paraffinic, naphthenic, and aromatic classes.

"Missile fuel" refers to a fuel suitable for use in a missile engine.

"p-Cymene" refers to the following compound

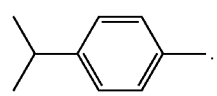

"Pinane" refers to the following compound

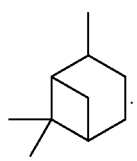

"Petroleum-based fuel" refers to a fuel that includes a fractional distillate of petroleum.

"Sabinane" refers to the following compound

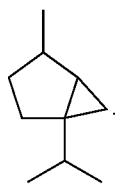

"Smoke Point" refers to the point in which a fuel or fuel composition is heated until it breaks down and smokes. The generally accepted method for measuring the smoke point of a fuel is ASTM Standard D 1322, which is incorporated herein by reference.

"Viscosity" refers to a measure of the resistance of a fuel or fuel composition to deform under shear stress. The generally accepted method for measuring the viscosity of a fuel is ASTM Standard D 445, which is incorporated herein by reference.

As used herein, a composition that is a "substantially pure" compound is substantially free of one or more other compounds, i.e., the composition contains greater than 80 vol. %, greater than 90 vol. %, greater than 95 vol. %, greater than 96 vol. %, greater than 97 vol. %, greater than 98 vol. %, greater than 99 vol. %, greater than 99.5 vol. %, greater than 99.6 vol. %, greater than 99.7 vol. %, greater than 99.8 vol. %, or greater than 99.9 vol. % of the compound; or less than 20 vol. %, less than 10 vol. %, less than 5 vol. %, less than 3 vol. %, less than 1 vol. %, less than 0.5 vol. %, less than 0.1 vol. %, or less than 0.01 vol. % of the one or more other compounds, based on the total volume of the composition.

As used herein, a composition that is "substantially free" of a compound means that the composition contains less than 20 vol. %, less than 10 vol. %, less than 5 vol. %, less than 4 vol. %, less than 3 vol. %, less than 2 vol. %, less than 1 vol. %, less than 0.5 vol. %, less than 0.1 vol. %, or less than 0.01 vol. % of the compound, based on the total volume of the composition.

As used herein, the term "stereochemically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein, the term "enantiomerically pure" means a stereomerically pure composition of a compound having one chiral center.

As used herein, the term "racemic" or "racemate" means about 50% of one enantiomer and about 50% of the corresponding enantiomer relative to all chiral centers in the molecule. The invention encompasses all enantiomerically pure, enantiomerically enriched, diastereomerically pure, diastereomerically enriched, and racemic mixtures of the compounds of the invention.

In addition to the definitions above, certain compounds described herein have one or more double bonds that can exist as either the Z or E isomer. In certain embodiments, compounds described herein are present as individual isomers substantially free of other isomers and alternatively, as mixtures of various isomers, e.g., racemic mixtures of stereoisomers.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, RL and an upper limit, RU, is disclosed, any number falling within the range is specifically disclosed. In particular, the following numbers within the range are specifically disclosed: R=RL+k*(RU−RL), wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

DESCRIPTION OF EMBODIMENTS OF THE INVENTION

In one aspect, the invention provides a fuel composition comprising:
(a) a $C_{10}$ bicyclic isoprenoid in an amount that is at least 2% by volume, based on the total volume of the fuel composition; and
(b) a petroleum-based fuel in an amount that is at least 5% by volume, based on the total volume of the fuel composition,
wherein the fuel composition has a flash point equal to or greater than 38° C. and the fuel composition has a density at 15° C. from about 750 kg/m³ to about 850 kg/m³.

In some embodiments, the $C_{10}$ bicyclic isoprenoid is carane. In other embodiments, the $C_{10}$ bicyclic isoprenoid is pinane. In still other embodiments, the $C_{10}$ bicyclic isoprenoid is sabinane. In certain embodiments, the $C_{10}$ bicyclic isoprenoid is a mixture comprising two or more of carane, pinane, and sabinane.

In certain embodiments where the $C_{10}$ bicyclic isoprenoid is pinane, the fuel composition comprises from about 0% to about 10% of a hydrogenated naphthalene-containing material. In certain other embodiments, the fuel composition does not comprise a hydrogenated naphthalene-containing material. In further embodiments, the fuel composition has a final boiling point that is less than or equal to 300° C.

Each of the isoprenoid compounds in the fuel compositions can function as a fuel component which can release energy when it chemically reacts with an oxidant such as oxygen; or a fuel additive which can alter the performance or properties of the fuel component. In some embodiments, the isoprenoid compound is present in an amount of at least about 2%, at least about 3%, at least about 5%, at least about 10%, at least about 15%, at least about 30%, at least about 40%, at least about 50%, at least about 60%, at least about 70%, at least about 80%, or at least about 90%, based on the total weight or volume of the fuel composition. In other embodiments, the isoprenoid compound is present in an amount of at most about 5%, at most about 10%, at most about 15%, at most about 20%, at most about 25%, at most about 30%, at most about 35%, at most about 40%, at most about 45%, at most about 50%, at most about 60%, at most about 70%, at most about 80%, or at most about 90%, based on the total weight or volume of the fuel composition. In further embodiments, the isoprenoid compound is present in an amount from about 2% to about 99%, from about 2.5% to about 95%, from about 5% to about 90%, from about 7.5% to about 85%, from about 10% to about 80%, from about 15% to about 80%, from about 20% to about 75%, or from about 25% to about 75%, based on the total weight or volume of the fuel composition.

In some embodiments, the $C_{10}$ isoprenoid compound is derived from a bioengineered $C_{10}$ isoprenoid starting material. In certain embodiments, the bioengineered $C_{10}$ isoprenoid starting material is made by host cells by converting a carbon source into the $C_{10}$ isoprenoid starting material.

In other embodiments, the carbon source is a sugar such as a monosaccharide (simple sugar), a disaccharide, or one or more combinations thereof. In certain embodiments, the sugar is a simple sugar capable of supporting the growth of one or more of the cells provided herein. The simple sugar can be any simple sugar known to those of skill in the art. Some non-limiting examples of suitable simple sugars or monosaccharides include glucose, galactose, mannose, fructose, ribose, and combinations thereof. Some non-limiting examples of suitable disaccharides include sucrose, lactose, maltose, trehalose, cellobiose, and combinations thereof.

In other embodiments, the carbon source is a polysaccharide. Some non-limiting examples of suitable polysaccharides include starch, glycogen, cellulose, chitin, and combinations thereof.

In still other embodiments, the carbon source is a non-fermentable carbon source. Some non-limiting examples of suitable non-fermentable carbon source include acetate and glycerol.

In other embodiments, the amount of the petroleum-based fuel in the fuel compositions disclosed herein is at least about 20% and the amount of isoprenoid compound is from about 5% to about 75%, based on the total volume of the fuel composition. In certain embodiments, the amount of petroleum-based fuel is at least 30% and the amount of the isoprenoid compound is from about 5% to about 65%, based on the total volume of the fuel composition. In certain other embodiments, the amount of petroleum-based fuel is at least 40% and the amount of isoprenoid is from about 5% to about 50%, based on the total volume of the fuel composition. In certain other embodiments, the amount of petroleum-based fuel is at least 50% and the amount of isoprenoid is from about 5% to about 45%, based on the total volume of the fuel composition.

In some embodiments, the petroleum-based fuel is kerosene. Conventional kerosene generally is a mixture of hydrocarbons, having a boiling point from about 285° F. to about 610° F. (i.e., from about 140° C. to about 320° C.).

In other embodiments, the petroleum-based fuel is a jet fuel. Any jet fuel known to skilled artisans can be used herein. The American Society for Testing and Materials ("ASTM") and the United Kingdom Ministry of Defense ("MOD") have taken the lead roles in setting and maintaining specification for civilian aviation turbine fuel or jet fuel. The respective specifications issued by these two organizations are very similar but not identical. Many other countries issue their own national specifications for jet fuel but are very nearly or completely identical to either the ASTM or MOD specification. ASTM D 1655 is the Standard Specification for Aviation Turbine Fuels and includes specifications for Jet A, Jet A-1 and Jet B fuels. Defense Standard 91-91 is the MOD specification for Jet A-1.

Jet A-1 is the most common jet fuel and is produced to an internationally standardized set of specifications. In the United States only, a version of Jet A-1 known as Jet A is also used. Another jet fuel that is commonly used in civilian aviation is called Jet B. Jet B is a lighter fuel in the naptha-kerosene region that is used for its enhanced cold-weather performance. Jet A, Jet A-1 and Jet B are specified in ASTM Specification D 1655.

Alternatively, jet fuels are classified by militaries around the world with a different system of JP numbers. Some are almost identical to their civilian counterparts and differ only by the amounts of a few additives. For example, Jet A-1 is similar to JP-8 and Jet B is similar to JP-4.

In some embodiments, the fuel compositions provided herein further comprise an aromatic compound such as p-cymene, m-cymene or o-cymene. In further embodiments, the aromatic compound is or comprises p-cymene. In certain embodiments, the amount of p-cymene is from about 0.1% to about 50% by volume, from about 0.1% to about 45% by volume, from about 0.1% to about 40% by volume, or from about 0.1% to about 35% by volume, based on the total volume of the fuel composition. In other embodiments, the amount of p-cymene is from about 0.5% to about 35% by volume, based on the total volume of the fuel composition. In still other embodiments, the amount of p-cymene is from about 1% to about 25%, from about 5% to about 25%, from about 5% to about 20%, or 10% to about 20% by volume, based on the total volume of the fuel composition.

In some embodiments, the total amount of aromatic compounds in the fuel compositions is from about 1% to about 50% by weight or volume, based on the total weight or volume of the fuel composition. In other embodiments, the total amount of aromatic compounds in the fuel compositions is from about 15% to about 35% by weight or volume, based on the total weight or volume of the fuel compositions. In further embodiments, the total amount of aromatic compounds in the fuel compositions is from about 15% to about 25% by weight or volume, based on the total weight or volume of the fuel compositions. In other embodiments, the total amount of aromatic compounds in the fuel compositions is from about 5% to about 10% by weight or volume, based on the total weight or volume of the fuel compositions. In still further embodiments, the total amount of aromatic compounds in the fuel compositions is less than about 25% by weight or volume, based on the total weight or volume of the fuel compositions.

In some embodiments, the fuel composition further comprises a fuel additive. In certain embodiments, the fuel additive is from about 0.1% to about 50% by weight or volume, based on the total weight or volume of the fuel composition. In further embodiments, the fuel additive is selected from the group consisting of oxygenates, antioxidants, thermal stability improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, de-emulsifiers, dyes, markers, static dissipaters, biocides and combinations thereof.

The amount of a fuel additive in the fuel composition disclosed herein may be from about 0.1% to less than about 50%, from about 0.2% to about 40%, from about 0.3% to about 30%, from about 0.4% to about 20%, from about 0.5% to about 15% or from about 0.5% to about 10%, based on the total amount of the fuel composition. In certain embodiments, the amount of a fuel additive is less than about 50%, less than about 45%, less than about 40%, less than about 35%, less than about 30%, less than about 25%, less than about 20%, less than about 15%, less than about 10%, less than about 5%, less than about 4%, less than about 3%, less than about 2%, less than about 1% or less than about 0.5%, based on the total amount of the fuel composition. In some embodiments, the amount is in wt. % based on the total weight of the fuel composition. In other embodiments, the amount is in vol. % based on the total volume of the fuel composition.

Illustrative examples of fuel additives are described in greater detail below. Lubricity improvers are one example. In certain additives, the concentration of the lubricity improver in the fuel falls in the range from about 1 ppm to about 50,000 ppm, preferably from about 10 ppm to about 20,000 ppm, and more preferably from about 25 ppm to about 10,000 ppm. Some non-limiting examples of lubricity improver include esters of fatty acids.

Stabilizers improve the storage stability of the fuel composition. Some non-limiting examples of stabilizers include tertiary alkyl primary amines. The stabilizer may be present in the fuel composition at a concentration from about 0.001 wt. % to about 2 wt. %, based on the total weight of the fuel composition, and in one embodiment from about 0.01 wt. % to about 1 wt. %.

Combustion improvers increase the mass burning rate of the fuel composition. Some non-limiting examples of combustion improvers include ferrocene(dicyclopentadienyl iron), iron-based combustion improvers (e.g., TURBOTECT™ ER-18 from Turbotect (USA) Inc., Tomball, Tex.), barium-based combustion improvers, cerium-based combustion improvers, and iron and magnesium-based combustion improvers (e.g., TURBOTECT™ 703 from Turbotect (USA) Inc., Tomball, Tex.). The combustion improver may be present in the fuel composition at a concentration from about 0.001 wt. % to about 1 wt. %, based on the total weight of the fuel composition, and in one embodiment from about 0.01 wt. % to about 1 wt. %.

Antioxidants prevent the formation of gum depositions on fuel system components caused by oxidation of fuels in storage and/or inhibit the formation of peroxide compounds in certain fuel compositions can be used herein. The antioxidant may be present in the fuel composition at a concentration from about 0.001 wt. % to about wt. %, based on the total weight of the fuel composition, and in one embodiment from about 0.01 wt. % to about 1 wt. %.

Static dissipaters reduce the effects of static electricity generated by movement of fuel through high flow-rate fuel transfer systems. The static dissipater may be present in the fuel composition at a concentration from about 0.001 wt. % to about 5 wt. %, based on the total weight of the fuel composition, and in one embodiment from about 0.01 wt. % to about 1 wt. %.

Corrosion inhibitors protect ferrous metals in fuel handling systems such as pipelines, and fuel storage tanks, from corrosion. In circumstances where additional lubricity is desired, corrosion inhibitors that also improve the lubricating properties of the composition can be used. The corrosion inhibitor may be present in the fuel composition at a concentration from about 0.001 wt. % to about 5 wt. %, based on the total weight of the fuel composition, and in one embodiment from about 0.01 wt. % to about 1 wt. %.

Fuel system icing inhibitors (also referred to as anti-icing additive) reduce the freezing point of water precipitated from jet fuels due to cooling at high altitudes and prevent the formation of ice crystals which restrict the flow of fuel to the engine. Certain fuel system icing inhibitors can also act as a biocide. The fuel system icing inhibitor may be present in the fuel composition at a concentration from about 0.001 wt. % to about 5 wt. %, based on the total weight of the fuel composition, and in one embodiment from about 0.01 wt. % to about 1 wt. %.

Biocides are used to combat microbial growth in the fuel composition. The biocide may be present in the fuel composition at a concentration from about 0.001 wt. % to about 5 wt. %, based on the total weight of the fuel composition, and in one embodiment from about 0.01 wt. % to about 1 wt. %.

Metal deactivators suppress the catalytic effect of some metals, particularly copper, have on fuel oxidation. The metal deactivator may be present in the fuel composition at a concentration from about 0.001 wt. % to about 5 wt. %, based on the total weight of the fuel composition, and in one embodiment from about 0.01 wt. % to about 1 wt. %.

Thermal stability improvers are use to inhibit deposit formation in the high temperature areas of the aircraft fuel system. The thermal stability improver may be present in the fuel composition at a concentration from about 0.001 wt. % to about 5 wt. %, based on the total weight of the fuel composition, and in one embodiment from about 0.01 wt. % to about 1 wt. %.

In some embodiments, the fuel composition has a flash point greater than about 32° C., greater than about 33° C., greater than about 34° C., greater than about 35° C., greater than about 36° C., greater than about 37° C., greater than about 38° C., greater than about 39° C., greater than about 40° C., greater than about 41° C., greater than about 42° C., greater than about 43° C., or greater than about 44° C. In other embodiments, the fuel composition has a flash point greater than 38° C. In certain embodiments, the flash point of the fuel composition disclosed herein is measured according to ASTM Standard D 56. In other embodiments, the flash point of the fuel composition disclosed herein is measured according to ASTM Standard D 93. In further embodiments, the flash point of the fuel composition disclosed herein is measured according to ASTM Standard D 3828-98. In still further embodiments, the flash point of the fuel composition disclosed herein is measured according to any conventional method known to a skilled artisan for measuring flash point of fuels.

In some embodiments, the fuel composition has a density at 15° C. from about 750 kg/m$^3$ to about 850 kg/m$^3$, from about 750 kg/m$^3$ to about 845 kg/m$^3$, from about 750 kg/m$^3$ to about 840 kg/m$^3$, from about 760 kg/m$^3$ to about 845 kg/m$^3$, from about 770 kg/m$^3$ to about 850 kg/m$^3$, from about 770 kg/m$^3$ to about 845 kg/m$^3$, from about 775 kg/m$^3$ to about 850 kg/m$^3$, or from about 775 kg/m$^3$ to about 845 kg/m$^3$. In other embodiments, the fuel composition has a density at 15° C. from about 780 kg/m$^3$ to about 845 kg/m$^3$. In still other embodiments, the fuel composition has a density at 15° C. from about 775 kg/m$^3$ to about 840 kg/m$^3$. In still other embodiments, the fuel composition has a density at 15° C. from about 750 kg/m$^3$ to about 805 kg/m$^3$. In certain embodiments, the density of the fuel composition disclosed herein is measured according to ASTM Standard D 4052. In further embodiments, the density of the fuel composition disclosed herein is measured according to any conventional method known to a skilled artisan for measuring density of fuels.

In some embodiments, the fuel composition has a freezing point that is lower than −30° C., lower than −40° C., lower than −50° C., lower than −60° C., lower than −70° C., or lower than −80° C. In other embodiments, the fuel composition has a freezing point from about −80° C. to about −30° C., from about −75° C. to about −35° C., from about −70° C. to about −40° C., or from about −65° C. to about −45° C. In certain embodiments, the freezing point of the fuel composition disclosed herein is measured according to ASTM Standard D 2386. In further embodiments, the freezing point of the fuel composition disclosed herein is measured according to any conventional method known to a skilled artisan for measuring freezing point of fuels.

In some embodiments, the fuel composition has a density at 15° C. from about 750 kg/m$^3$ to about 850 kg/m$^3$, and a flash point equal to or greater than 38° C. In certain embodiments, the fuel composition has a density at 15° C. from about 750 kg/m$^3$ to about 850 kg/m$^3$, a flash point equal to or greater than 38° C., and a freezing point lower than −40° C. In certain embodiments, the fuel composition has a density at 15° C. from about 750 kg/m$^3$ to about 840 kg/m$^3$, a flash point equal to or greater than 38° C., and a freezing point lower than −40° C.

In some embodiments, the fuel composition has an initial boiling point that is from about 140° C. to about 170° C. In other embodiments, the fuel composition has a final boiling point that is from about 180° C. to about 300° C. In still other embodiments, the fuel composition has an initial boiling from about 140° C. to about 170° C., and a final boiling point from about 180° C. to about 300° C. In certain embodiments, the fuel composition meets the distillation specification of ASTM D 86.

In some embodiments, the fuel composition has a Jet Fuel Thermal Oxidation Tester (JFTOT) temperature that is equal to or greater than 245° C. In other embodiments, the fuel composition has a JFTOT temperature that is equal to or greater than 250° C., equal to or greater than 255° C., equal to or greater than 260° C., or equal to or greater than 265° C.

In some embodiments, the fuel composition has a viscosity at −20° C. that is less than 6 mm$^2$/sec, less than 7 mm$^2$/sec, less than 8 mm$^2$/sec, less than 9 mm$^2$/sec, or less than 10 mm$^2$/sec. In certain embodiments, the viscosity of the fuel composition disclosed herein is measured according to ASTM Standard D 445.

In some embodiments, the fuel composition meets the ASTM D 1655 specification for Jet A-1. In other embodiments, the fuel composition meets the ASTM D 1655 specification for Jet A. In still other embodiments, the fuel composition meets the ASTM D 1655 specification for Jet B.

In another aspect, the invention provides a fuel composition comprising:
  (a) a $C_{10}$ bicyclic isoprenoid in an amount that is at least 10% by volume, based on the total volume of the fuel composition; and
  (b) kerosene in an amount that is at least 40% by volume, based on the total volume of the fuel composition,
wherein the fuel composition has a density at 15° C. from about 750 kg/m$^3$ to about 850 kg/m$^3$, a flash point equal to or greater than 38° C.; and a freezing point lower than −40° C.

In some embodiments, the amount of the $C_{10}$ bicyclic isoprenoid is at least about 15%, at least about 20%, at least about 25%, at least about 30%, at least about 35%, at least about 40%, at least about 45%, or at least about 50% by weight or volume, based on the total weight or volume of the fuel composition. In certain embodiments, the amount is in weight % based on the total weight of the fuel composition. In other embodiments, the amount is in volume % based on the total volume of the fuel composition.

In some embodiments, the $C_{10}$ bicyclic isoprenoid is carane. In other embodiments, the $C_{10}$ bicyclic isoprenoid is pinane. In still other embodiments, the $C_{10}$ bicyclic isoprenoid is sabinane. In certain embodiments, the $C_{10}$ bicyclic isoprenoid is a mixture comprising two or more of carane, pinane, and sabinane.

In certain embodiments, the fuel composition meets the ASTM D 1655 specification for Jet A.

In another aspect, a fuel system is provided comprising a fuel tank containing the fuel composition disclosed herein. Optionally, the fuel system may further comprise an engine cooling system having a recirculating engine coolant, a fuel line connecting the fuel tank with the internal combustion engine, and/or a fuel filter arranged on the fuel line. Some non-limiting examples of internal combustion engines include reciprocating engines (e.g., gasoline engines and diesel engines), Wankel engines, jet engines, some rocket engines, and gas turbine engines.

In some embodiments, the fuel tank is arranged with said cooling system so as to allow heat transfer from the recirculating engine coolant to the fuel composition contained in the fuel tank. In other embodiments, the fuel system further comprises a second fuel tank containing a second fuel for a jet engine and a second fuel line connecting the second fuel tank with the engine. Optionally, the first and second fuel lines can be provided with electromagnetically operated valves that can be opened or closed independently of each other or simultaneously. In further embodiments, the second fuel is a Jet A.

In another aspect, an engine arrangement is provided comprising an internal combustion engine, a fuel tank containing the fuel composition disclosed herein, a fuel line connecting the fuel tank with the internal combustion engine. Optionally, the engine arrangement may further comprise a fuel filter and/or an engine cooling system comprising a recirculating engine coolant. In some embodiments, the internal combustion engine is a diesel engine. In other embodiments, the internal combustion engine is a jet engine.

When using a fuel composition disclosed herein, it is desirable to remove particulate matter originating from the fuel composition before injecting it into the engine. Therefore, it is desirable to select a suitable fuel filter for use in a fuel system disclosed herein. Water in fuels used in an internal combustion engine, even in small amounts, can be very harmful to the engine. Therefore, it is desirable that any water present in fuel composition be removed prior to injection into the engine. In some embodiments, water and particulate matter can be removed by the use of a fuel filter utilizing a turbine centrifuge, in which water and particulate matter are separated from the fuel composition to an extent allowing injection of the filtrated fuel composition into the engine, without risk of damage to the engine. Other types of fuel filters that can remove water and/or particulate matter also may be used.

In another aspect, a vehicle is provided comprising an internal combustion engine, a fuel tank containing the fuel composition disclosed herein, and a fuel line connecting the fuel tank with the internal combustion engine. Optionally, the vehicle may further comprise a fuel filter and/or an engine cooling system comprising a recirculating engine coolant. Some non-limiting examples of vehicles include cars, motorcycles, trains, ships, and aircraft.

Methods for Making Fuel Compositions

In another aspect, provided herein are methods of making a fuel composition comprising the steps of:
  (a) contacting a $C_{10}$ isoprenoid starting material with hydrogen in the presence of a catalyst to form a $C_{10}$ bicyclic isoprenoid; and
  (b) mixing the $C_{10}$ bicyclic isoprenoid with a fuel component to make the fuel composition.

In one embodiment, the $C_{10}$ isoprenoid starting material is carene and the $C_{10}$ bicyclic isoprenoid is carane. In another embodiment, the $C_{10}$ isoprenoid starting material is α-pinene and the $C_{10}$ bicyclic isoprenoid is pinane. In another embodiment, the $C_{10}$ isoprenoid starting material is β-pinene and the $C_{10}$ bicyclic isoprenoid is pinane. In still other embodiments, the $C_{10}$ isoprenoid starting material is a mixture of α-pinene and β-pinene and the $C_{10}$ bicyclic isoprenoid is pinane. In further embodiments, the $C_{10}$ isoprenoid starting material is sabinene and the $C_{10}$ bicyclic isoprenoid is sabinane.

In another aspect, provided herein are methods of making a fuel composition from a simple sugar comprising the steps of:

(a) contacting a cell capable of making a $C_{10}$ isoprenoid starting material with the simple sugar under conditions suitable for making the $C_{10}$ isoprenoid starting material;

(b) converting the $C_{10}$ isoprenoid starting material to a $C_{10}$ bicyclic isoprenoid; and (c) mixing the $C_{10}$ bicyclic isoprenoid with a fuel component to make the fuel composition.

In some embodiments, the $C_{10}$ isoprenoid starting material is converted into a $C_{10}$ bicyclic isoprenoid by contacting the isoprenoid starting material with hydrogen in the presence of a catalyst.

In another aspect, a facility is provided for manufacture of a fuel, bioengineered fuel component, or bioengineered fuel additive of the invention. In certain embodiments, the facility is capable of biological manufacture of the $C_{10}$ starting materials. In certain embodiments, the facility is further capable of preparing an isoprenoid fuel additive or fuel component from the starting material.

The facility can comprise any structure useful for preparing the $C_{10}$ starting material using a microorganism. In some embodiments, the biological facility comprises one or more of the cells disclosed herein. In some embodiments, the biological facility comprises a cell culture comprising at least a $C_{10}$ starting material in an amount of at least about 1 wt. %, at least about 5 wt. %, at least about 10 wt. %, at least about 20 wt. %, or at least about 30 wt. %, based on the total weight of the cell culture. In further embodiments, the biological facility comprises a fermentor comprising one or more cells described herein.

Any fermentor that can provide cells or bacteria a stable and optimal environment in which they can grow or reproduce can be used herein. In some embodiments, the fermentor comprises a culture comprising one or more of the cells disclosed herein. In other embodiments, the fermentor comprises a cell culture capable of biologically manufacturing geranyl pyrophosphate (GPP). In further embodiments, the fermentor comprises a cell culture capable of biologically manufacturing isopentenyl diphosphate (IPP). In certain embodiments, the fermentor comprises a cell culture comprising at least a $C_{10}$ starting material in an amount of at least about 1 wt. %, at least about 5 wt. %; at least about 10 wt. %, at least about 20 wt. %, or at least about 30 wt. %, based on the total weight of the cell culture.

The facility can further comprise any structure capable of manufacturing the fuel component or fuel additive from the $C_{10}$ starting material. The structure may comprise a hydrogenator for the hydrogenation of the $C_{10}$ starting materials. Any hydrogenator that can be used to reduce C=C double bonds to C—C single bonds under conditions known to skilled artisans may be used herein. The hydrogenator may comprise a hydrogenation catalyst disclosed herein. In some embodiments, the structure further comprises a mixer, a container, and a mixture of the hydrogenation products from the hydrogenation step and a conventional fuel additive in the container.

The simple sugar can be any simple sugar known to those of skill in the art. Some non-limiting examples of suitable simple sugars or monosaccharides include glucose, galactose, mannose, fructose, ribose and combinations thereof. Some non-limiting examples of suitable disaccharides include sucrose, lactose, maltose, trehalose, cellobiose and combinations thereof. In certain embodiments, the bioengineered fuel component can be obtained from a polysaccharide. Some non-limiting examples of suitable polysaccharides include starch, glycogen, cellulose, chitin and combinations thereof.

The monosaccharides, disaccharides and polysaccharides suitable for making the bioengineered tetramethylcyclohexane can be found in a wide variety of crops or sources. Some non-limiting examples of suitable crops or sources include sugar cane, bagasse, miscanthus, sugar beet, sorghum, grain sorghum, switchgrass, barley, hemp, kenaf, potatoes, sweet potatoes, cassava, sunflower, fruit, molasses, whey or skim milk, corn, stover, grain, wheat, wood, paper, straw, cotton, many types of cellulose waste, and other biomass. In certain embodiments, the suitable crops or sources include sugar cane, sugar beet and corn.

Methods for Making Compounds

The compounds of the present invention can be made using any method known in the art including biologically, total chemical synthesis (without the use of biologically derived materials), and a hybrid method where both biologically and chemical means are used. In certain embodiments, the $C_{10}$ isoprenoid starting materials are each made by host cells by the conversion of simple sugar to the desired product.

Host Cells

The $C_{10}$ isoprenoid starting materials also can be made by any method known in the art including biological methods, chemical syntheses, and hybrid methods. When the $C_{10}$ isoprenoid starting material is made biologically, host cells that are modified to produce the desired product can be used. Like all isoprenoids, the $C_{10}$ isoprenoid starting material is made biochemically through a common intermediate, isopentenyl diphosphate ("IPP").

The host cell can be grown according to any technique known to those of skill in the art. In particular, the host cell can be grown in culture medium appropriate for the host cell. In advantageous embodiments, the culture medium comprises readily available, renewable components. The present invention thus provides readily available, renewable sources of energy methods of their use to produce fuel compositions. In certain embodiments, the host cell is grown or cultured by contact with a simple sugar under conditions suitable for their growth and production of a $C_{10}$ isoprenoid. In certain embodiments, the host cell can be grown or cultured by contact with glucose, galactose, mannose, fructose, ribose, or a combination thereof. The present invention thus provides fuel compositions derived from simple sugars, e.g. glucose, galactose, mannose, fructose, ribose, and combinations thereof, and methods of their production from the simple sugars.

Any suitable host cell may be used in the practice of the methods and compositions described herein. In one embodiment, the host cell is a genetically modified host microorganism in which nucleic acid molecules have been inserted, deleted or modified (i.e., mutated; e.g., by insertion, deletion, substitution, and/or inversion of nucleotides), either to produce the desired isoprenoid or isoprenoid derivative, or to produce increased yields of the desired isoprenoid or isoprenoid derivative. In certain embodiments, the host cell is capable of being grown in liquid growth medium.

Illustrative examples of suitable host cells include any archae, bacterial, or eukaryotic cell. Examples of an archae cell include, but are not limited to those belonging to the genera: *Aeropyrum, Archaeglobus, Halobacterium, Methanococcus, Methanobacterium, Pyrococcus, Sulfolobus*, and *Thermoplasma*. Illustrative examples of archae species include but are not limited to: *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum*, and *Thermoplasma volcanium*.

Examples of useful bacterial species include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*.

Illustrative examples of useful bacterial species include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus*, and the like.

In general, if a bacterial host cell is used, a non-pathogenic strain is preferred. Illustrative examples of non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum*, and the like.

Examples of useful eukaryotic cells include but are not limited to fungal cells. Examples of fungal cell include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces*, and *Trichoderma*.

Illustrative examples of useful eukaryotic species include but are not limited to: *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccharomyces cerevisiae, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus*, and *Trichoderma reesei*.

In general, if a eukaryotic cell is used, a non-pathogenic species is preferred. Illustrative examples of non-pathogenic species include but are not limited to: *Fusarium graminearum, Fusarium venenatum, Pichia pastoris, Saccaromyces boulardi*, and *Saccaromyces cerevisiae*.

In addition, certain species have been designated by the Food and Drug Administration as GRAS or Generally Regarded As Safe. These strains include: *Bacillus subtilis, Lactibacillus acidophilus, Lactobacillus helveticus*, and *Saccharomyces cerevisiae*.

IPP Pathways

There are two known biosynthetic pathways that synthesize IPP and its isomer, dimethylallyl pyrophosphate ("DMAPP"). Eukaryotes other than plants use the mevalonate-dependent ("MEV") isoprenoid pathway exclusively to convert acetyl-coenzyme A ("acetyl-CoA") to IPP, which is subsequently isomerized to DMAPP. Prokaryotes, with some exceptions, use the mevalonate-independent or deoxyxylulose 5-phosphate ("DXP") pathway to produce IPP and DMAPP separately through a branch point. In general, plants use both the MEV and DXP pathways for IPP synthesis.

MEV Pathway

A schematic representation of the MEV pathway is described in FIG. 1. In general, the pathway comprises six steps.

In the first step, two molecules of acetyl-coenzyme A are enzymatically combined to form acetoacetyl-CoA. An enzyme known to catalyze this step is, for example, acetyl-CoA thiolase. Illustrative examples of nucleotide sequences include but are not limited to the following GenBank accession numbers and the organism from which the sequences derived: (NC_000913 REGION: 2324131 . . . 2325315; *Escherichia coli*), (D49362; *Paracoccus denitrificans*), and (L20428; *Saccharomyces cerevisiae*).

In the second step of the MEV, pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Illustrative examples of nucleotide sequences include but are not limited to: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In the third step, HMG-CoA is enzymatically-converted to mevalonate. An enzyme known to catalyze this step is, for example, HMG-CoA reductase. Illustrative examples of nucleotide sequences include but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*).

In the fourth step, mevalonate is enzymatically phosphorylated to form mevalonate 5-phosphate. An enzyme known to catalyze this step is, for example, mevalonate kinase. Illustrative examples of nucleotide sequences include but are not limited to: (L77688; *Arabidopsis thaliana*), and (X55875; *Saccharomyces cerevisiae*).

In the fifth step, a second phosphate group is enzymatically added to mevalonate 5-phosphate to form mevalonate 5-pyrophosphate. An enzyme known to catalyze this step is, for example, phosphomevalonate kinase. Illustrative examples of nucleotide sequences include but are not limited to: (AF429385; *Hevea brasiliensis*), (NM_006556; *Homo sapiens*), and (NC_001145. complement 712315 . . . 713670; *Saccharomyces cerevisiae*).

In the sixth step, mevalonate 5-pyrophosphate is enzymatically converted into IPP. An enzyme known to catalyze this step is, for example, mevalonate pyrophosphate decarboxylase. Illustrative examples of nucleotide sequences include but are not limited to: (X97557; *Saccharomyces cerevisiae*), (AF290095; *Enterococcus faecium*), and (U49260; *Homo sapiens*).

If IPP is to be converted to DMAPP using the mevalonate pathway, then a seventh step is required. An enzyme known to catalyze this step is, for example, IPP isomerase. Illustrative examples of nucleotide sequences include but are not limited to: (NC_000913, 3031087.3031635; *Escherichia coli*), and (AF082326; *Haematococcus pluvialis*).

DXP Pathway

Figure 2:
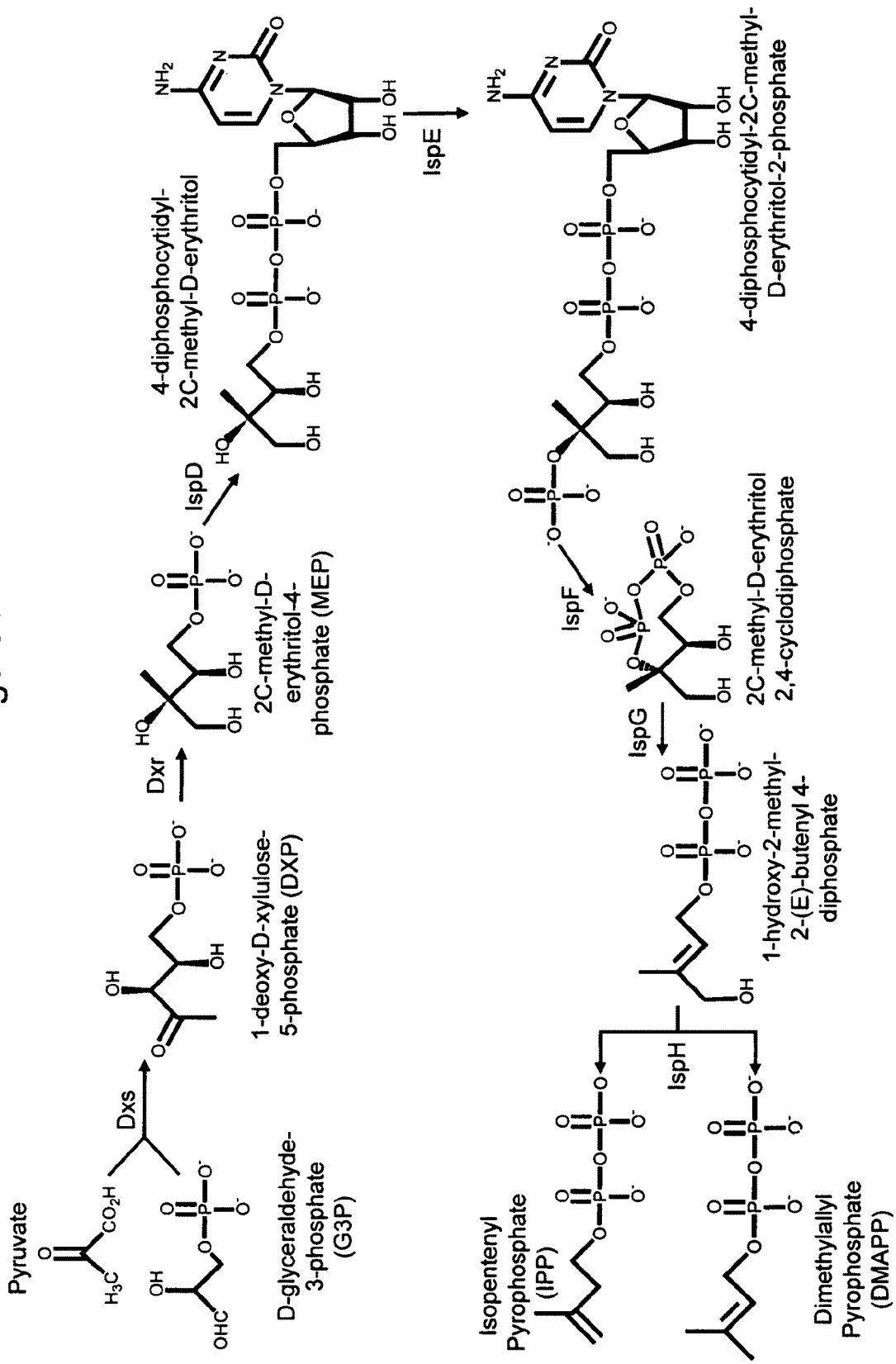
FIG. 2 is a schematic representation of the DXP pathway for the production of IPP and dimethylallyl pyrophosphate ("DMAPP"). Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritol synthase; IspF is 2C-methyl-D-erythritol 2,4-cyclodiphosphate synthase; IspG is 1-hydroxy-2-methyl-2-(E)-butenyl 4-diphosphate synthase (IspG); and ispH is isopentenyl/dimethylallyl diphosphate synthase.

A schematic representation of the DXP pathway is described in FIG. 2. In general, the DXP pathway comprises seven steps. In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Illustrative examples of nucleotide sequences include but are not limited to: (AF035440; *Escherichia coli*), (NC_002947, locus tag PP0527; *Pseudomonas putida* KT2440), (CP000026, locus tag SPA2301; *Salmonella enterica Paratyphi*, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC_004556, locus tag PD1293; *Xylella fastidiosa* Temecula1), and (NC_003076, locus tag AT5G11380; *Arabidopsis thaliana*).

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP_2709; *Rhodobacter sphaeroides* 2.4.1), and (NC_007492, locus tag Pfl_1107; *Pseudomonas fluorescens* PfO-1).

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Illustrative examples of nucleotide sequences include but are not limited to: (AF230736; *Escherichia coli*), (NC_007493, locus_tag RSP_2835; *Rhodobacter sphaeroides* 2.4.1), (NC_003071, locus_tag AT2G02500; *Arabidopsis thaliana*), and (NC_002947, locus_tag PP1614; *Pseudomonas putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Illustrative examples of nucleotide sequences include but are not limited to: (AF216300; *Escherichia coli*) and (NC_007493, locus_tag RSP_1779; *Rhodobacter sphaeroides* 2.4.1).

In the fifth step, 4-diphosphocytidyl-2C-methyl-D-erythritol-2-phosphate is converted to 2C-methyl-D-erythritol 2,4-cyclodiphosphate. An enzyme known to catalyze this step is, for example, 2C-methyl-D-erythritol 2,4-cyclodiphosphate synthase. Illustrative examples of nucleotide sequences include but are not limited to: (AF230738; *Escherichia coli*), (NC_007493, locus_tag RSP_6071; *Rhodobacter sphaeroides* 2.4.1), and (NC_002947, locus_tag PP1618; *Pseudomonas putida* KT2440).

In the sixth step, 2C-methyl-D-erythritol 2,4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Illustrative examples of nucleotide sequences include but are not limited to: (AY033515; *Escherichia coli*), (NC_002947, locus_tag PP0853; *Pseudomonas putida* KT2440), and (NC_007493, locus_tag RSP_2982; *Rhodobacter sphaeroides* 2.4.1).

In the seventh step, 1-hydroxy-2-methyl-2-(E)-butenyl-4-diphosphate is converted into either IPP or its isomer, DMAPP. An enzyme known to catalyze this step is, for example, isopentyl/dimethylallyl diphosphate synthase. Illustrative examples of nucleotide sequences include but are not limited to: (AY062212; *Escherichia coli*) and (NC_002947, locus_tag PP0606; *Pseudomonas putida* KT2440).

In some embodiments, "cross talk" (or interference) between the host cell's own metabolic processes and those processes involved with the production of IPP as provided herein are minimized or eliminated entirely. For example, cross talk is minimized or eliminated entirely when the host microorganism relies exclusively on the DXP pathway for synthesizing IPP, and a MEV pathway is introduced to provide additional IPP. Such a host organisms would not be equipped to alter the expression of the MEV pathway enzymes or process the intermediates associated with the MEV pathway. Organisms that rely exclusively or predominately on the DXP pathway include, for example, *Escherichia coli*.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

Isoprenoid Starting Material

Figure 3:
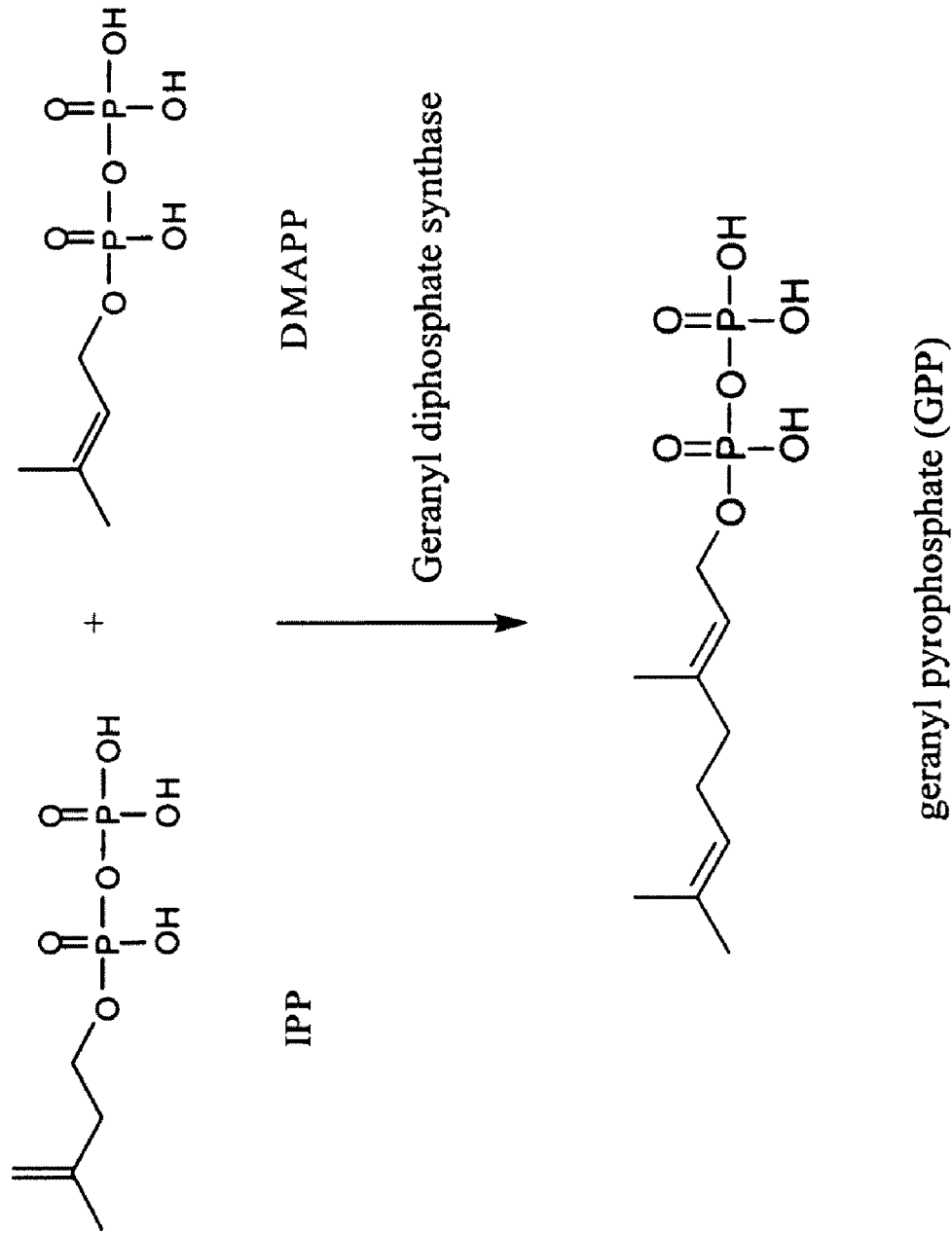
FIG. 3 is a schematic representation of the conversion of one molecule of IPP and one molecule of DMAPP to geranyl diphosphate ("GPP"). An enzyme known to catalyze this step is, for example, geranyl diphosphate synthase.

In some embodiments GPP is prepared by the method as described schematically in FIG. 3. One molecule of IPP and one molecule of DMAPP are condensed to form GPP. In some embodiments, the reaction can be catalyzed by an enzyme known to catalyze this step, for example, geranyl diphosphate synthase. Various $C_{10}$ isoprenoid starting materials can be made from GPP.

Illustrative examples of polynucleotides encoding geranyl pyrophosphate synthase include but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha* x *piperita*), (AF182827; *Mentha* x *piperita*), (MPI249453; *Mentha* x *piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

GPP can then be subsequently converted to various $C_{10}$ isoprenoid starting materials using one or more terpene synthases. Some non-limiting examples include the following examples and stereoisomers thereof.

Carene

Carene, whose structure is

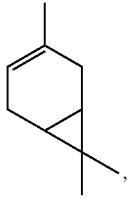

is found in the resin of many trees, particularly pine trees. Carene is made from GPP from carene synthase. Illustrative examples of suitable nucleotide sequences include but are not limited to: (AF461-460, REGION 43 . . . 1926; *Picea abies*) and (AF527416, REGION: 78 . . . 1871; *Salvia stenophylla*).

α-Pinene

α-Pinene, whose structure is

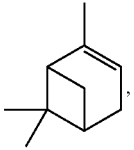

is found in pine trees and eucalyptus. α-Pinene is made from GPP by α-pinene synthase. Illustrative examples of suitable nucleotide sequences include but are not limited to: (+) α-pinene synthase (AF543530, REGION: 1 . . . 1887; *Pinus taeda*), (−)α-pinene synthase (AF543527, REGION: 32 . . . 1921; *Pinus taeda*), and (+)/(−)α-pinene synthase (AGU87909, REGION: 6111892; *Abies grandis*).

β-Pinene

β-Pinene, whose structure is

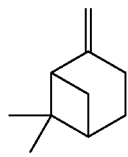

is found in pine trees, rosemary, parsley, dill, basil, and rose. β-Pinene is made from GPP by β-pinene synthase. Illustrative examples of suitable nucleotide sequences include but are not limited to: (−) β-pinene synthases (AF276072, REGION: 1 . . . 1749; *Artemisia annua*) and (AF514288, REGION: 26 . . . 1834; *Citrus limon*).

Sabinene

Sabinene, whose structure is

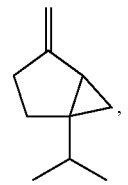

is found in black pepper, carrot seed, sage, and tea trees. Sabinene is made from GPP by sabinene synthase. An illustrative example of a suitable nucleotide sequence includes but is not limited to AF051901, REGION: 26 . . . 1798 from *Salvia officinalis*.

In some embodiments, the isoprenoid starting materials can be obtained or prepared from naturally occurring terpenes that can be produced by a wide variety of plants, such as *Copaifera langsdorfii*, conifers, and spurges; insects, such as swallowtail butterflies, leaf beetles, termites, and pine sawflies; and marine organisms, such as algae, sponges, corals, mollusks, and fish.

*Copaifera langsdorfii* or *Copaifera* tree is also known as the diesel tree and kerosene tree. It has many names in local languages, including kupa'y, cabismo, and copaúva. *Copaifera* tree may produce a large amount of terpene hydrocarbons in its wood and leaves. Generally, one *Copaifera* tree can produce from about 30 to about 40 liters of terpene oil per year.

Terpene oils can also be obtained from conifers and spurges. Conifers belong to the plant division *Pinophyta* or *Coniferae* and are generally cone-bearing seed plants with vascular tissue. The majority of conifers are trees, but some conifers can be shrubs. Some non-limiting examples of suitable conifers include cedars, cypresses, douglas-firs, firs, junipers, kauris, larches, pines, redwoods, spruces, and yews. Spurges, also known as *Euphorbia*, are a very diverse worldwide genus of plants, belonging to the spurge family (Euphorbiaceae). Consisting of about 2160 species, spurges are one of the largest genera in the plant kingdom.

The $C_{10}$ isoprenoid starting materials are monoterpenes which are part of a larger class of compound called terpenes. A large and varied class of hydrocarbons, terpenes include hemiterpenes, monoterpenes, sesquiterpenes, diterpenes, sesterterpenes, triterpenes, tetraterpenes, and polyterpenes. As a result, suitable $C_{10}$ isoprenoid starting materials can be isolated from terpene oils for use in the present invention Chemical Conversion In certain embodiments, one or more $C_{10}$ isoprenoid starting materials are isolated from naturally occurring sources and subsequently are converted to the corresponding $C_{10}$ bicyclic isoprenoids.

Irrespective of its source, a $C_{10}$ isoprenoid starting material can be chemically converted into a $C_{10}$ bicyclic isoprenoid by any known reduction reaction such as hydrogenation reactions. In some embodiments, the $C_{10}$ isoprenoid starting material can be reduced by hydrogen with a catalyst such as Pd, Pd/C, Pt, $PtO_2$, $Ru(PPh_3)_2Cl_2$, Raney nickel and combinations thereof. Generally, after completion, the reaction mixture can be washed, concentrated, and dried to yield the corresponding hydrogenated product.

The catalyst for the hydrogenation reaction of the $C_{10}$ isoprenoid starting materials can be present in any amount for the reaction to proceed. In some embodiments, the amount of the hydrogenation catalyst is from about 1 g to about 100 g per liter of reactant, from about 2 g to about 75 g per liter of reactant, from about 3 g to about 50 g per liter of reactant, from about 4 g to about 40 g per liter of reactant, from about 5 g to about 25 g per liter of reactant, or from about 5 g to about 10 g per liter of reactant.

In some embodiments, the hydrogenation reaction proceeds at room temperature. In certain embodiments, the reaction temperature between about 10° C. and about 75° C., between about 15° C. and about 60° C., between about 20° C. and about 50° C., or between about 20° C. and about 40° C. In other embodiments, the reaction temperature is between about 75° C. and about 150° C., between about 90° C. and about 130° C., or between about 100° C. and about 125° C.

The pressure of the hydrogen for the hydrogenation reaction can be any pressure that can cause the reaction to proceed. In some embodiments, the pressure of the hydrogen is between about 10 psi and about 1000 psi, between about 50 psi and about 800 psi, between about 400 psi and about 600 psi, or between about 450 psi and about 550 psi. In other embodiments, the pressure of hydrogen is less than 100 psi.

In some embodiments, the catalyst is a Pd catalyst. In other embodiments, the catalyst is 5% Pd/C. In still other embodiments, the catalyst is 10% Pd/C. In certain of these embodiments, the catalyst loading is between about 1 g and about 10 g per liter of reactant. In other embodiments, the catalyst loading is between about 5 g and about 5 g per liter of reactant.

In some embodiments, the C=C bonds in the $C_{10}$ isoprenoid starting materials are reduced to the corresponding C—C bonds by hydrogenation in the presence of a catalyst and hydrogen at room temperature. In certain embodiments, carene is reduced to carane by hydrogen in the presence of a 10% Pd/C catalyst as shown in Scheme 1 below Scheme 1

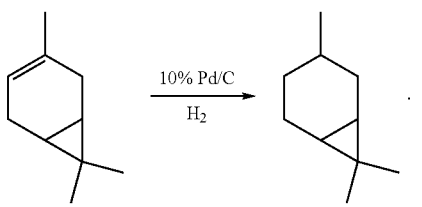

In further embodiments, α-pinene or β-pinene is reduced to pinane by hydrogen in the presence of a 10% Pd/C catalyst as shown in Scheme 2 below Scheme 2

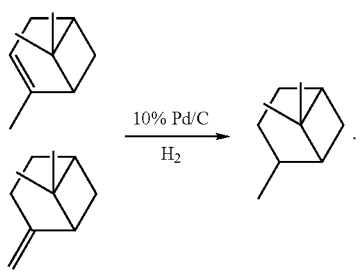

In still further embodiments, sabinene is reduced to sabinane by hydrogen in the presence of a 10% Pd/C catalyst as shown in Scheme 3 below Scheme 3

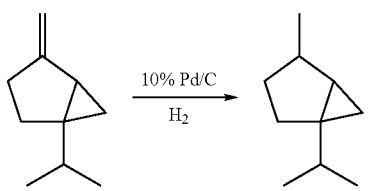

Alternatively, any reducing agent that can reduce a C=C bond to a C—C bond can also be used. For example, the $C_{10}$ isoprenoid starting material can be hydrogenated by treatment with hydrazine in the presence of a catalyst, such as 5-ethyl-3-methyllumiflavinium perchlorate, under oxygen atmosphere to give the corresponding hydrogenated products. A reduction reaction with hydrazine is disclosed in Imada et al., *J. Am. Chem. Soc.*, 127, 14544-14545 (2005), which is incorporated herein by reference.

The hydrogenation of the $C_{10}$ isoprenoid starting materials can be carried out in the presence of an asymmetric hydrogenation catalyst such as rhodium-chiral diphosphine complex to form stereospecific hydrogenated products substantially free of other stereoisomers. A non-limiting example of the asymmetric hydrogenation catalyst includes the rhodium-DIPAMP catalyst. The rhodium-DIPAMP catalyst and other asymmetric hydrogenation catalysts are disclosed in Vineyard et al., J. Am. Chem. Soc. 1977, 99, (18), 5946; Ryoji Noyori, "*Asymmetric Catalysis In Organic Synthesis*," John Wiley & Sons Inc., New York, Chapter 2, pp. 16-94 (1994); and Blaser et al., "*Asymmetric Catalysis on Industrial Scale: Challenges, Approaches and Solutions*," Wiley-VCH, Weinheim, pp. 23-52 (2004), all of which are incorporated herein by reference in their entirety.

In some embodiments, carene can be hydrogenated in the presence of an asymmetric hydrogenation catalyst to form one of the four possible stereoisomers of carane which are shown below:

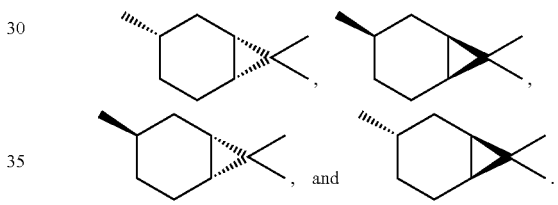

In other embodiments, α-pinene or β-pinene can be hydrogenated in the presence of an asymmetric hydrogenation catalyst to form one of the four possible stereoisomers of pinane which are shown below:

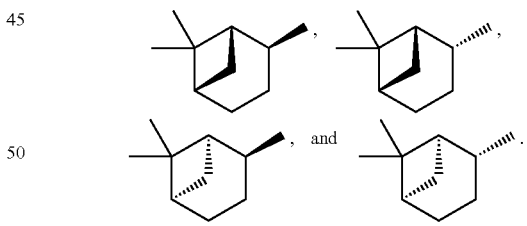

In further embodiments, sabinene can be hydrogenated in the presence of an asymmetric hydrogenation catalyst to form one of the four possible stereoisomers of sabinane (also known as thujane or tenacetane) which are shown below:

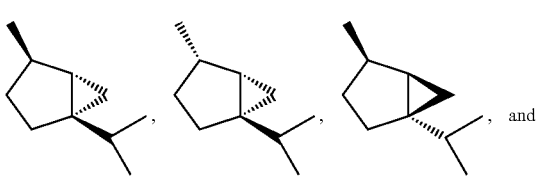

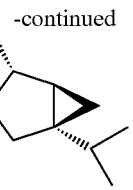

Business Methods

One aspect of the present invention relates to a business method comprising: (a) obtaining a biofuel comprising $C_{10}$ bicyclic isoprenoid derived from a $C_{10}$ isoprenoid starting material by performing a fermentation reaction of a sugar with a recombinant host cell, wherein the recombinant host cell produces the $C_{10}$ isoprenoid starting material; and (b) marketing and/or selling said biofuel.

In other embodiments, the invention provides a method for marketing or distributing the biofuel disclosed herein to marketers, purveyors, and/or users of a fuel, which method comprises advertising and/or offering for sale the biofuel disclosed herein. In further embodiments, the biofuel disclosed herein may have improved physical or marketing characteristics relative to the natural fuel or ethanol-containing biofuel counterpart.

In certain embodiments, the invention provides a method for partnering or collaborating with or licensing an established petroleum oil refiner to blend the biofuel disclosed herein into petroleum-based fuels such as a gasoline, jet fuel, kerosene, diesel fuel or a combination thereof. In another embodiment, the invention provides a method for partnering or collaborating with or licensing an established petroleum oil refiner to process (for example, hydrogenate, hydrocrack, crack, further purify) the biofuels disclosed herein, thereby modifying them in such a way as to confer properties beneficial to the biofuels. The established petroleum oil refiner can use the biofuel disclosed herein as a feedstock for further chemical modification, the end product of which could be used as a fuel or a blending component of a fuel composition.

In further embodiments, the invention provides a method for partnering or collaborating with or licensing a producer of sugar from a renewable resource (for example, corn, sugar cane, bagass, or lignocellulosic material) to utilize such renewable sugar sources for the production of the biofuels disclosed herein. In some embodiments, corn and sugar cane, the traditional sources of sugar, can be used. In other embodiments, inexpensive lignocellulosic material (agricultural waste, corn stover, or biomass crops such as switchgrass and pampas grass) can be used as a source of sugar. Sugar derived from such inexpensive sources can be fed into the production of the biofuel disclosed herein, in accordance with the methods of the present invention.

In certain embodiments, the invention provides a method for partnering or collaborating with or licensing a chemical producer that produces and/or uses sugar from a renewable resource (for example, corn, sugar cane, bagass, or lignocellulosic material) to utilize sugar obtained from a renewable resource for the production of the biofuel disclosed herein.

EXAMPLES

The following examples are intended for illustrative purposes only and do not limit in any way the scope of the present invention.

The practice of the present invention can employ, unless otherwise indicated, conventional techniques of the biosynthetic industry and the like, which are within the skill of the art. To the extent such techniques are not described fully herein, one can find ample reference to them in the scientific literature.

In the following examples, efforts have been made to ensure accuracy with respect to numbers used (for example, amounts, temperature, and so on), but variation and deviation can be accommodated, and in the event a clerical error in the numbers reported herein exists, one of ordinary skill in the arts to which this invention pertains can deduce the correct amount in view of the remaining disclosure herein. Unless indicated otherwise, temperature is reported in degrees Celsius, and pressure is at or near atmospheric pressure at sea level. All reagents, unless otherwise indicated, were obtained commercially. The following examples are intended for illustrative purposes only and do not limit in any way the scope of the present invention.

Example 1

This example describes methods for making expression plasmids that encode enzymes including enzymes of the MEV pathway from *Saccharomyces cerevisiae* organized in operons.

Expression plasmid pMevT was generated by inserting the MevT operon into the pBAD33 vector. The MevT operon encodes the set of MEV pathway enzymes that together transform the ubiquitous precursor acetyl-CoA to (R)-mevalonate, namely acetoacetyl-CoA thiolase, HMG-CoA synthase, and HMG-CoA reductase. The MevT operon was generated by PCR amplifying from *Escherichia coli* genomic DNA the coding sequence of the atoB gene (GenBank accession number NC_000913 REGION: 2324131 . . . 2325315) (encodes an acetoacetyl-CoA thiolase), from *Saccharomyces cerevisiae* genomic DNA the coding sequence of the ERG13 gene (GenBank accession number X96617, REGION: 220 . . . 1695) (encodes a HMG-CoA synthase), and from *Saccharomyces cerevisiae* genomic DNA a segment of the coding region of the HMG1 gene (GenBank accession number M22002, REGION: 1660 . . . 3165) (encodes a truncated HMG-CoA reductase (tHMGR)). The upstream PCR primer used for the amplification of the HMG1 gene fragment included an artificial start codon. The amplified fragments were spliced together using overlap extensions (SOEing), during which process ribosome binding sites were introduced after the atoB and the ERG13 coding sequences. After the addition of 3' A overhangs, the MevT operon was ligated into the TA cloning vector pCR4 (Invitrogen, Carlsbad, Calif.). The MevT operon was subsequently ligated into the XmaI PstI restriction site of vector pBAD33 (Guzman et al. (1995) *J. Bacteriol.* 177(14): 4121-4130). To place the operon under the control of the $P_{Lac}$ promoter, the araC-$P_{BAD}$ NsiI-XmaI fragment of pBAD33 was replaced with the NsiI-XmaI fragment of pBBR1MCS, yielding expression plasmid pMevT (see U.S. Pat. No. 7,192,751).

Expression plasmid pAM36-MevT66 was generated by inserting the MevT66 operon into the pAM36 vector. The pAM36 vector was generated by inserting an oligonucleotide cassette containing AscI-SfiI-AsiSI-XhoI-PacI-FsII-PmeI restriction sites into the pACYC184 vector (GenBank accession number XO6403), and by removing the tetramycin resistance conferring gene in pACYC184. The MevT66 operon was synthetically generated using SEQ ID NO: 1 as a template, which comprises the atoB gene from *Escherichia coli* (GenBank accession number NC_000913 REGION: 2324131 . . . 2325315), the ERG13 gene from *Saccharomyces cerevisiae* (GenBank accession number X96617, REGION: 220 . . . 1695), and a truncated version of the HMG1 gene from *Saccharomyces cerevisiae* (GenBank accession number M22002, REGION: 1777 ... 3285), all three sequences being codon-optimized for expression in *Escherichia coli*. The synthetically generated MevT66 operon was flanked by a 5' EcoRI restriction site and a 3' Hind III restriction site, and could thus be cloned into compatible restriction sites of a cloning vector such as a standard pUC or pACYC origin vector. From this construct, the MevT66 operon was PCR amplified with flanking SfiI and AsiSI restriction sites, the amplified DNA fragment was digested to completion using SfiI and AsiSI restriction enzymes, the reaction mixture was resolved by gel electrophoresis, the approximately 4.2 kb DNA fragment was gel extracted using a gel purification kit (Qiagen, Valencia, Calif.), and the isolated DNA fragment was ligated into the SfiI AsiSI restriction site of the pAM36 vector, yielding expression plasmid pAM36-MevT66.

Expression plasmid pAM25 was generated by inserting the MevT66 operon into the pAM29 vector. The pAM29 vector was created by assembling the p15A origin of replication and kanamycin resistance conferring gene from pZS24-MCS1 (Lutz and Bujard (1997) *Nucl Acids Res.* 25:1203-1210) with an oligonucleotide-generated lacUV5 promoter. The DNA synthesis construct comprising the MevT66 operon (see description for pAM36-MevT66 above) was digested to completion using EcoRI and Hind III restriction enzymes, the reaction mixture was resolved by gel electrophoresis, the approximately 4.2 kb DNA fragment was gel extracted, and the isolated DNA fragment was ligated into the EcoRI HindIII restriction site of pAM29, yielding expression plasmid pAM25.

Expression plasmid pMevB-Cm was generated by inserting the MevB operon into the pBBR1MCS-1 vector. The MevB operon encodes the set of enzymes that together convert (R)-mevalonate to IPP, namely mevalonate kinase, phosphomevalonate kinase, and mevalonate pyrophosphate carboxylase. The MevB operon was generated by PCR amplifying from *Saccharomyces cerevisiae* genomic DNA the coding sequences of the ERG12 gene (GenBank accession number X55875, REGION: 580 ... 1911) (encodes a mevalonate kinase), the ERG8 gene (GenBank accession number Z49939, REGION: 3363 ... 4718) (encodes a phosphomevalonate kinase), and the MVD1 gene (GenBank accession number X97557, REGION: 544 ... 1734) (encodes a mevalonate pyrophosphate carboxylase), and by splicing the PCR fragments together using overlap extensions (SOEing). By choosing appropriate primer sequences, the stop codons of ERG12 and ERG8 were changed from TAA to TAG during amplification to introduce ribosome binding sites. After the addition of 3' A overhangs, the MevB operon was ligated into the TA cloning vector pCR4 (Invitrogen, Carlsbad, Calif.). The MevB operon was excised by digesting the cloning construct to completion using PstI restriction enzyme, resolving the reaction mixture by gel electrophoresis, gel extracting the approximately 4.2 kb DNA fragment, and ligating the isolated DNA fragment into the PstI restriction site of vector pBBR1MCS-1 (Kovach et al., *Gene* 166(1): 175-176 (1995)), yielding expression plasmid pMevB-Cm.

Expression plasmid pMBI was generated by inserting the MBI operon into the pBBR1MCS-3 vector. In addition to the enzymes of the MevB operon, the MBI operon also encodes an isopentenyl pyrophosphatase isomerase, which catalyzes the conversion of IPP to DMAPP. The MBI operon was generated by PCR amplifying from *Escherichia coli* genomic DNA the coding sequence of the idi gene (GenBank accession number AF119715) using primers that contained an XmaI restriction site at their 5' ends, digesting the amplified DNA fragment to completion using XmaI restriction enzyme, resolving the reaction mixture by gel electrophoresis, gel extracting the approximately 0.5 kb fragment, and ligating the isolated DNA fragment into the XmaI restriction site of expression plasmid pMevB-Cm, thereby placing idi at the 3' end of the MevB operon. The MBI operon was subcloned into the SalI SacI restriction site of vector pBBR1MCS-3 (Kovach et al., *Gene* 166(1): 175-176 (1995)), yielding expression plasmid pMBI (see U.S. Pat. No. 7,192,751).

Expression plasmid pMBIS was generated by inserting the ispA gene into pMBI. The ispA gene encodes a farnesyl diphosphate synthase, which catalyzes the condensation of two molecules of IPP with one molecule of DMAPP to make farnesyl pyrophosphate (FPP). The coding sequence of the ispA gene (GenBank accession number D00694, REGION: 484 ... 1383) was PCR amplified from *Escherichia coli* genomic DNA using a forward primer with a SacII restriction site and a reverse primer with a SacI restriction site. The amplified PCR product was digested to completion using SacII and SacI restriction enzymes, the reaction mixture was resolved by gel electrophoresis, and the approximately 0.9 kb DNA fragment was gel extracted, and the isolated DNA fragment was ligated into the SacII SacI restriction site of pMBI, thereby placing the ispA gene 3' of idi and the MevB operon, and yielding expression plasmid pMBIS (see U.S. Pat. No. 7,192,751).

Expression plasmid pMBIS-gpps was derived from expression plasmid pMBIS by replacing the ispA coding sequence with a nucleotide sequence encoding a geranyl diphosphate synthase ("gpps"). A DNA fragment comprising a nucleotide sequence encoding a geranyl diphosphate synthase was generated synthetically using the coding sequence of the gpps gene of *Arabidopsis thaliana* (GenBank accession number Y17376, REGION: 52 ... 1320), codon-optimized for expression in *Escherichia coli*, as a template (SEQ ID NO: 2). The nucleotide sequence was flanked by a leader SacII restriction site and a terminal SacI restriction site, and could thus be cloned into compatible restriction sites of a cloning vector such as a standard pUC or pACYC origin vector. The synthetically generated geranyl diphosphate synthase sequence was isolated by digesting the DNA synthesis construct to completion using SacII and SacI restriction enzymes, resolving the reaction mixture by gel electrophoresis, gel extracting the approximately 1.3 kb DNA fragment, and ligating the isolated DNA fragment into the SacII SacI restriction site of expression plasmid pMBIS, yielding expression plasmid pMBIS-gpps.

Example 2

This example describes methods for making expression vectors encoding enzymes including enzymes of the MEV pathway from *Staphylococcus aureus* organized in operons.

Expression plasmid pAM41 was derived from expression plasmid pAM25 by replacing the coding sequence of the HMG1 gene, which encodes the *Saccharomyces cerevisiae* HMG-CoA reductase, with the coding sequence of the mvaA gene, which encodes the *Staphylococcus aureus* HMG-CoA reductase (GenBank accession number BA000017, REGION: 2688925 ... 2687648). The coding sequence of the mvaA gene was PCR amplified from *Staphyloccoccus aureus* subsp. *aureus* (ATCC 70069) genomic DNA using primers 4-49 mvaA SpeI (SEQ ID NO: 11) and 4-49 mvaAR XbaI (SEQ ID NO: 12), the amplified DNA fragment was digested to completion using SpeI restriction enzyme, the reaction mixture was resolved by gel electrophoresis, and the approximately 1.3 kb DNA fragment was gel extracted. The HMG1 coding sequence was removed from pAM25 by digesting the plasmid to completion using HindIII restriction enzyme. The terminal overhangs of the resulting linear DNA fragment were blunted using T4 DNA polymerase. The DNA fragment was then partially digested using SpeI restriction enzyme, the reaction mixture was resolved by gel electrophoresis, and the 4.8 kb DNA fragment was gel extracted. The isolated DNA fragment was ligated with the SpeI-digested mvaA PCR product, yielding expression plasmid pAM41.

Expression plasmid pAM52 was derived from expression plasmid pAM41 by replacing the coding sequence of the ERG13 gene, which encodes the *Saccharomyces cerevisiae* HMG-CoA synthase, with the coding sequence of the mvaS gene, which encodes the *Staphylococcus aureus* HMG-CoA synthase (GenBank accession number BA000017, REGION: 2689180 . . . 2690346). The coding sequence of the mvaS gene was PCR amplified from *Staphyloccocus aureus* subsp. *aureus* (ATCC 70069) genomic DNA using primers HMGS 5' Sa mvaS-S (SEQ ID NO: 13) and HMGS 3' Sa mvaS-AS (SEQ ID NO: 14), and the amplified DNA fragment was used as a PCR primer to replace the coding sequence of the HMG1 gene in pAM41 according to the method of Geiser et al. (*BioTechniques* 31:88-92 (2001)), yielding expression plasmid pAM52.

Example 3

This example describes methods for making expression plasmids that encode enzymes including enzymes of the DXP pathway from *Escherichia coli* organized in operons.

Figure 4A:
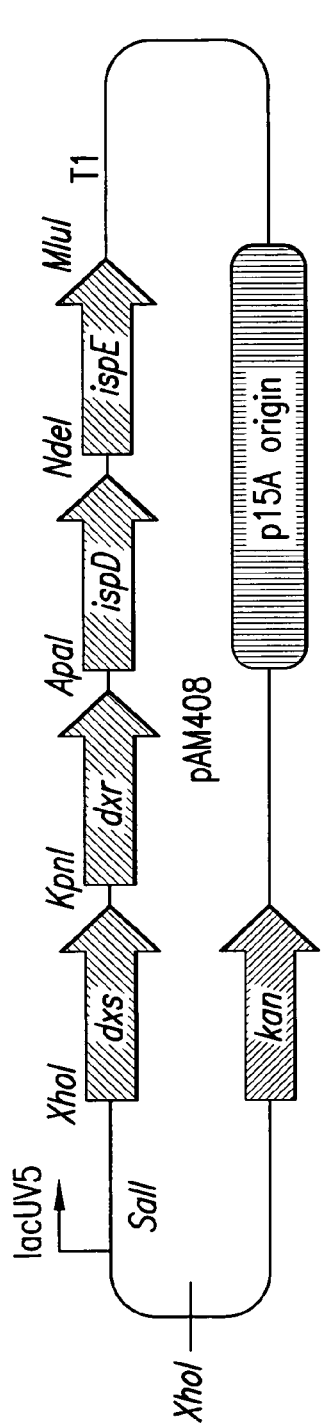
FIGS. 4A-C show maps of expression plasmids pAM408, pAM409, and pAM424.

Expression plasmid pAM408 was generated by inserting genes encoding enzymes of the "top" DXP pathway into the pAM29 vector. Enzymes of the "top" DXP pathway include 1-deoxy-D-xylulose-5-phosphate synthase (encoded by the dxs gene of *Escherichia coli*), 1-deoxy-D-xylulose-5-phosphate reductoisomerase (encoded by the dxr gene of *Escherichia coli*), 4-diphosphocytidyl-2C-methyl-D-erythritol synthase (encoded by the ispD gene of *Escherichia coli*), and 4-diphosphocytidyl-2C-methyl-D-erythritol synthase (encoded by the ispE gene of *Escherichia coli*), which together transform pyruvate and D-glyceraldehyde-3-phosphate into 4-diphosphocytidyl-2C-methyl-D-erythritol-2-phosphate. DNA fragments comprising nucleotide sequences that encode enzymes of the "top" DXP pathway were generated by PCR amplifying the coding sequences of the dxs (GenBank accession number U00096 REGION: 437539 . . . 439401), dxr (GenBank accession number U00096 REGION: 193521 . . . 194717), ispD (GenBank accession number U00096 REGION: 2869803 . . . 2870512), and ispE (GenBank accession number U00096 REGION 1261249 . . . 1262100) genes from *Escherichia coli* strain DH1 (ATCC #33849) with added optimal Shine Dalgarno sequences and 5' and 3' restriction sites using the PCR primers shown in SEQ ID NOs: 15 through 22. The PCR products were resolved by gel electrophoresis, gel extracted, digested to completion using appropriate restriction enzymes (XhoI and KpnI for the PCR product comprising the dxs gene; KpnI and ApaI for the PCR product comprising the dxr gene; ApaI and NdeI for the PCR product comprising the ispD gene; NdeI and MluI for the PCR product comprising the ispE gene), and purified using a PCR purification kit (Qiagen, Valencia, Calif.). Roughly equimolar amounts of each PCR product were then added to a ligation reaction to assemble the individual genes into an operon. From this ligation reaction, 1 ul of reaction mixture was used to PCR amplify two separate gene cassettes, namely the dxs-dxr and the ispD-ispE gene cassettes. The dxs-dxr gene cassette was PCR amplified using primers 67-1A-C (SEQ ID NO: 15) and 67-1D-C (SEQ ID NO: 18), and the ispD-ispE gene cassette was PCR amplified using primers 67-1E-C (SEQ ID NO: 19) and 67-1H-C (SEQ ID NO: 22). The two PCR products were resolved by gel elec-trophoresis, and gel extracted. The PCR product comprising the dxs-dxr gene cassette was digested to completion using XhoI and ApaI restriction enzymes, and the PCR product comprising the ispD-ispE gene cassette was digested to completion using ApaI and MluI restriction enzymes. The two PCR products were purified, and the purified DNA fragments were ligated into the SalI MluI restriction site of the pAM29 vector, yielding expression plasmid pAM408 (see FIG. 4A for a plasmid map).

Figure 4B:
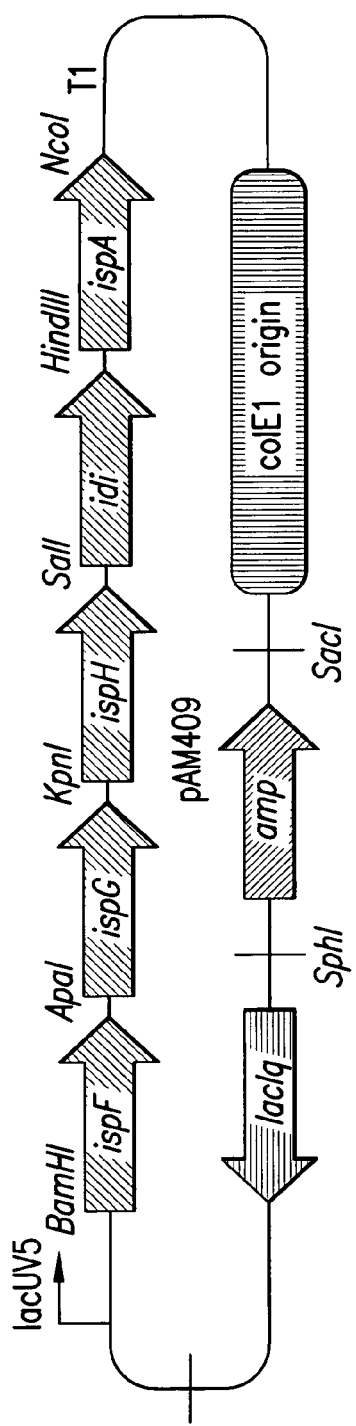

Expression plasmid pAM409 was generated by inserting genes encoding enzymes of the "bottom" DXP pathway into the pAM369 vector. Enzymes of the "bottom" DXP pathway include 2C-methyl-D-erythritol 2,4-cyclodiphosphate synthase (encoded by the ispF gene of *Escherichia coli*), 1-hydroxy-2-methyl-2-(E)-butenyl-4-diphosphate synthase (encoded by the ispG gene of *Escherichia coli*), and isopentenyl/dimethylallyl diphosphate synthase (encoded by the ispH gene of *Escherichia coli*), which together transform 4-diphosphocytidyl-2C-methyl-D-erythritol-2-phosphate to IPP and DMAPP. IPP is also converted to DMAPP through the activity of isopentyl diphosphate isomerase (encoded by the idi gene of *Escherichia coli*). DMAPP can be further converted to FPP through the activity of a farnesyl diphosphate synthase (such as encoded by the ispA gene of *Escherichia coli*). An operon encoding enzymes of the "bottom" DXP pathway as well as an isopentyl diphosphate isomerase and a farnesyl diphosphate synthase was generated by PCR amplifying the ispF (GenBank accession number U00096 REGION: 2869323 . . . 2869802), ispG (GenBank accession number U00096 REGION: 2638708 . . . 2639826), ispH (GenBank accession number U00096 REGION: 26277 . . . 27227), idi (GenBank accession number AF119715), and ispA (GenBank accession number D00694 REGION: 484 . . . 1383) genes from *Escherichia coli* strain DH1 (ATCC #33849) with added optimal Shine Dalgarno sequences and 5' and 3' restriction sites using the PCR primers shown in SEQ ID NOs: 23 through 32. The PCR products were resolved by gel electrophoresis, gel extracted, digested with the appropriate restriction enzymes (BamHI and ApaI for the PCR product comprising the ispF gene; KpnI and ApaI for the PCR product comprising the ispG gene; SalI and KpnI for the PCR product comprising the ispH gene; SalI and HindIII for the PCR product comprising the idi gene; HindIII and NcoI for the PCR product comprising the ispA gene), and purified. Roughly equimolar amounts of each PCR product were then added to a ligation reaction to assemble the individual genes into an operon. From this ligation reaction, 1 ul of reaction mixture was used to PCR amplify two separate gene cassettes, namely the ispF-ispG and the ispH-idi-ispA gene cassettes. The ispF-ispG gene cassette was PCR amplified using primers 67-2A-C (SEQ ID NO: 23) and 67-2D-C (SEQ ID NO: 26), and the ispH-idi-ispA gene cassette was PCR amplified using primers 67-2E-C (SEQ ID NO: 27) and 67-2J-C (SEQ ID NO: 32). The two PCR products were resolved by gel electrophoresis, and gel extracted. The PCR product comprising the ispF-ispG gene cassette was digested to completion using BamHI and KpnI restriction enzymes, and the PCR product comprising the ispH-idi-ispA gene cassette was digested to completion using KpnI and NcoI restriction enzymes. The two PCR products were purified. Vector pAM369 was created by assembling the p15A origin of replication from pAM29 and beta-lactamase gene for ampicillin resistance from pZE12-luc (Lutz and Bujard (1997) *Nucl Acids Res.* 25:1203-1210) with an oligonucleotide-generated lacUV5 promoter. The two isolated PCR products containing the "bottom" DXP pathway operon were ligated into the BamHI NcoI restriction site of the pAM369 vector, yielding expression plasmid pAM409 (see FIG. 4B for a plasmid map).

Figure 4C:
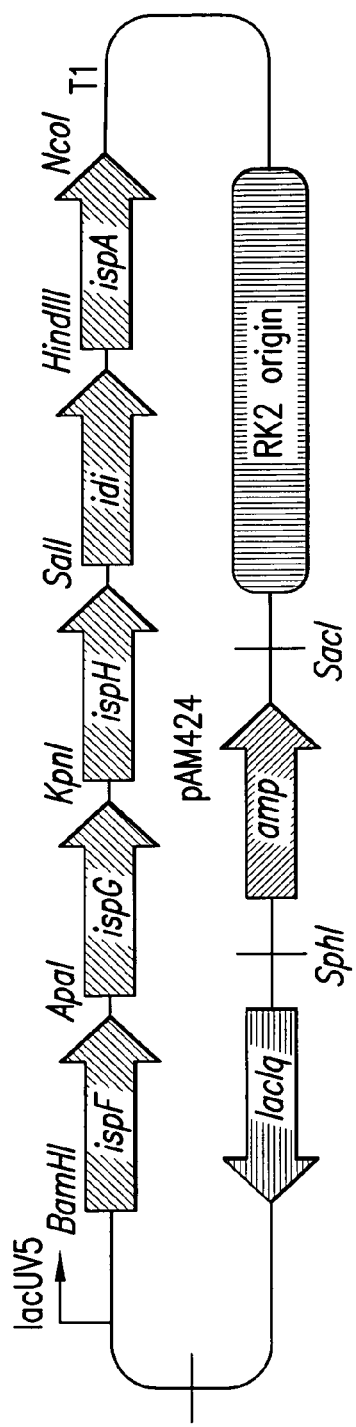

Expression plasmid pAM424, a derivative of expression plasmid pAM409 containing the broad-host range RK2 origin of replication, was generated by transferring the lacUV5 promoter and the ispFGH-idi-ispA operon of pAM409 to the pAM257 vector. Vector pAM257 was generated as follows: the RK2 par locus was PCR-amplified from RK2 plasmid DNA (Meyer et al. (1975) Science 190:1226-1228) using primers 9-156A (SEQ ID NO: 33) and 9-156B (SEQ ID NO: 34), the 2.6 kb PCR product was digested to completion using AatII and XhoI restriction enzymes, and the DNA fragment was ligated into a plasmid containing the p15 origin of replication and the chloramphenicol resistance conferring gene from vector pZA31-luc (Lutz and Bujard (1997) Nucl Acids Res. 25:1203-1210), yielding plasmid pAM37-par; pAM37-par was digested to completion using restriction enzymes SacI and HindIII, the reaction mixture was resolved by gel electrophoresis, the DNA fragment comprising the RK2 par locus and the chloramphenicol resistance gene was gel extracted, and the isolated DNA fragment was ligated into the SacI HindIII site of the mini-RK2 replicon pRR10 (Roberts et al. (1990) J. Bacteriol. 172:6204-6216), yielding vector pAM133; pAM133 was digested to completion using BglII and HindIII restriction enzymes, the reaction mixture was resolved by gel electrophoresis, the approximately 6.4 kb DNA fragment lacking the ampicillin resistance gene and oriT conjugative origin was gel extracted, and the isolated DNA fragment was ligated with a synthetically generated DNA fragment comprising a multiple cloning site that contained PciI and XhoI restriction sites, yielding vector pAM257. Expression plasmid pAM409 was digested to completion using XhoI and PciI restriction enzymes, the reaction mixture was resolved by gel electrophoresis, the approximately 4.4 kb DNA fragment was gel extracted, and the isolated DNA fragment was ligated into the XhoI PciI restriction site of the pAM257 vector, yielding expression plasmid pAM424 (see FIG. 4C for a plasmid map).

Example 4

This example describes methods for making vectors for the targeted integration of nucleic acids encoding enzymes including enzymes of the MEV pathway into specific chromosomal locations of Saccharomyces cerevisiae.

Genomic DNA was isolated from Saccharomyces cerevisiae strains Y002 (CEN.PK2 background; MATA; ura3-52; trp1-289; leu2-3,112; his3Δ1; MAL2-8C; SUC2), Y007 (S288C background MATA trp1-Δ63), Y051 (S288C background; MATα his3Δ1 leu2Δ0 lys2Δ0 ura3Δ0 $P_{GAL1}$-HMG1$^{1586-3323}$ $P_{GAL1}$-upc2-1 erg9::$P_{MET3}$-ERG9::HIS3 $P_{GAL1}$-ERG20 $P_{GAL1}$-HMG1$^{1586-3323}$) and EG123 (MATA ura3; trp1; leu2; his4 can1). The strains were grown overnight in liquid medium containing 1% Yeast extract, 2% Bacto-peptone, and 2% Dextrose (YPD medium). Cells were isolated from 10 mL liquid cultures by centrifugation at 3,100 rpm, washing of cell pellets in 10 mL ultra-pure water, and re-centrifugation. Genomic DNA was extracted using the Y-DER yeast DNA extraction kit (Pierce Biotechnologies, Rockford, Ill.) as per manufacturer's suggested protocol. Extracted genomic DNA was re-suspended in 100 uL 10 mM Tris-Cl, pH 8.5, and $OD_{260/280}$ readings were taken on a ND-1000 spectrophotometer (NanoDrop Technologies, Wilmington, Del.) to determine genomic DNA concentration and purity.

DNA amplification by Polymerase Chain Reaction (PCR) was done in an Applied Biosystems 2720 Thermocycler (Applied Biosystems Inc, Foster City, Calif.) using the Phusion High Fidelity DNA Polymerase system (Finnzymes O Y, Espoo, Finland) as per manufacturer's suggested protocol. Upon the completion of a PCR amplification of a DNA fragment that was to be inserted into the TOPO TA pCR2.1 cloning vector (Invitrogen, Carlsbad, Calif.), A nucleotide overhangs were created by adding 1 uL of Qiagen Taq Polymerase (Qiagen, Valencia, Calif.) to the reaction mixture and performing an additional 10 minute, 72° C. PCR extension step, followed by cooling to 4° C. Upon completion of a PCR amplification, 8 uL of a 50% glycerol solution was added to the reaction mix, and the entire mixture was loaded onto a 1% TBE (0.89 M Tris, 0.89 M Boric acid, 0.02 M EDTA sodium salt) agarose gel containing 0.5 ug/mL ethidium bromide.

Agarose gel electrophoresis was performed at 120 V, 400 mA for 30 minutes, and DNA bands were visualized using ultraviolet light. DNA bands were excised from the gel with a sterile razor blade, and the excised DNA was gel purified using the Zymoclean Gel DNA Recovery Kit (Zymo Research, Orange, Calif.) according to manufacturer's suggested protocols. The purified DNA was eluted into 10 uL ultra-pure water, and $OD_{260/280}$ readings were taken on a ND-1000 spectrophotometer to determine DNA concentration and purity.

Ligations were performed using 100-500 ug of purified PCR product and High Concentration T4 DNA Ligase (New England Biolabs, Ipswich, Mass.) as per manufacturer's suggested protocol. For plasmid propagation, ligated constructs were transformed into Escherichia coli DH5a chemically competent cells (Invitrogen, Carlsbad, Calif.) as per manufacturer's suggested protocol. Positive transformants were selected on solid media containing 1.5% Bacto Agar, 1% Tryptone, 0.5% Yeast Extract, 1% NaCl, and 50 ug/mL of an appropriate antibiotic. Isolated transformants were grown for 16 hours in liquid LB medium containing 50 ug/mL carbenicillin or kanamycin antibiotic at 37° C., and plasmid was isolated and purified using a QIAprep Spin Miniprep kit (Qiagen, Valencia, Calif.) as per manufacturer's suggested protocol. Constructs were verified by performing diagnostic restriction enzyme digestions, resolving DNA fragments on an agarose gel, and visualizing the bands using ultraviolet light. Select constructs were also verified by DNA sequencing, which was done by Elim Biopharmaceuticals Inc. (Hayward, Calif.).

Figure 5A:
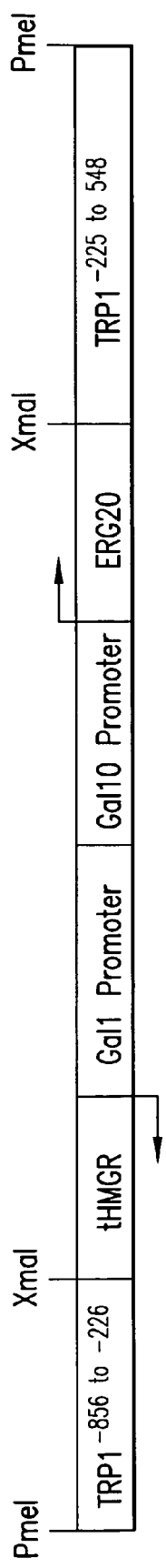
FIGS. 5A-E show maps of the inserts of vectors pAM489, pAM491, pAM493, pAM495, and pAM497.

Plasmid pAM489 was generated by inserting the ERG20-$P_{GAL}$-tHMGR insert of vector pAM471 into vector pAM466. Vector pAM471 was generated by inserting DNA fragment ERG20-$P_{GAL}$-tHMGR, which comprises the open reading frame (ORF) of ERG20 (ERG20 nucleotide positions 1 to 1208; A of ATG start codon is nucleotide 1) (ERG20), the genomic locus containing the divergent GAL1 and GAL10 promoter (GAL1 nucleotide position −1 to −668) ($P_{GAL}$), and a truncated ORF of HMG1 (HMG1 nucleotide positions 1586 to 3323) (tHMGR), into the TOPO Zero Blunt II cloning vector (Invitrogen, Carlsbad, Calif.). Vector pAM466 was generated by inserting DNA fragment TRP1$^{-856\ to\ +548}$, which comprises a segment of the wild-type TRP1 locus of Saccharomyces cerevisiae that extends from nucleotide position −856 to position 548 and harbors a non-native internal XmaI restriction site between bases −226 and −225, into the TOPO TA pCR2.1 cloning vector (Invitrogen, Carlsbad, Calif.). DNA fragments ERG20-$P_{GAL}$-tHMGR and TRP1$^{-856\ to\ +548}$ were generated by PCR amplification as outlined in Table 1. For the construction of pAM489, 400 ng of pAM471 and 100 ng of pAM466 were digested to completion using XmaI restriction enzyme (New England Biolabs, Ipswich, Mass.), DNA fragments corresponding to the ERG20-$P_{GAL}$-tHMGR insert and the linearized pAM466 vector were gel purified, and 4 molar equivalents of the purified insert was ligated with 1 molar equivalent of the purified linearized vector, yielding pAM489 (see FIG. 5A for a map and SEQ ID NO: 3 for the nucleotide sequence of the ERG20-$P_{GAL}$-tHMGR insert).

TABLE 1

PCR amplifications performed to generate pAM489

| PCR Round | Template | Primer 1 | Primer 2 | PCR Product |
|---|---|---|---|---|
| 1 | 100 ng of Y051 genomic DNA | 61-67-CPK001-G (SEQ ID NO: 35) | 61-67-CPK002-G (SEQ ID NO: 36) | TRP1$^{-856\ to\ -226}$ |
|  |  | 61-67-CPK003-G (SEQ ID NO: 37) | 61-67-CPK004-G (SEQ ID NO: 38) | TRP1$^{-225\ to\ +548}$ |
|  | 100 ng of EG123 genomic DNA | 61-67-CPK025-G (SEQ ID NO: 59) | 61-67-CPK050-G (SEQ ID NO: 67) | ERG20 |
|  | 100 ng of Y002 genomic DNA | 61-67-CPK051-G (SEQ ID NO: 68) | 61-67-CPK052-G (SEQ ID NO: 69) | P$_{GAL}$ |
|  |  | 61-67-CPK053-G (SEQ ID NO: 70) | 61-67-CPK031-G (SEQ ID NO: 60) | tHMGR |
| 2 | 100 ng each of TRP1$^{-856\ to\ -226}$ and TRP1$^{-225\ to\ +548}$ purified PCR products | 61-67-CPK001-G (SEQ ID NO: 37) | 61-67-CPK004-G (SEQ ID NO: 38) | TRP1$^{-856\ to\ +548}$ |
|  | 100 ng each of ERG20 and P$_{GAL}$ purified PCR products | 61-67-CPK025-G (SEQ ID NO: 59) | 61-67-CPK052-G (SEQ ID NO: 69) | ERG20-P$_{GAL}$ |
| 3 | 100 ng each of ERG20-P$_{GAL}$ and tHMGR purified PCR products | 61-67-CPK025-G (SEQ ID NO: 59) | 61-67-CPK031-G (SEQ ID NO: 60) | ERG20-P$_{GAL}$-tHMGR |

Figure 5B:
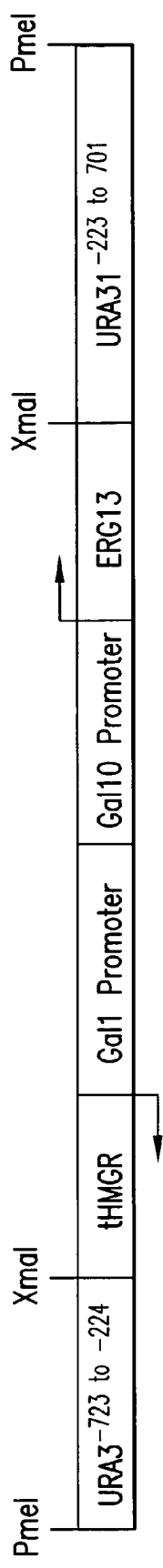

Plasmid pAM491 was generated by inserting the ERG13-P$_{GAL}$-tHMGR insert of vector pAM472 into vector pAM467.

pAM491 (see FIG. 5B for a map and SEQ ID NO: 4 for the nucleotide sequence of the ERG13-P$_{GAL}$-tHMGR insert).

TABLE 2

PCR amplifications performed to generate pAM491

| PCR Round | Template | Primer 1 | Primer 2 | PCR Product |
|---|---|---|---|---|
| 1 | 100 ng of Y007 genomic DNA | 61-67-CPK005-G (SEQ ID NO: 39) | 61-67-CPK006-G (SEQ ID NO: 40) | URA3$^{-723\ to\ -224}$ |
|  |  | 61-67-CPK007-G (SEQ ID NO: 41) | 61-67-CPK008-G (SEQ ID NO: 42) | URA3$^{-223\ to\ 701}$ |
|  | 100 ng of Y002 genomic DNA | 61-67-CPK032-G (SEQ ID NO: 61) | 61-67-CPK054-G (SEQ ID NO: 71) | ERG13 |
|  |  | 61-67-CPK052-G (SEQ ID NO: 69) | 61-67-CPK055-G (SEQ ID NO: 72) | P$_{GAL}$ |
|  |  | 61-67-CPK031-G (SEQ ID NO: 60) | 61-67-CPK053-G (SEQ ID NO: 70) | tHMGR |
| 2 | 100 ng each of URA3$^{-723\ to\ -224}$ and URA3$^{-223\ to\ 701}$ purified PCR products | 61-67-CPK005-G (SEQ ID NO: 39) | 61-67-CPK008-G (SEQ ID NO: 42) | URA3$^{-723\ to\ 701}$ |
|  | 100 ng each of ERG13 and P$_{GAL}$ purified PCR products | 61-67-CPK032-G (SEQ ID NO: 61) | 61-67-CPK052-G (SEQ ID NO: 69) | ERG13-P$_{GAL}$ |
| 3 | 100 ng each of ERG13-P$_{GAL}$ and tHMGR purified PCR products | 61-67-CPK031-G (SEQ ID NO: 60) | 61-67-CPK032-G (SEQ ID NO: 61) | ERG13-P$_{GAL}$-tHMGR |

Figure 5C:
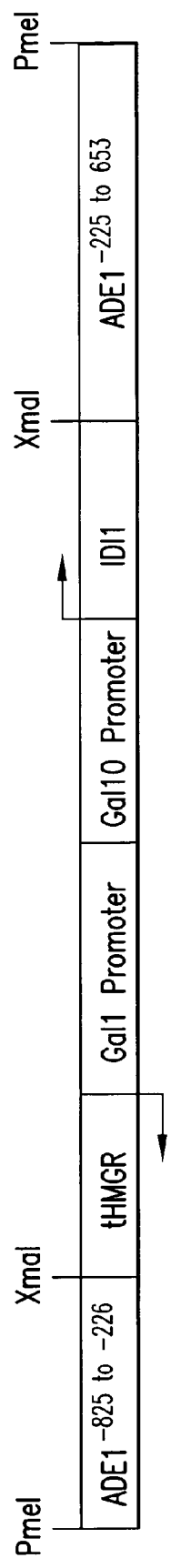

Vector pAM472 was generated by inserting DNA fragment ERG13-P$_{GAL}$-tHMGR, which comprises the ORF of ERG13 (ERG13 nucleotide positions 1 to 1626) (ERG13), the genomic locus containing the divergent GAL1 and GAL10 promoter (GAL1 nucleotide position −1 to −668) (P$_{GAL}$), and a truncated ORF of HMG1 (HMG1 nucleotide position 1586 to 3323) (tHMGR), into the XmaI restriction site of TOPO Zero Blunt II cloning vector. Vector pAM467 was generated by inserting DNA fragment URA3$^{-723\ to\ 701}$, which comprises a segment of the wild-type URA3 locus of Saccharomyces cerevisiae that extends from nucleotide position −723 to position −224 and harbors a non-native internal XmaI restriction site between bases −224 and −223, into the TOPO TA pCR2.1 cloning vector. DNA fragments ERG13-P$_{GAL}$-tHMGR and URA3$^{-723\ to\ 701}$ were generated by PCR amplification as outlined in Table 2. For the construction of pAM491, 400 ng of pAM472 and 100 ng of pAM467 were digested to completion using XmaI restriction enzyme, DNA fragments corresponding to the ERG13-P$_{GAL}$-tHMGR insert and the linearized pAM467 vector were gel purified, and 4 molar equivalents of the purified insert was ligated with 1 molar equivalent of the purified linearized vector, yielding Plasmid pAM493 was generated by inserting the IDI1-P$_{GAL}$-tHMGR insert of vector pAM473 into vector pAM468. Vector pAM473 was generated by inserting DNA fragment IDI1-P$_{GAL}$-tHMGR, which comprises the ORF of IDI1 (IDI1 nucleotide position 1 to 1017) (IDI1), the genomic locus containing the divergent GAL1 and GAL10 promoter (GAL1 nucleotide position −1 to −668) (P$_{GAL}$), and a truncated ORF of HMG1 (HMG1 nucleotide positions 1586 to 3323) (tHMGR), into the TOPO Zero Blunt II cloning vector. Vector pAM468 was generated by inserting DNA fragment ADE1$^{-825\ to\ 653}$, which comprises a segment of the wild-type ADE1 locus of Saccharomyces cerevisiae that extends from nucleotide position −225 to position 653 and harbors a non-native internal XmaI restriction site between bases −226 and −225, into the TOPO TA pCR2.1 cloning vector. DNA fragments IDI1-P$_{GAL}$-tHMGR and ADE1$^{-825\ to\ 653}$ were generated by PCR amplification as outlined in Table 3. For the construction of pAM493, 400 ng of pAM473 and 100 ng of pAM468 were digested to completion using XmaI restriction enzyme, DNA fragments corresponding to the IDI1-P$_{GAL}$-tHMGR insert and the linearized pAM468 vector were gel purified, and 4 molar equivalents of the purified insert was ligated with 1 molar equivalent of the purified linearized vector, yielding vector pAM493 (see FIG. 5C for a map and SEQ ID NO: 5 for the nucleotide sequence of the IDI1-P$_{GAL}$-tHMGR insert).

from nucleotide position 504 to position 1103, a HISMX marker, and a non-native XmaI restriction site between the HIS3$^{504\ to\ -1103}$ sequence and the HISMX marker, into the TOPO TA pCR2.1 cloning vector. DNA fragments ERG10-

TABLE 3

PCR amplifications performed to generate pAM493

| PCR Round | Template | Primer 1 | Primer 2 | PCR Product |
|---|---|---|---|---|
| 1 | 100 ng of Y007 genomic DNA | 61-67-CPK009-G (SEQ ID NO: 43) | 61-67-CPK010-G (SEQ ID NO: 44) | ADE1$^{-825\ to\ -226}$ |
|  |  | 61-67-CPK011-G (SEQ ID NO: 45) | 61-67-CPK012-G (SEQ ID NO: 46) | ADE1$^{-225\ to\ 653}$ |
|  | 100 ng of Y002 genomic DNA | 61-67-CPK047-G (SEQ ID NO: 66) | 61-67-CPK064-G (SEQ ID NO: 81) | IDI1 |
|  |  | 61-67-CPK052-G (SEQ ID NO: 69) | 61-67-CPK065-G (SEQ ID NO: 82) | P$_{GAL}$ |
|  |  | 61-67-CPK031-G (SEQ ID NO: 60) | 61-67-CPK053-G (SEQ ID NO: 70) | tHMGR |
| 2 | 100 ng each of ADE1$^{-825\ to\ -226}$ and ADE1$^{-225\ to\ 653}$ purified PCR products | 61-67-CPK009-G (SEQ ID NO: 43) | 61-67-CPK012-G (SEQ ID NO: 46) | ADE1$^{-825\ to\ 653}$ |
|  | 100 ng each of IDI1 and P$_{GAL}$ purified PCR products | 61-67-CPK047-G (SEQ ID NO: 66) | 61-67-CPK052-G (SEQ ID NO: 69) | IDI1-P$_{GAL}$ |
| 3 | 100 ng each of IDI1-P$_{GAL}$ and tHMGR purified PCR products | 61-67-CPK031-G (SEQ ID NO: 60) | 61-67-CPK047-G (SEQ ID NO: 66) | IDI1-P$_{GAL}$-tHMGR |

Figure 5D:
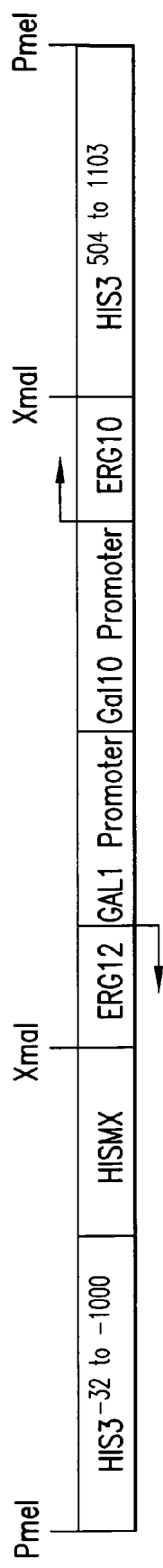

Plasmid pAM495 was generated by inserting the ERG10-P$_{GAL}$-ERG12 insert of pAM474 into vector pAM469. Vector pAM474 was generated by inserting DNA fragment ERG10-P$_{GAL}$-ERG12, which comprises the ORF of ERG10 (ERG10 nucleotide position 1 to 1347) (ERG10), the genomic locus containing the divergent GAL1 and GAL10 promoter (GAL1 nucleotide position −1 to −668) (P$_{GAL}$), and the ORF of ERG12 (ERG12 nucleotide position 1 to 1482) (ERG12), into the TOPO Zero Blunt II cloning vector. Vector pAM469 was generated by inserting DNA fragment HIS3$^{-32\ to\ -1000}$-HISMX-HIS3$^{504\ to\ -1103}$, which comprises two segments of the wild-type HIS locus of Saccharomyces cerevisiae that extend from nucleotide position −32 to position −1000 and P$_{GAL}$-ERG12 and HIS3$^{-32\ to\ -1000}$-HISMX-HIS3$^{504\ to\ -1103}$ were generated by PCR amplification as outlined in Table 4. For construction of pAM495, 400 ng of pAM474 and 100 ng of pAM469 were digested to completion using XmaI restriction enzyme, DNA fragments corresponding to the ERG10-P$_{GAL}$-ERG12 insert and the linearized pAM469 vector were gel purified, and 4 molar equivalents of the purified insert was ligated with 1 molar equivalent of the purified linearized vector, yielding vector pAM495 (see FIG. 5D for a map and SEQ ID NO: 6 for the nucleotide sequence of the ERG10-P$_{GAL}$-ERG12 insert).

TABLE 4

PCR reactions performed to generate pAM495

| PCR Round | Template | Primer 1 | Primer 2 | PCR Product |
|---|---|---|---|---|
| 1 | 100 ng of Y007 genomic DNA | 61-67-CPK013-G (SEQ ID NO: 47) | 61-67-CPK014alt-G (SEQ ID NO: 48) | HIS3$^{-32\ to\ -1000}$ |
|  |  | 61-67-CPK017-G (SEQ ID NO: 51) | 61-67-CPK018-G (SEQ ID NO: 52) | HIS3$^{504\ to\ -1103}$ |
|  |  | 61-67-CPK035-G (SEQ ID NO: 62) | 61-67-CPK056-G (SEQ ID NO: 73) | ERG10 |
|  |  | 61-67-CPK057-G (SEQ ID NO: 74) | 61-67-CPK058-G (SEQ ID NO: 75) | P$_{GAL}$ |
|  |  | 61-67-CPK040-G (SEQ ID NO: 63) | 61-67-CPK059-G (SEQ ID NO: 76) | ERG12 |
|  | 10 ng of plasmid pAM330 DNA ** | 61-67-CPK015alt-G (SEQ ID NO: 49) | 61-67-CPK016-G (SEQ ID NO: 50) | HISMX |
| 2 | 100 ng each of HIS3$^{504\ to\ -1103}$ and HISMX PCR purified products | 61-67-CPK015alt-G (SEQ ID NO: 49) | 61-67-CPK018-G (SEQ ID NO: 52) | HISMX-HIS3$^{504\ to\ -1103}$ |
|  | 100 ng each of ERG10 and P$_{GAL}$ purified PCR products | 61-67-CPK035-G (SEQ ID NO: 62) | 61-67-CPK058-G (SEQ ID NO: 75) | ERG10-P$_{GAL}$ |
| 3 | 100 ng each of HIS3$^{-32\ to\ -1000}$ and HISMX-HIS3$^{504\ to\ -1103}$ purified PCR products | 61-67-CPK013-G (SEQ ID NO: 47) | 61-67-CPK018-G (SEQ ID NO: 52) | HIS3$^{-32\ to\ -1000}$-HISMX-HIS3$^{504\ to\ -1103}$ |
|  | 100 ng each of ERG10-P$_{GAL}$ and ERG12 purified PCR products | 61-67-CPK035-G (SEQ ID NO: 62) | 61-67-CPK040-G (SEQ ID NO: 63) | ERG10-P$_{GAL}$-ERG12 |

** The HISMX marker in pAM330 originated from pFA6a-HISMX6-PGAL1 as described by van Dijken et al. ((2000) Enzyme Microb. Technol. 26(9-10): 706-714).

Figure 5E:
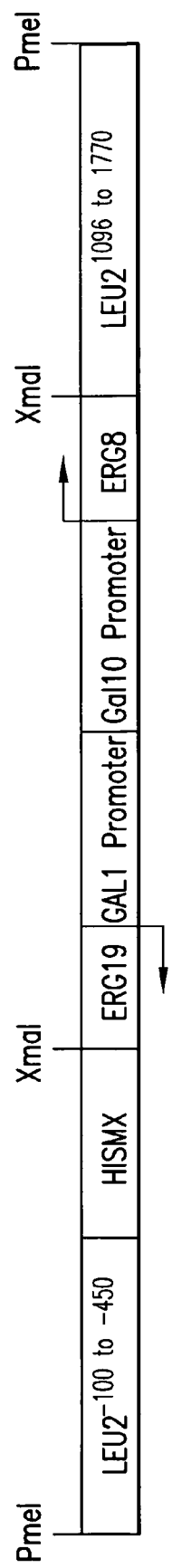
Figure 6:
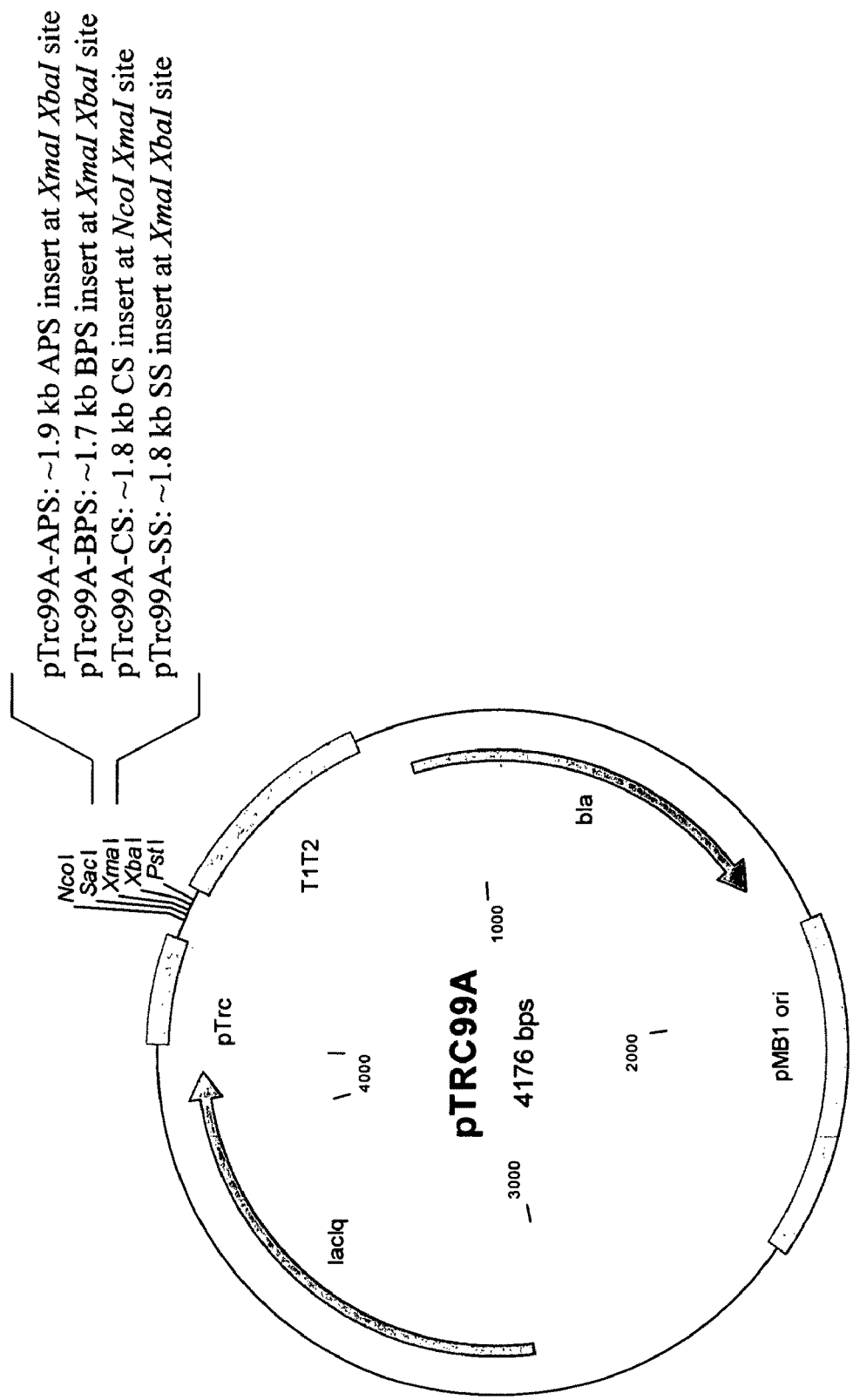
FIG. 6 shows maps of expression plasmids pTrc99A-APS, pTrc99A-BPS, pTrc99A-CS, and pTrc99A-SS.

Plasmid pAM497 was generated by inserting the ERG8-$P_{GAL}$-ERG19 insert of pAM475 into vector pAM470. Vector pAM475 was generated by inserting DNA fragment ERG8-$P_{GAL}$-ERG19, which comprises the ORF of ERG8 (ERG8 nucleotide position 1 to 1512) (ERG8), the genomic locus containing the divergent GAL1 and GAL10 promoter (GAL1 nucleotide position −1 to −668) ($P_{GA}$), and the ORF of ERG19 (ERG19 nucleotide position 1 to 1341) (ERG19), into the TOPO Zero Blunt II cloning vector. Vector pAM470 was generated by inserting DNA fragment LEU2$^{-100\ to\ 450}$-HISMX-LEU2$^{1096\ to\ 1770}$, which comprises two segments of the wild-type LEU2 locus of Saccharomyces cerevisiae that extend from nucleotide position −100 to position 450 and from nucleotide position 1096 to position 1770, a HISMX marker, and a non-native XmaI restriction site between the LEU2$^{1096\ to\ 1770}$ sequence and the HISMX marker, into the TOPO TA pCR2.1 cloning vector. DNA fragments ERG8-$P_{GAL}$-ERG19 and LEU2$^{-100\ to\ 450}$-HISMX-LEU2$^{1096\ to\ 1770}$ were generated by PCR amplification as outlined in Table 5. For the construction of pAM497, 400 ng of pAM475 and 100 ng of pAM470 were digested to completion using XmaI restriction enzyme, DNA fragments corresponding to the ERG8-$P_{GAL}$-ERG19 insert and the linearized pAM470 vector were purified, and 4 molar equivalents of the purified insert was ligated with 1 molar equivalent of the purified linearized vector, yielding vector pAM497 (see FIG. 5E for a map and SEQ ID NO: 7 for the nucleotide sequence of the ERG8-$P_{GAL}$-ERG19 insert).

flanked by a leader XmaI restriction site and a terminal XbaI restriction site. The synthetic nucleic acid was cloned into compatible restriction enzyme sites of a cloning vector such as a standard pUC or pACYC origin vector, from which it was liberated again by digesting the DNA synthesis construct to completion using XbaI and XmaI restriction enzymes, resolving the reaction mixture by gel electrophoresis, and gel extracting the approximately 1.9 kb terpene synthase encoding DNA fragment. The isolated DNA fragment was ligated into the XmaI XbaI restriction site of vector pTrc99A (Amman et al., Gene 40:183-190 (1985)), yielding expression plasmid pTrc99A-APS (see FIG. 6 for a plasmid map).

Expression plasmids pTrc99A-BPS, pTrc99A-CS, and pTrc99A-SS are generated by inserting a nucleotide sequence encoding a β-pinene synthase ("BPS"), carene synthase ("CS"), or sabinine synthase ("SS"), respectively, into the pTrc99A vector. The nucleotide sequence insert is generated synthetically, using as a template for example the coding sequence of the β-pinene synthase of Artemisia annua (GenBank accession number AF276072 REGION: 1 . . . 1749), the coding sequence of the carene synthase gene of Salvia stenophylla (GenBank accession number AF527416 REGION: 78 . . . 1871), or the coding sequence of the sabinine synthase gene of Salvia officinalis (GenBank accession number AF051901 REGION: 26 . . . 1798). The nucleotide sequences encoding the β-pinene and sabinine synthases are flanked by a leader XmaI restriction enzyme site and a terminal XbaI restriction enzyme site, and the nucleotide sequences encod-

TABLE 5

PCR reactions performed to generate pAM497

| PCR Round | Template | Primer 1 | Primer 2 | PCR Product |
|---|---|---|---|---|
| 1 | 100 ng of Y007 genomic DNA | 61-67-CPK019-G (SEQ ID NO: 53) | 61-67-CPK020-G (SEQ ID NO: 54) | LEU2$^{-100\ to\ 540}$ |
|  |  | 61-67-CPK023-G (SEQ ID NO: 57) | 61-67-CPK024-G (SEQ ID NO: 58) | LEU2$^{1096\ to\ 1770}$ |
|  | 10 ng of plasmid pAM330 DNA ** | 61-67-CPK021-G (SEQ ID NO: 55) | 61-67-CPK022-G (SEQ ID NO: 56) | HISMX |
|  | 100 ng of Y002 genomic DNA | 61-67-CPK041-G (SEQ ID NO: 64) | 61-67-CPK060-G (SEQ ID NO: 77) | ERG8 |
|  |  | 61-67-CPK061-G (SEQ ID NO: 78) | 61-67-CPK062-G (SEQ ID NO: 79) | $P_{GAL}$ |
|  |  | 61-67-CPK046-G (SEQ ID NO: 65) | 61-67-CPK063-G (SEQ ID NO: 80) | ERG19 |
| 2 | 100 ng each of LEU2$^{1096\ to\ 1770}$ and HISMX purified PCR products | 61-67-CPK021-G (SEQ ID NO: 55) | 61-67-CPK024-G (SEQ ID NO: 58) | HISMX-LEU2$^{1096\ to\ 1770}$ |
|  | 100 ng each of ERG8 and $P_{GAL}$ purified PCR products | 61-67-CPK041-G (SEQ ID NO: 64) | 61-67-CPK062-G (SEQ ID NO: 79) | ERG8-$P_{GAL}$ |
| 3 | 100 ng of LEU2$^{-100\ to\ 450}$ and HISMX- LEU2$^{1096\ to\ 1770}$ purified PCR products | 61-67-CPK019-G (SEQ ID NO: 53) | 61-67-CPK024-G (SEQ ID NO: 58) | LEU2$^{-100\ to\ 450}$-HISMX-LEU2$^{1096\ to\ 1770}$ |
|  | 100 ng each of ERG8-$P_{GAL}$ and ERG19 purified PCR products | 61-67-CPK041-G (SEQ ID NO: 64) | 61-67-CPK046-G (SEQ ID NO: 65) | ERG8-$P_{GAL}$-ERG19 |

** The HISMX marker in pAM330 originated from pFA6a-HISMX6-PGAL1 as described by van Dijken et al. ((2000) Enzyme Microb. Technol. 26(9-10): 706-714).

Example 5

This example describes methods for making expression plasmids that encode enzymes that convert GPP.

Expression plasmid pTrc99A-APS was generated by inserting a nucleotide sequence encoding an α-pinene synthase ("APS") into the pTrc99A vector. The nucleotide sequence insert was generated synthetically, using as a template the coding sequence of the α-pinene synthase gene of Pinus taeda (GenBank accession number AF543530 REGION: 1 . . . 1887), codon-optimized for expression in Escherichia coli (SEQ ID No:8). The coding sequence was ing the carene synthase is flanked by a leader NcoI restriction enzyme site and a terminal XmaI restriction enzyme site. The β-pinene and sabinine synthase DNA synthesis constructs are digested to completion using XmaI and XbaI restriction enzymes, and the carene synthase DNA synthesis construct is digested to completion using NcoI and XmaI restriction enzymes. The reaction mixture is resolved by gel electrophoresis, the approximately 1.7 to 1.8 kb DNA fragments is gel extracted, and the isolated DNA fragments is ligated into the XmaI XbaI restriction site (for the β-pinene and sabinine synthase inserts) or the NcoI XmaI restriction site (for the carene synthase insert) of the pTrc99A vector, yielding expression plasmid pTrc99A-BPS, pTrc99A-CS, or pTrc99A-SS (see FIG. 6 for plasmid maps).

Figure 7:
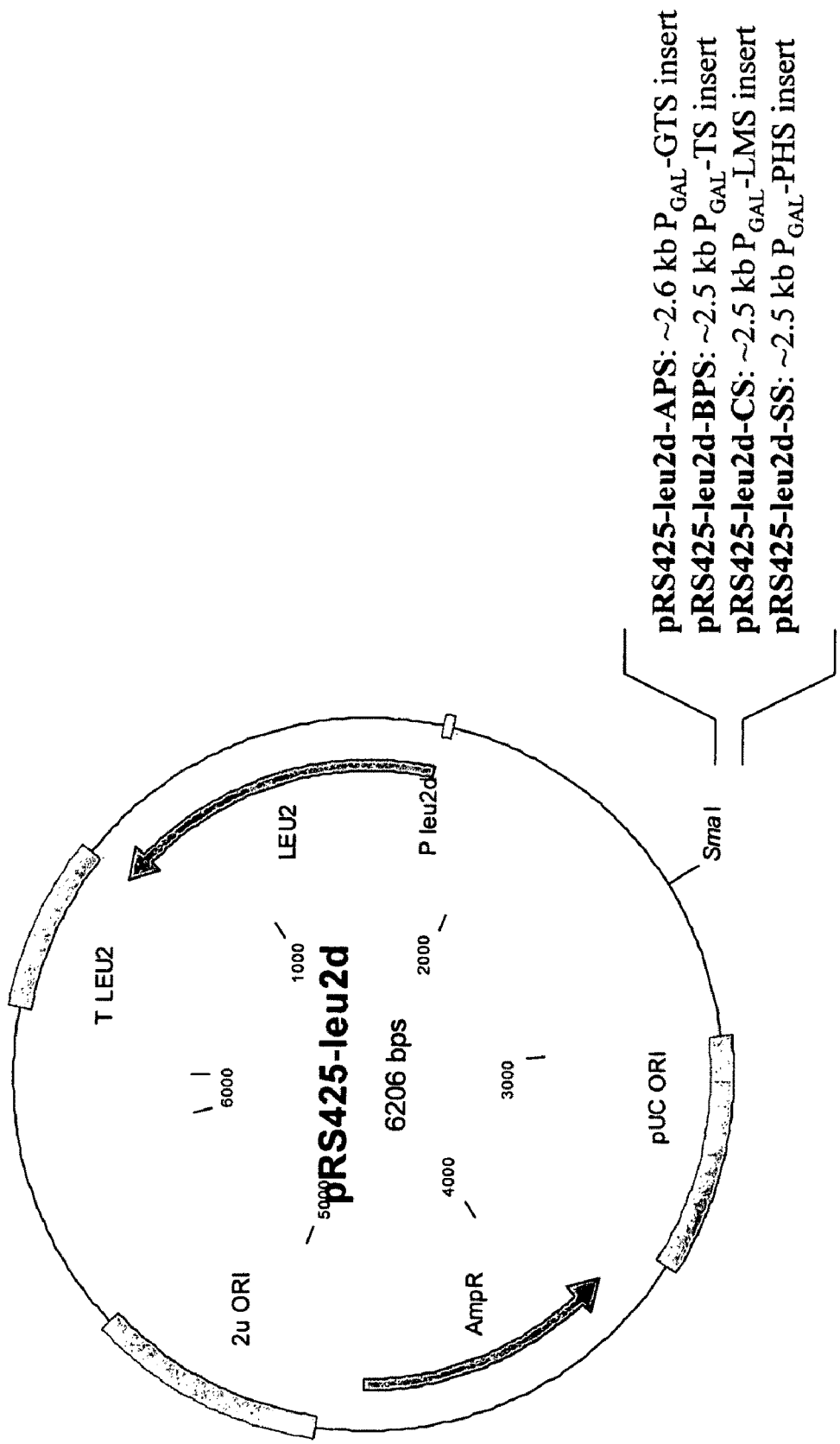
FIG. 7 shows maps of expression plasmids pRS425-leu2d-APS, pRS425-leu2d-BPS, pRS425-leu2d-CS, and pRS425-leu2d-SS.

Expression plasmid pRS425-leu2d-APS, pRS425-leu2d-BPS, pRS425-leu2d-CS, and pRS425-leu2d-SS are generated by inserting a nucleotide sequence encoding an α-pinene synthase ("APS"), a β-pinene synthase ("BPS"), a carene synthase ("CS"), or a sabinine synthase ("SS"), respectively, linked to the divergent GAL1 and GAL 10 promoter (GAL1 nucleotide position −1 to −668) ($P_{GA}$), into vector pRS425-leu2d. Vector pRS425-leu2d was generated by PCR amplifying the leu2 gene of pAM178 (SEQ ID NO: 10) using primers PW-91-079-CPK373-G (SEQ ID NO: 87) and PW-79-079-CPK374-G (SEQ ID NO: 88), and the backbone of vector pRS425 (GenBank accession number U03452) using primers PW-91-079-CPK376-G (SEQ ID NO: 89) and PW-79-079-CPK375-G (SEQ ID NO: 90), resolving the reaction mixtures by gel electrophoresis, gel extracting the approximately 1.6 kb leu2 gene fragment and the approximately 4.6 kb pRS425 vector backbone, treating the DNA fragments with T4 kinase to add terminal phosphate groups, and ligating the two DNA fragments. The nucleotide sequence insert is generated synthetically, using as a template for example the coding sequence of the α-pinene synthase gene of *Pinus taeda* (GenBank accession number AF543530 REGION: 1 . . . 1887), the coding sequence of the β-pinene synthase gene of *Artemisia annua* (GenBank accession number AF276072 REGION: 1 . . . 1749), the coding sequence of the carene synthase gene of *Salvia stenophylla* (GenBank accession number AF527416 REGION: 78 . . . 1871), or the coding sequence of the sabinine synthase gene of *Salvia officinalis* (GenBank accession number AF051901 REGION: 26 . . . 1798), each coding sequence being linked to the divergent GAL1 and GAL10 promoter (GAL1 nucleotide position −1 to −668) ($P_{GAL}$). The nucleotide sequence has blunted termini, and can thus be cloned into compatible restriction sites of a cloning vector such as a standard pUC or pACYC origin vector. The synthetically generated $P_{GAL}$-terpene synthase sequence is isolated by digesting the DNA synthesis construct to completion using SmaI restriction enzyme, the reaction mixture is resolved by gel electrophoresis, the approximately 2.5 kb to 2.6 kb DNA fragment is gel extracted, and the isolated DNA fragment is ligated into the SmaI restriction site of vector pRS425-leu2d, yielding expression plasmid pRS425-leu2d-APS, pRS425-leu2d-BPS, pRS425-leu2d-CS, or pRS425-leu2d-SS (see FIG. 7 for plasmid maps).

Example 6

This example describes the generation of *Escherichia coli* host strains useful in the invention.

As detailed in Table 6, host strains were or are created by transforming chemically competent *Escherichia coli* parent cells with one or more expression plasmids of Examples 1 through 3 and Example 5.

TABLE 6

*Escherichia coli* host strains

| Host Strain | E. coli Parent Strain | Expression Plasmids | Antibiotic Selection |
|---|---|---|---|
| 1 | DH1 | pMevT<br>pMBIS-gpps<br>pTrc99A-APS | 100 ug/mL carbenicillin<br>34 ug/mL chloramphenicol<br>5 ug/mL tetracycline |
| 2 | | pMevT<br>pMBIS-gpps<br>pTrc99A-BPS | |
| 3 | | pMevT<br>pMBIS-gpps<br>pTrc99A-CS | |
| 4 | | pMevT<br>pMBIS-gpps<br>pTrc99A-SS | |
| 5 | | pAM408<br>pAM424<br>pTrc99A-APS | 100 µg/ml carbenicillin<br>50 µg/ml kanamycin<br>35 µg/ml chloramphenicol |
| 6 | | pAM408<br>pAM424<br>pTrc99A-BPS | |
| 7 | | pAM408<br>pAM424<br>pTrc99A-CS | |
| 8 | | pAM408<br>pAM424<br>pTrc99A-SS | |

Host cell transformants are selected on Luria Bertoni (LB) agar containing antibiotics. Single colonies are transferred from LB agar to culture tubes containing 5 mL of LB liquid medium and antibiotics. The cultures are incubated at 37° C. on a rotary shaker at 250 rpm until growth reached late exponential phase. The cells are adapted to minimal media by passaging them through 4 to 5 successive rounds of M9-MOPS media containing 0.8% glucose and antibiotics (see Table 7 for the composition of the M9-MOPS medium). The cells are stored at −80° C. in cryo-vials in 1 mL stock aliquots made up of 400 uL sterile 50% glycerol and 600 uL liquid culture.

TABLE 7

Composition of M9-MOPS Culture Medium

| Component | Quantity (per L) |
|---|---|
| $Na_2HPO_4\ 7H_2O$ | 12.8 g |
| $KH_2PO_4$ | 3 g |
| NaCl | 0.5 g |
| $NH_4Cl$ | 1 g |
| $MgSO_4$ | 2 mmol |
| $CaCl_2$ | 0.1 mmol |
| Thiamine | 0.1 ug |
| MOPS buffer pH 7.4 | 100 mmol |
| $(NH_3)_6Mo_7O_{24}\ 4H_2O$ | 3.7 ug |
| $H_3BO_4$ | 25 ug |
| $CoCl_2$ | 7.1 ug |
| $CuSO_4$ | 2.4 ug |
| $MnCl_2$ | 16 ug |
| $ZnSO_4$ | 2.9 ug |
| $FeSO_4$ | 0.28 mg |

Example 7

This example describes the generation of *Saccharomyces cerevisiae* strains useful in the invention.

*Saccharomyces cerevisiae* strains CEN.PK2-1C (Y002) (MATA; ura3-52; trp1-289; leu2-3,112; his3Δ1; MAL2-8C; SUC2) and CEN.PK2-1D (Y003) (MATalpha; ura3-52; trp1-289; leu2-3,112; his3Δ1; MAL2-8C; SUC2) (van Dijken et al. (2000) *Enzyme Microb. Technol.* 26(9-10):706-714) were prepared for introduction of inducible MEV pathway genes by replacing the ERG9 promoter with the *Saccharomyces cerevisiae* MET3 promoter, and the ADE1 ORF with the *Candida glabrata* LEU2 gene (CgLEU2). This was done by PCR amplifying the KanMX-PMET3 region of vector pAM328 (SEQ ID NO: 9) using primers 50-56-pw100-G (SEQ ID NO: 85) and 50-56-pw101-G (SEQ ID NO: 86), which include 45 base pairs of homology to the native ERG9 promoter, transforming 10 ug of the resulting PCR product into exponentially growing Y002 and Y003 cells using 40% w/w Polyethelene Glycol 3350 (Sigma-Aldrich, St. Louis, Mo.), 100 mM Lithium Acetate (Sigma-Aldrich, St. Louis, Mo.), and 10 ug Salmon Sperm DNA (Invitrogen Corp., Carlsbad, Calif.), and incubating the cells at 30° C. for 30 minutes followed by heat shocking them at 42° C. for 30 minutes (Schiestl and Gietz. (1989) Curr. Genet. 16, 339-346). Positive recombinants were identified by their ability to grow on rich medium containing 0.5 ug/ml Geneticin (Invitrogen Corp., Carlsbad, Calif.), and selected colonies were confirmed by diagnostic PCR. The resultant clones were given the designation Y93 (MAT A) and Y94 (MAT alpha). The 3.5 kb CgLEU2 genomic locus was then amplified from Candida glabrata genomic DNA (ATCC, Manassas, Va.) using primers 61-67-CPK066-G (SEQ ID NO: 83) and 61-67-CPK067-G (SEQ ID NO: 84), which contain 50 base pairs of flanking homology to the ADE1 ORF, and 10 ug of the resulting PCR product were transformed into exponentially growing Y93 and Y94 cells, positive recombinants were selected for growth in the absence of leucine supplementation, and selected clones were confirmed by diagnostic PCR. The resultant clones were given the designation Y176 (MAT A) and Y177 (MAT alpha).

Strain Y188 was then generated by digesting 2 ug of pAM491 and pAM495 plasmid DNA to completion using PmeI restriction enzyme (New England Biolabs, Beverly, Mass.), and introducing the purified DNA inserts into exponentially growing Y176 cells. Positive recombinants were selected for by growth on medium lacking uracil and histidine, and integration into the correct genomic locus was confirmed by diagnostic PCR.

Strain Y189 was next generated by digesting 2 ug of pAM489 and pAM497 plasmid DNA to completion using PmeI restriction enzyme, and introducing the purified DNA inserts into exponentially growing Y177 cells. Positive recombinants were selected for by growth on medium lacking tryptophan and histidine, and integration into the correct genomic locus was confirmed by diagnostic PCR.

Approximately $1 \times 10^7$ cells from strains Y188 and Y189 were mixed on a YPD medium plate for 6 hours at room temperature to allow for mating. The mixed cell culture was plated to medium lacking histidine, uracil, and tryptophan to select for growth of diploid cells. Strain Y238 was generated by transforming the diploid cells using 2 ug of pAM493 plasmid DNA that had been digested to completion using PmeI restriction enzyme, and introducing the purified DNA insert into the exponentially growing diploid cells. Positive recombinants were selected for by growth on medium lacking adenine, and integration into the correct genomic locus was confirmed by diagnostic PCR.

Haploid strain Y211 (MAT alpha) was generated by sporulating strain Y238 in 2% Potassium Acetate and 0.02% Raffinose liquid medium, isolating approximately 200 genetic tetrads using a Singer Instruments MSM300 series micromanipulator (Singer Instrument LTD, Somerset, UK), identifying independent genetic isolates containing the appropriate complement of introduced genetic material by their ability to grow in the absence of adenine, histidine, uracil, and tryptophan, and confirming the integration of all introduced DNA by diagnostic PCR.

Finally, host strains 9 through 12 are generated by transforming strain Y211 with expression plasmid pRS425-leu2d-APS, pRS425-leu2d-BPS, pRS425-leu2d-CS, or pRS425-leu2d-SS. Host cell transformants are selected on synthetic defined media, containing 2% glucose and all amino acids except leucine (SM-glu). Single colonies are transferred to culture vials containing 5 mL of liquid SM-glu lacking leucine, and the cultures are incubated by shaking at 30° C. until growth reaches stationary phase. The cells are stored at −80° C. in cryo-vials in 1 mL frozen aliquots made up of 400 uL 50% sterile glycerol and 600 uL liquid culture.

Example 8

This example describes the production of α-pinene, β-pinene, carene, and sabinine via the MEV pathway in Escherichia coli host strains.

Seed cultures of the host strains 1 through 4 are established by adding a stock aliquot of each strain to separate 125 mL flasks containing 25 mL M9-MOPS, 2% glucose, 0.5% yeast extract, and antibiotics as detailed in Table 6, and by growing the cultures overnight. The seed cultures are used to inoculate at an initial $OD_{600}$ of approximately 0.05 separate 250 mL flasks containing 40 mL M9-MOPS, 2% glucose, 0.5% yeast extract, and antibiotics. Cultures are incubated at 30° C. on a rotary shaker at 250 rpm until they reach an $OD_{600}$ of approximately 0.2, at which point the production of the compound of interest in the host cells is induced by adding 40 uL of 1 M IPTG to the culture medium. The compound of interest is separated from the culture medium through solvent-solvent extraction, or by settling and decantation if the titer of the compound of interest is large enough to saturate the media and to form a second phase.

Example 9

This example describes the production of α-pinene, β-pinene, carene, and sabinine via the DXP pathway in Escherichia coli host strains.

Seed cultures of the host strains 5 through 8 are established by adding a stock aliquot of each strain to separate 125 mL flasks containing 25 mL M9-MOPS, 0.8% glucose, 0.5% yeast extract, and antibiotics as detailed in Table 6, and by growing the cultures overnight. The seed cultures are used to inoculate at an initial $OD_{600}$ of approximately 0.05 separate 250 mL flasks containing 40 mL M9-MOPS, 45 ug/mL thiamine, micronutrients, 1.00E-5 mol/L FeSO4, 0.1 M MOPS, 2% glucose, 0.5% yeast extract, and antibiotics. Cultures are incubated at 30° C. in a humidified incubating shaker at 250 rpm until they reach an $OD_{600}$ of 0.2 to 0.3, at which point the production of the compound of interest in the host cells is induced by adding 40 uL of 1M IPTG to the culture medium. The compound of interest is separated from the culture medium through solvent-solvent extraction, or by settling and decantation if the titer of the compound of interest is large enough to saturate the media and to form a second phase.

Example 10

This example describes the production of α-pinene, β-pinene, carene, and sabinine in Saccharomyces cerevisiae host strains.

Seed cultures of host strains 9 through 12 are established by adding stock aliquots to separate 125 mL flasks containing 25 mL SM-glu lacking leucine, and growing each culture over night. The seed culture is used to inoculate at an initial $OD_{600}$ of approximately 0.05 a 250 mL baffled flask containing 40 mL of synthetic defined media containing 0.2% glucose and 1.8% galactose, and lacking leucine. The culture is incubated at 30° C. on a rotary shaker at 200 rpm. The compound of interest is separated from the culture medium through solvent-solvent extraction, or by settling and decantation if the titer of the compound of interest is large enough to saturate the media and to form a second phase.

Example 11

This example describes the hydrogenation of α-pinene to pinane.

To a reaction vessel, α-pinene and 10% Pd/C [palladium, 10 wt. % on activated carbon, Aldrich #205699] are added at 6 g/L loading. The vessel is sealed, purged with nitrogen gas, then evacuated under house vacuum. To begin the reaction, the vessel is stirred while adding compressed hydrogen gas at 80 psig. The mildly exothermic reaction proceeds at room temperature. Final conversion is 100%, marked by end to hydrogen consumption and verified by gas chromatography with flame ionization detection. The product-catalyst mixture is separated via gravity filtration through a 60 A silica gel and analyzed with Agilent DB-XLB column and flame ionization detector.

Example 12

Figure 9:
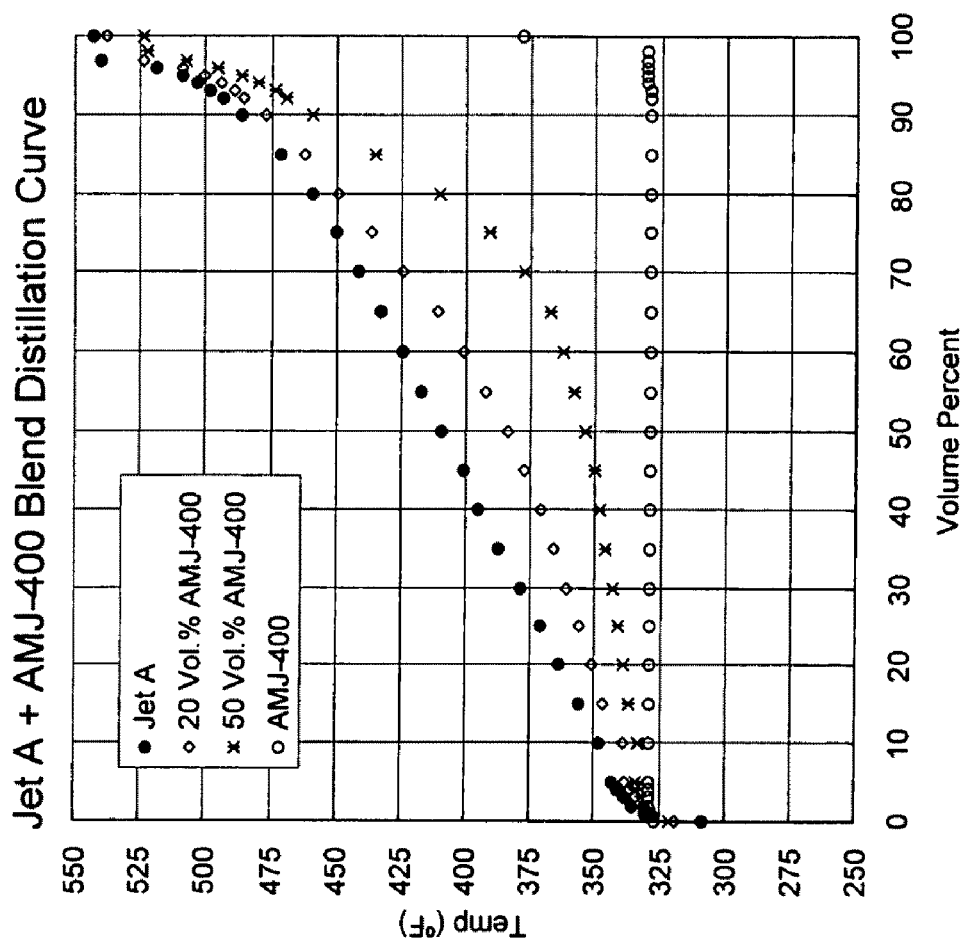
FIG. 9 shows the distillation curves for a Jet A and certain blends of Jet A and AMJ-400.

A fuel composition (referred to as AMJ-400) comprising 98.7% pinane is blended with various amounts of Jet A. The components of AMJ-400 were identified by gas chromatography/flame ionization detector (GC/FID). The results of the various blends for their ability to meet ASTM D 1655 are shown in FIG. 8: Jet A, 100% AMJ-400, 50% AMJ-400 and 50% Jet A, and 20% AMJ-400 and 80% Jet A. FIG. 9 shows the distillation curves for a Jet A and certain blends of Jet A and AMJ-400.

The fuel compositions described herein can be produced in a cost-effective and environmentally friendly manner. Advantageously, the $C_{10}$ bicyclic isoprenoid compounds used in the fuel compositions herein can be produced by one or more microorganisms. These $C_{10}$ bicyclic isoprenoid compounds can thus provide a renewable source of energy for diesel or jet fuels, in particularly the fuel compositions provided herein. Further, these $C_{10}$ bicyclic isoprenoid compounds can decrease dependence on non-renewable sources of fuel, fuel components and/or fuel additives. In certain embodiments, the fuel composition provided herein comprises a bioengineered carane, pinane, and sabinane.

While the invention has been described with respect to a limited number of embodiments, the specific features of one embodiment should not be attributed to other embodiments of the invention. No single embodiment is representative of all aspects of the claimed subject matter. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. It should be noted that the application of the jet fuel compositions disclosed herein is not limited to jet engines; they can be used in any equipment which requires a jet fuel. Although there are specifications for most jet fuels, not all jet fuel compositions disclosed herein need to meet all requirements in the specifications. It is noted that the methods for making and using the jet fuel compositions disclosed herein are described with reference to a number of steps. These steps can be practiced in any sequence. One or more steps may be omitted or combined but still achieve substantially the same results. The appended claims intend to cover all such variations and modifications as falling within the scope of the invention.

All publications and patent applications mentioned in this specification are herein incorporated by reference to the same extent as if each individual publication or patent application was specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The fuel compositions described herein can be produced in a cost-effective and environmentally friendly manner. Advantageously, the $C_{10}$ bicyclic isoprenoid compounds used in the fuel compositions herein can be produced by one or more microorganisms. These $C_{10}$ bicyclic isoprenoid compounds can thus provide a renewable source of energy for diesel or jet fuels, in particularly the fuel compositions provided herein. Further, these $C_{10}$ bicyclic isoprenoid compounds can decrease dependence on non-renewable sources of fuel, fuel components and/or fuel additives. In certain embodiments, the fuel composition provided herein comprises a bioengineered carane, pinane, and sabinane.

While the invention has been described with respect to a limited number of embodiments, the specific features of one embodiment should not be attributed to other embodiments of the invention. No single embodiment is representative of all aspects of the claimed subject matter. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. It should be noted that the application of the jet fuel compositions disclosed herein is not limited to jet engines; they can be used in any equipment which requires a jet fuel. Although there are specifications for most jet fuels, not all jet fuel compositions disclosed herein need to meet all requirements in the specifications. It is noted that the methods for making and using the jet fuel compositions disclosed herein are described with reference to a number of steps. These steps can be practiced in any sequence. One or more steps may be omitted or combined but still achieve substantially the same results. The appended claims intend to cover all such variations and modifications as falling within the scope of the invention.

All publications and patent applications mentioned in this specification are herein incorporated by reference to the same extent as if each individual publication or patent application was specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A fuel composition comprising or obtainable from a mixture comprising:
   (a) a $C_{10}$ bicyclic isoprenoid;
   (b) a petroleum-based fuel; and
   (c) a fuel additive,
wherein the amount of the $C_{10}$ bicyclic isoprenoid is at least about 2 vol. % and the amount of the petroleum-based fuel is at least about 5 vol. %, both amounts based on the total volume of the fuel composition, and wherein the fuel composition has a flash point equal to or greater than 38° C. and a density at 15° C. from about 750 kg/m³ to about 850 kg/m³, and wherein where the $C_{10}$ bicyclic isoprenoid is pinane, the fuel composition comprises from 0% to 10% of a hydrogenated naphthalene-containing material.

2. A fuel composition comprising or obtainable from a mixture comprising:
   (a) a $C_{10}$ bicyclic isoprenoid;
   (b) a petroleum-based fuel;
   (c) a fuel additive; and
   (d) an aromatic compound,
wherein the amount of the $C_{10}$ bicyclic isoprenoid is at least about 2 vol. %, the amount of the petroleum-based fuel is at least about 5 vol. %, and the amount of the aromatic compound is from about 5 vol. % to about 35 vol. %, all amounts based on the total volume of the fuel composition, and wherein the fuel composition has a flash point equal to or greater than 38° C. and a density at 15° C. from about 750 kg/m³ to about 850 kg/m³, and wherein where the $C_{10}$ bicyclic isoprenoid is pinane, the fuel composition comprises from 0% to 10% of a hydrogenated naphthalene-containing material.

3. A jet fuel composition comprising:
   (a) a $C_{10}$ bicyclic isoprenoid;
   (b) a petroleum-based fuel; and
   (c) a jet fuel additive; and
wherein the amount of the $C_{10}$ bicyclic isoprenoid is at least about 2 vol. %, and the amount of the petroleum-based fuel is at least about 5 vol. %, both amounts based on the total volume of the fuel composition, and wherein the fuel composition has a density from about 750 kg/m³ to about 850 kg/m³ at 15° C., a flash point equal to or greater than 38° C., and wherein where the $C_{10}$ bicyclic isoprenoid is pinane, the fuel composition comprises from 0% to 10% of a hydrogenated naphthalene-containing material.

4. The fuel composition of any of claims 1-3, wherein the $C_{10}$ bicyclic isoprenoid is carane, pinane, sabinane, or a combination thereof.

5. The fuel composition of any of claims 1-3, wherein the amount of the $C_{10}$ bicyclic isoprenoid is at least about 5 vol. %, based on the total volume of the fuel composition.

6. The fuel composition of any of claims 1-3, wherein the amount of the $C_{10}$ bicyclic isoprenoid is at least about 10 vol. %, based on the total volume of the fuel composition.

7. The fuel composition of any of claims 1-3, wherein the amount of the $C_{10}$ bicyclic isoprenoid is at least about 15 vol. %, based on the total volume of the fuel composition.

8. The fuel composition of any of claims 1-3, wherein the amount of the $C_{10}$ bicyclic isoprenoid is at least about 30 vol. %, based on the total volume of the fuel composition.

9. The fuel composition of claim 2, wherein the composition comprises p-cymene.

10. The fuel composition of claim 2, wherein the amount of the aromatic compound is at most about 25 vol. %, based on the total volume of the fuel composition.

11. The fuel composition of claim 1 or 2, wherein the petroleum-based fuel is kerosene.

12. The fuel composition of any of claims 1-3, wherein the petroleum-based fuel is Jet A, Jet A-1 or Jet B.

13. The fuel composition of claim 12, wherein the fuel composition meets the ASTM D 1655 specification for Jet A.

14. The fuel composition of claim 12, wherein the fuel composition meets the ASTM D 1655 specification for Jet A-1.

15. The fuel composition of claim 12, wherein the fuel composition meets the ASTM D 1655 specification for Jet B.

16. The jet fuel composition of claim 3, wherein the fuel additive is at least one additive selected from the group consisting of an oxygenate, an antioxidant, a thermal stability improver, a stabilizer, a cold flow improver, a combustion improver, an anti-foam, an anti-haze additive, a corrosion inhibitor, a lubricity improver, an icing inhibitor, an injector cleanliness additive, a smoke suppressant, a drag reducing additive, a metal deactivator, a dispersant, a detergent, a de-emulsifier, a dye, a marker, a static dissipater, a biocide, and combinations thereof.

17. A method of making a fuel composition comprising:
   (a) contacting a $C_{10}$ isoprenoid starting material with hydrogen in the presence of a catalyst to form a $C_{10}$ bicyclic isoprenoid; and
   (b) mixing the $C_{10}$ bicyclic isoprenoid with a petroleum-based fuel to make the fuel composition;
wherein the amount of the $C_{10}$ bicyclic isoprenoid is at least about 2 vol. % and the amount of the petroleum-based fuel is at least about 5 vol. %, both amounts based on the total volume of the fuel composition, and wherein the fuel composition has a flash point equal to or greater than 38° C., and wherein where the $C_{10}$ bicyclic isoprenoid is pinane, the fuel composition comprises from 0% to 10% of a hydrogenated naphthalene-containing material.

18. The method of claim 17, wherein the $C_{10}$ isoprenoid starting material is carene, α-pinene, β-pinene, sabinene, or a combination thereof.

19. A method of making a fuel composition from a simple sugar comprising:
   (a) contacting a cell capable of making a $C_{10}$ isoprenoid starting material with the simple sugar under conditions suitable for making the $C_{10}$ isoprenoid starting material;
   (b) converting the $C_{10}$ isoprenoid starting material to a $C_{10}$ bicyclic isoprenoid; and
   (c) mixing the $C_{10}$ bicyclic isoprenoid with a petroleum-based fuel to make the fuel composition, wherein the amount of the $C_{10}$ bicyclic isoprenoid is at least about 2 vol. % and the amount of the petroleum-based fuel is at least about 5 vol. %, both amounts based on the total volume of the fuel composition, and wherein the fuel composition has a flash point equal to or greater than 38° C., and wherein where the $C_{10}$ bicyclic isoprenoid is pinane, the fuel composition comprises from 0% to 10% of a hydrogenated naphthalene-containing material.

20. The method of claim 19, wherein the $C_{10}$ isoprenoid starting material is carene, α-pinene, β-pinene, sabinene, or a combination thereof.

21. A fuel composition made by the method of any of claims 17-20.

22. A vehicle comprising an internal combustion engine, a fuel tank connected to the internal combustion engine, and a fuel composition in the fuel tank, wherein the fuel composition is the fuel composition of any of claims 1-3, wherein the amount of the $C_{10}$ bicyclic isoprenoid is at least about 2 vol. % and the amount of the petroleum-based fuel is at least about 5 vol. %, both amounts based on the total volume of the fuel composition, and wherein the fuel composition has a flash point equal to or greater than 38° C. and wherein the fuel composition is used to power the internal combustion engine.

23. A method of powering an engine comprising the step of combusting the fuel composition of any of claims 1-3 in the engine.

24. The method of claim 22, wherein the engine is a jet engine.

25. A fuel composition comprising or obtainable from a mixture comprising:
   (a) a $C_{10}$ bicyclic isoprenoid;
   (b) a petroleum-based fuel; and
   (c) a fuel additive,
wherein the amount of the $C_{10}$ bicyclic isoprenoid is at least about 2 vol. % and the amount of the petroleum-based fuel is at least about 5 vol. %, both amounts based on the total volume of the fuel composition, and wherein the fuel composition has a flash point equal to or greater than 38° C. and a density at 15° C. from about 750 kg/m$^3$ to about 850 kg/m$^3$, and wherein the petroleum-based fuel is kerosene, Jet A, Jet A-1, Jet B or a combination thereof.

26. A fuel composition comprising or obtainable from a mixture comprising:
   (a) a $C_{10}$ bicyclic isoprenoid;
   (b) a petroleum-based fuel;
   (c) a fuel additive; and
   (d) an aromatic compound,
wherein the amount of the $C_{10}$ bicyclic isoprenoid is at least about 2 vol. %, the amount of the petroleum-based fuel is at least about 5 vol. %, and the amount of the aromatic compound is from about 5 vol. % to about 35 vol. %, all amounts based on the total volume of the fuel composition, and wherein the fuel composition has a flash point equal to or greater than 38° C. and a density at 15° C. from about 750 kg/m$^3$ to about 850 kg/m$^3$, and wherein , and wherein the petroleum-based fuel is kerosene, Jet A, Jet A-1, Jet B or a combination thereof.

27. A jet fuel composition comprising:
   (a) a $C_{10}$ bicyclic isoprenoid;
   (b) a petroleum-based fuel; and
   (c) a jet fuel additive; and
wherein the amount of the $C_{10}$ bicyclic isoprenoid is at least about 2 vol. %, the amount of the petroleum-based fuel is at least about 5 vol. %, both amounts based on the total volume of the fuel composition, and wherein the fuel composition has a density from about 750 kg/m$^3$ to about 850 kg/m$^3$ at 15° C., a flash point equal to or greater than 38° C., wherein the petroleum-based fuel is kerosene, Jet A, Jet A-1, Jet B or a combination thereof.

* * * * *